United States Patent
Ghasparian et al.

(10) Patent No.: US 11,680,085 B2
(45) Date of Patent: Jun. 20, 2023

(54) CYCLIC PEPTIDES FOR PROTECTION AGAINST RESPIRATORY SYNCYTIAL VIRUS

(71) Applicants: VIROMETIX AG, Schlieren (CH); UNIVERSITÄT ZÜRICH, Zürich (CH)

(72) Inventors: Arin Ghasparian, Zürich (CH); Armando Zuniga, Zürich (CH); Aniebrys Marrero Nodarse, Zürich (CH); Oliver Rassek, Adliswil (CH); John A. Robinson, Kemptthal (CH); Kerstin Möhle, Wettswil (CH)

(73) Assignees: VIROMETIX AG, Schlieren (CH); UNIVERSITÄT ZÜRICH, Zürich (CH)

( * ) Notice: Subject to any disclaimer, the term of this patent is extended or adjusted under 35 U.S.C. 154(b) by 0 days.

(21) Appl. No.: 16/622,023

(22) PCT Filed: Jun. 13, 2018

(86) PCT No.: PCT/EP2018/065714
§ 371 (c)(1),
(2) Date: Dec. 12, 2019

(87) PCT Pub. No.: WO2018/229156
PCT Pub. Date: Dec. 20, 2018

(65) Prior Publication Data
US 2021/0101941 A1   Apr. 8, 2021

(30) Foreign Application Priority Data

Jun. 14, 2017   (EP) .................................... 17176068

(51) Int. Cl.
| | | |
|---|---|---|
| C07K 14/08 | (2006.01) | |
| A61K 39/12 | (2006.01) | |
| C07K 14/005 | (2006.01) | |
| A61K 39/00 | (2006.01) | |

(52) U.S. Cl.
CPC .............. *C07K 14/08* (2013.01); *A61K 39/12* (2013.01); *C07K 14/005* (2013.01); *A61K 2039/5258* (2013.01); *A61K 2039/6018* (2013.01); *C12N 2760/00023* (2013.01)

(58) Field of Classification Search
None
See application file for complete search history.

(56) References Cited

U.S. PATENT DOCUMENTS

2021/0101941 A1*  4/2021  Ghasparian ............ A61K 39/12

FOREIGN PATENT DOCUMENTS

| RU | 2 422 444 C2 | 6/2011 |
|---|---|---|
| WO | 2001/089562 A1 | 11/2001 |
| WO | 2005/061513 A1 | 12/2004 |
| WO | 2014/144756 A1 | 9/2014 |
| WO | 2014/160463 A1 | 10/2014 |

OTHER PUBLICATIONS

Efstathiou et al. (Cellular and Molecular Life Sciences. 2020; 77: 5045-5058).*
Murphy et al. (Virus Research. 1994; 32: 13-26).*
Ghasparian et al. (ChemBioChem. 2011; 12: 100-109).*
Jin (Future Medicinal Chemistry 12.19 (2020): 1687-1690.*
Chhikara et al. (Applied NanoMedicine. 2022; 22 (1): 354-354).*
Riedel et al., "Synthetic virus-like particles and conformationally constrained peptides in vaccine design", Chembiochem—A European Journal of Chemical Biology, 12(18): 2829-2836 (2011).
The International Search Report issued in International Application No. PCT/EP2018/065714 dated Aug. 16, 2018.
Boata et al., "Synthetic Virus-Like Particles from Self-Assembling Coiled-Coil Lipopeptides and Their Use in Antigen Display to the Immune System," Angew. Chem. Int. Ed. 46(47):9015-9018 (2007).
Ghasparian et al., "Engineered Synthetic Virus-Like Particles and Their Use in Vaccine Delivery," ChemBioChem 12(1):100-109 (2011).
Lopez et al., "Conformational constraints of conserved neutralizing epitopes from a major antigenic area of human respiratory syncytial virus fusion glycoprotein," Journal of General Virology 74(12):2567-2577 (1993).
McLellan et al., "Design and characterization of epitope-scaffold immunogens that present the motavizumab epitope from respiratory syncytial virus," Journal of Molecular Biology 409(5):853-866 (2011).

* cited by examiner

*Primary Examiner* — Shanon A. Foley
(74) *Attorney, Agent, or Firm* — Medler Ferro Woodhouse & Mills PLLC

(57) ABSTRACT

The present invention relates to a cyclic peptide, a conjugate comprising said cyclic peptide and a lipopeptide building block, a bundle of said conjugates, a synthetic virus-like particle comprising at least one bundle of conjugates and pharmaceutical compositions comprising the same. The present invention further relates to said cyclic peptide, said conjugate said bundle of conjugates, said synthetic virus-like particle and said pharmaceutical compositions for use as a medicament, preferably for use in a method for preventing of an infectious disease or reducing the risk of an infectious disease, more preferably for use in a method for preventing or reducing the risk of an infectious disease associated with or caused by a respiratory syncytial virus.

20 Claims, No Drawings
Specification includes a Sequence Listing.

SEQUENCE LISTING

<160> NUMBER OF SEQ ID NOS: 66

<210> SEQ ID NO 1
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: Any amino acid
<220> FEATURE:
<221> NAME/KEY: MISC_FEATURE
<222> LOCATION: (5)..(7)
<223> OTHER INFORMATION: Any amino acid
<220> FEATURE:
<221> NAME/KEY: MISC_FEATURE
<222> LOCATION: (9)..(11)
<223> OTHER INFORMATION: Any amino acid
<220> FEATURE:
<221> NAME/KEY: MISC_FEATURE
<222> LOCATION: (22)..(24)
<223> OTHER INFORMATION: Any amino acid
<220> FEATURE:
<221> NAME/KEY: MISC_FEATURE
<222> LOCATION: (26)..(30)
<223> OTHER INFORMATION: Any amino acid

<400> SEQUENCE: 1

Xaa Xaa Xaa Cys Xaa Xaa Xaa Cys Xaa Xaa Xaa Pro Ile Thr Asn Asp
1               5                   10                  15

Gln Lys Lys Leu Cys Xaa Xaa Xaa Cys Xaa Xaa Xaa Xaa Xaa
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 2

Asn Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE

```
<222> LOCATION: (30)..(30)
<223> OTHER INFORMATION: D-alanine

<400> SEQUENCE: 3

Asn Ser Glu Cys Leu Ser Leu Cys Asn Asp Xaa Pro Ile Thr Asn Asp
1               5                   10                  15

Gln Lys Lys Leu Cys Ser Asn Lys Cys Gln Ser Val Arg Xaa
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (12)..(12)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 4

Arg Leu Ser Glu Cys Leu Ser Leu Cys Asn Asp Xaa Pro Ile Thr Asn
1               5                   10                  15

Asp Gln Lys Lys Leu Cys Ser Asn Asn Cys Leu Lys Ser Xaa
            20                  25                  30

<210> SEQ ID NO 5
<211> LENGTH: 40
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (40)..(40)
<223> OTHER INFORMATION: D-alanine

<400> SEQUENCE: 5

Pro Val Ser Thr Tyr Met Leu Thr Asn Ser Glu Cys Leu Ser Leu Cys
1               5                   10                  15

Asn Asp Met Pro Ile Thr Asn Asp Gln Lys Lys Leu Cys Ser Asn Asn
            20                  25                  30

Cys Gln Ile Val Arg Gln Gln Xaa
        35                  40

<210> SEQ ID NO 6
<211> LENGTH: 20
<212> TYPE: PRT
<213> ORGANISM: Artificial Sequence
<220> FEATURE:
<223> OTHER INFORMATION: T helper cell epitope

<400> SEQUENCE: 6

Ile Glu Lys Lys Ile Ala Lys Met Glu Lys Ala Ser Ser Val Phe Asn
1               5                   10                  15

Val Val Asn Ser
            20

<210> SEQ ID NO 7
<211> LENGTH: 10
<212> TYPE: PRT
<213> ORGANISM: Artificial Sequence
```

```
<220> FEATURE:
<223> OTHER INFORMATION: FSL-1
<220> FEATURE:
<221> NAME/KEY: BINDING
<222> LOCATION: (1)..(1)
<223> OTHER INFORMATION: S-(2,3-bispalmitoyloxypropyl)

<400> SEQUENCE: 7

Cys Gly Asp Pro Lys His Pro Lys Ser Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: FSL-2
<220> FEATURE:
<221> NAME/KEY: BINDING
<222> LOCATION: (1)..(1)
<223> OTHER INFORMATION: S-(2,3-bispalmitoyloxypropyl)

<400> SEQUENCE: 8

Cys Gly Asp Pro Lys His Pro Lys Ser Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: FSL-3
<220> FEATURE:
<221> NAME/KEY: BINDING
<222> LOCATION: (1)..(1)
<223> OTHER INFORMATION: S-(2,3-bisstearyloxypropyl)

<400> SEQUENCE: 9

Cys Gly Asp Pro Lys His Pro Lys Ser Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: MALP-2
<220> FEATURE:
<221> NAME/KEY: BINDING
<222> LOCATION: (1)..(1)
<223> OTHER INFORMATION: S-(2,3-bispalmitoyloxypropyl)

<400> SEQUENCE: 10

Cys Gly Asn Asn Asp Glu Ser Asn Ile Ser Phe Lys Glu Lys
1               5                   10

<210> SEQ ID NO 11
<211> LENGTH: 5
<212> TYPE: PRT
<213> ORGANISM: Artificial Sequence
<220> FEATURE:
<223> OTHER INFORMATION: C-terminal sequence
<220> FEATURE:
<221> NAME/KEY: MISC_FEATURE
<222> LOCATION: (5)..(5)
<223> OTHER INFORMATION: D-alanine

<400> SEQUENCE: 11

Lys Lys Lys Cys Xaa
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: heptad motif

<400> SEQUENCE: 12

Ile Glu Lys Lys Ile Glu Ala
1               5

<210> SEQ ID NO 13
<211> LENGTH: 7
<212> TYPE: PRT
<213> ORGANISM: Artificial Sequence
<220> FEATURE:
<223> OTHER INFORMATION: heptad motif

<400> SEQUENCE: 13

Ile Glu Lys Lys Ile Glu Ser
1               5

<210> SEQ ID NO 14
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: Maleimido moiety
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (21)..(21)
<223> OTHER INFORMATION: Nle
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 14

Asn Ser Glu Leu Leu Ser Leu Ile Asn Asp Xaa Pro Ile Thr Asn Asp
1               5                   10                  15

Gln Lys Lys Leu Xaa Ser Asn Asn Val Gln Ser Val Arg Xaa
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: AoAc miety incl. a 1-amino-3,6,9,12,15,18-
      hexaoxaheneicosan-21-oic amide linker
<220> FEATURE:
<221> NAME/KEY: MOD_RES
<222> LOCATION: (11)..(11)
<223> OTHER INFORMATION: Nle
```

```
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 15

Asn Ser Glu Leu Leu Ser Leu Cys Asn Asp Xaa Pro Ile Thr Asn Asp
1               5                   10                  15

Gln Lys Lys Leu Cys Ser Asn Xaa Val Gln Ser Val Arg Xaa
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: AoAc moiety incl. 1-amino-3,6,9,12,15,18-
      hexaoxaheneicosan-21-oic amide linker
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 16

Asn Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: AoAc moiety
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
```

```
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 17

Asn Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: Ac moiety
<220> FEATURE:
<221> NAME/KEY: MOD_RES
<222> LOCATION: (11)..(11)
<223> OTHER INFORMATION: Nle
<220> FEATURE:
<221> NAME/KEY: BINDING
<222> LOCATION: (24)..(24)
<223> OTHER INFORMATION: AOAc moiety
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 18

Asn Ser Glu Cys Leu Ser Leu Cys Asn Asp Xaa Pro Ile Thr Asn Asp
1               5                   10                  15

Gln Lys Lys Leu Cys Ser Asn Lys Cys Gln Ser Val Arg Xaa
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: AOAc
<220> FEATURE:
<221> NAME/KEY: MOD_RES
<222> LOCATION: (12)..(12)
<223> OTHER INFORMATION: Nle
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 19

Arg Leu Ser Glu Cys Leu Ser Leu Cys Asn Asp Xaa Pro Ile Thr Asn
1               5                   10                  15
```

```
Asp Gln Lys Lys Leu Cys Ser Asn Asn Cys Leu Lys Ser Xaa
            20                  25                  30

<210> SEQ ID NO 20
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: AOAc
<220> FEATURE:
<221> NAME/KEY: MISC_FEATURE
<222> LOCATION: (40)..(40)
<223> OTHER INFORMATION: D-alanine
<220> FEATURE:
<221> NAME/KEY: MOD_RES
<222> LOCATION: (40)..(40)
<223> OTHER INFORMATION: AMIDATION

<400> SEQUENCE: 20

Pro Val Ser Thr Tyr Met Leu Thr Asn Ser Glu Cys Leu Ser Leu Cys
1               5                   10                  15

Asn Asp Met Pro Ile Thr Asn Asp Gln Lys Lys Leu Cys Ser Asn Asn
            20                  25                  30

Cys Gln Ile Val Arg Gln Gln Xaa
        35                  40

<210> SEQ ID NO 21
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 21

Asn Ser Glu Cys Leu Ser Leu Cys Asn Asp Xaa Pro Ile Thr Asn Asp
1               5                   10                  15

Gln Lys Lys Leu Cys Ser Asn Asn Cys Gln Ser Val Arg Xaa
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 22

Asn Ser Glu Cys Leu Ser Leu Cys Asn Asp Xaa Pro Ile Thr Asn Asp
1               5                   10                  15
```

```
Gln Lys Lys Leu Cys Ser Asn Asp Cys Gln Ser Val Arg Xaa
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Orn
<220> FEATURE:
<221> NAME/KEY: MISC_FEATURE
<222> LOCATION: (30)..(30)
<223> OTHER INFORMATION: D-alanine

<400> SEQUENCE: 23

Asn Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 24

Arg Leu Ser Glu Cys Leu Ser Leu Cys Asn Asp Xaa Pro Ile Thr Asn
1               5                   10                  15

Asp Gln Lys Lys Leu Cys Ser Asn Lys Cys Leu Lys Ser Xaa
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: Nle
<220> FEATURE:
<221> NAME/KEY: MOD_RES
<222> LOCATION: (25)..(25)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 25

Arg Leu Ser Glu Cys Leu Ser Leu Cys Asn Asp Xaa Pro Ile Thr Asn
```

```
                1               5                  10                 15
Asp Gln Lys Lys Leu Cys Ser Asn Xaa Cys Leu Lys Ser Xaa
            20                  25                 30

<210> SEQ ID NO 26
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (40)..(40)
<223> OTHER INFORMATION: D-alanine

<400> SEQUENCE: 26

Pro Val Ser Thr Tyr Met Leu Thr Asn Ser Glu Cys Leu Ser Leu Cys
1               5                   10                  15

Asn Asp Met Pro Ile Thr Asn Asp Gln Lys Lys Leu Cys Ser Asn Lys
            20                  25                  30

Cys Gln Ile Val Arg Gln Gln Xaa
            35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (32)..(32)
<223> OTHER INFORMATION: Dbu
<220> FEATURE:
<221> NAME/KEY: MISC_FEATURE
<222> LOCATION: (40)..(40)
<223> OTHER INFORMATION: D-alanine

<400> SEQUENCE: 27

Pro Val Ser Thr Tyr Met Leu Thr Asn Ser Glu Cys Leu Ser Leu Cys
1               5                   10                  15

Asn Asp Met Pro Ile Thr Asn Asp Gln Lys Lys Leu Cys Ser Asn Xaa
            20                  25                  30

Cys Gln Ile Val Arg Gln Gln Xaa
            35                  40

<210> SEQ ID NO 28
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 28

Arg Leu Ser Glu Cys Leu Ser Leu Cys Asn Asp Xaa Pro Ile Thr Asn
1               5                   10                  15

Asp Gln Lys Lys Leu Cys Ser Asn Asp Cys Leu Lys Ser Xaa
            20                  25                  30
```

```
<210> SEQ ID NO 29
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (12)..(12)
<223> OTHER INFORMATION: Nle
<220> FEATURE:
<221> NAME/KEY: MOD_RES
<222> LOCATION: (25)..(25)
<223> OTHER INFORMATION: Orn
<220> FEATURE:
<221> NAME/KEY: MISC_FEATURE
<222> LOCATION: (30)..(30)
<223> OTHER INFORMATION: D-alanine

<400> SEQUENCE: 29

Arg Leu Ser Glu Cys Leu Ser Leu Cys Asn Asp Xaa Pro Ile Thr Asn
1               5                   10                  15

Asp Gln Lys Lys Leu Cys Ser Asn Xaa Cys Leu Lys Ser Xaa
            20                  25                  30

<210> SEQ ID NO 30
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (40)..(40)
<223> OTHER INFORMATION: D-alanine

<400> SEQUENCE: 30

Pro Val Ser Thr Tyr Met Leu Thr Asn Ser Glu Cys Leu Ser Leu Cys
1               5                   10                  15

Asn Asp Met Pro Ile Thr Asn Asp Gln Lys Lys Leu Cys Ser Asn Asp
            20                  25                  30

Cys Gln Ile Val Arg Gln Gln Xaa
        35                  40

<210> SEQ ID NO 31
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (32)..(32)
<223> OTHER INFORMATION: Orn
<220> FEATURE:
<221> NAME/KEY: MISC_FEATURE
<222> LOCATION: (40)..(40)
<223> OTHER INFORMATION: D-alanine

<400> SEQUENCE: 31

Pro Val Ser Thr Tyr Met Leu Thr Asn Ser Glu Cys Leu Ser Leu Cys
1               5                   10                  15

Asn Asp Met Pro Ile Thr Asn Asp Gln Lys Lys Leu Cys Ser Asn Xaa
            20                  25                  30

Cys Gln Ile Val Arg Gln Gln Xaa
        35                  40
```

```
<210> SEQ ID NO 32
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (19)..(19)
<223> OTHER INFORMATION: Nle
<220> FEATURE:
<221> NAME/KEY: MISC_FEATURE
<222> LOCATION: (40)..(40)
<223> OTHER INFORMATION: D-alanine

<400> SEQUENCE: 32

Pro Val Ser Thr Tyr Met Leu Thr Asn Ser Glu Cys Leu Ser Leu Cys
1               5                   10                  15

Asn Asp Xaa Pro Ile Thr Asn Asp Gln Lys Lys Leu Cys Ser Asn Asn
            20                  25                  30

Cys Gln Ile Val Arg Gln Gln Xaa
        35                  40

<210> SEQ ID NO 33
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (19)..(19)
<223> OTHER INFORMATION: Nle
<220> FEATURE:
<221> NAME/KEY: MISC_FEATURE
<222> LOCATION: (40)..(40)
<223> OTHER INFORMATION: X-alanine

<400> SEQUENCE: 33

Pro Val Ser Thr Tyr Met Leu Thr Asn Ser Glu Cys Leu Ser Leu Cys
1               5                   10                  15

Asn Asp Xaa Pro Ile Thr Asn Asp Gln Lys Lys Leu Cys Ser Asn Lys
            20                  25                  30

Cys Gln Ile Val Arg Gln Gln Xaa
        35                  40

<210> SEQ ID NO 34
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (19)..(19)
<223> OTHER INFORMATION: Nle
<220> FEATURE:
<221> NAME/KEY: MOD_RES
<222> LOCATION: (32)..(32)
<223> OTHER INFORMATION: Dbu
<220> FEATURE:
<221> NAME/KEY: MISC_FEATURE
<222> LOCATION: (40)..(40)
<223> OTHER INFORMATION: D-alanine

<400> SEQUENCE: 34

Pro Val Ser Thr Tyr Met Leu Thr Asn Ser Glu Cys Leu Ser Leu Cys
1               5                   10                  15

Asn Asp Xaa Pro Ile Thr Asn Asp Gln Lys Lys Leu Cys Ser Asn Xaa
```

```
Cys Gln Ile Val Arg Gln Gln Xaa
        35                  40

<210> SEQ ID NO 35
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (19)..(19)
<223> OTHER INFORMATION: Nle
<220> FEATURE:
<221> NAME/KEY: MISC_FEATURE
<222> LOCATION: (40)..(40)
<223> OTHER INFORMATION: D-alanine

<400> SEQUENCE: 35

Pro Val Ser Thr Tyr Met Leu Thr Asn Ser Glu Cys Leu Ser Leu Cys
1               5                   10                  15

Asn Asp Xaa Pro Ile Thr Asn Asp Gln Lys Lys Leu Cys Ser Asn Asp
            20                  25                  30

Cys Gln Ile Val Arg Gln Gln Xaa
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (19)..(19)
<223> OTHER INFORMATION: Nle
<220> FEATURE:
<221> NAME/KEY: MOD_RES
<222> LOCATION: (32)..(32)
<223> OTHER INFORMATION: Dbu
<220> FEATURE:
<221> NAME/KEY: MOD_RES
<222> LOCATION: (32)..(32)
<223> OTHER INFORMATION: orn
<220> FEATURE:
<221> NAME/KEY: MISC_FEATURE
<222> LOCATION: (40)..(40)
<223> OTHER INFORMATION: D-alanine

<400> SEQUENCE: 36

Pro Val Ser Thr Tyr Met Leu Thr Asn Ser Glu Cys Leu Ser Leu Cys
1               5                   10                  15

Asn Asp Xaa Pro Ile Thr Asn Asp Gln Lys Lys Leu Cys Ser Asn Xaa
            20                  25                  30

Cys Gln Ile Val Arg Gln Gln Xaa
        35                  40

<210> SEQ ID NO 37
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
```

-continued

```
<221> NAME/KEY: MOD_RES
<222> LOCATION: (21)..(21)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 37

Asn Ser Glu Leu Leu Ser Leu Ile Asn Asp Xaa Pro Ile Thr Asn Asp
1               5                   10                  15

Gln Lys Lys Leu Xaa Ser Asn Asn Val Gln Ser Val Arg Xaa
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 38

Asn Ser Glu Leu Leu Ser Leu Cys Asn Asp Xaa Pro Ile Thr Asn Asp
1               5                   10                  15

Gln Lys Lys Leu Cys Ser Asn Xaa Val Gln Ser Val Arg Xaa
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 39

Asn Ser Glu Cys Leu Ser Leu Cys Asn Asp Xaa Pro Ile Thr Asn Asp
1               5                   10                  15

Gln Lys Lys Leu Cys Ser Ser Xaa Cys Gln Ser Val Arg Xaa
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic
```

<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 40

Asn Ser Glu Cys Leu Ser Leu Cys Asn Asp Xaa Pro Ile Thr Asn Asp
1               5                   10                  15

Gln Lys Lys Leu Cys Ser Ser Asn Cys Gln Ser Val Arg Xaa
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 41

Asn Ser Glu Cys Leu Ser Leu Cys Asn Asp Xaa Pro Ile Thr Asn Asp
1               5                   10                  15

Gln Lys Lys Leu Cys Ser Ser Gln Cys Gln Ser Val Arg Xaa
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (30)..(30)
<223> OTHER INFORMATION: AMIDATION
<220> FEATURE:
<221> NAME/KEY: MISC_FEATURE
<222> LOCATION: (30)..(30)
<223> OTHER INFORMATION: D-alanine

<400> SEQUENCE: 42

Asn Ser Glu Cys Leu Ser Leu Cys Asn Asp Xaa Pro Ile Thr Asn Asp
1               5                   10                  15

Gln Lys Lys Leu Cys Ser Ser Ser Cys Gln Ser Val Arg Xaa
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)

```
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 43

Gln Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 44

Gln Ser Glu Cys Leu Ser Leu Cys Asn Asp Xaa Pro Ile Thr Asn Asp
1               5                   10                  15

Gln Lys Lys Leu Cys Ser Ser Xaa Cys Gln Ser Val Arg Xaa
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 45

Gln Ser Glu Cys Leu Ser Leu Cys Asn Asp Xaa Pro Ile Thr Asn Asp
1               5                   10                  15

Gln Lys Lys Leu Cys Ser Ser Asn Cys Gln Ser Val Arg Xaa
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
```

```
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 46

Gln Ser Glu Cys Leu Ser Leu Cys Asn Asp Xaa Pro Ile Thr Asn Asp
1               5                   10                  15

Gln Lys Lys Leu Cys Ser Ser Gln Cys Gln Ser Val Arg Xaa
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 47

Gln Ser Glu Cys Leu Ser Leu Cys Asn Asp Xaa Pro Ile Thr Asn Asp
1               5                   10                  15

Gln Lys Lys Leu Cys Ser Ser Ser Cys Gln Ser Val Arg Xaa
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 48

Ser Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
```

```
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 49

Ser Ser Glu Cys Leu Ser Leu Cys Asn Asp Xaa Pro Ile Thr Asn Asp
1               5                   10                  15

Gln Lys Lys Leu Cys Ser Ser Xaa Cys Gln Ser Val Arg Xaa
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 50

Ser Ser Glu Cys Leu Ser Leu Cys Asn Asp Xaa Pro Ile Thr Asn Asp
1               5                   10                  15

Gln Lys Lys Leu Cys Ser Ser Asn Cys Gln Ser Val Arg Xaa
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 51

Ser Ser Glu Cys Leu Ser Leu Cys Asn Asp Xaa Pro Ile Thr Asn Asp
1               5                   10                  15

Gln Lys Lys Leu Cys Ser Ser Gln Cys Gln Ser Val Arg Xaa
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine
```

<400> SEQUENCE: 52

Ser Ser Glu Cys Leu Ser Leu Cys Asn Asp Xaa Pro Ile Thr Asn Asp
1               5                   10                  15

Gln Lys Lys Leu Cys Ser Ser Ser Cys Gln Ser Val Arg Xaa
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 53

Gly Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine

<400> SEQUENCE: 54

Gly Ser Glu Cys Leu Ser Leu Cys Asn Asp Xaa Pro Ile Thr Asn Asp
1               5                   10                  15

Gln Lys Lys Leu Cys Ser Ser Xaa Cys Gln Ser Val Arg Xaa
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)

<223> OTHER INFORMATION: D-alanine

<400> SEQUENCE: 55

Gly Ser Glu Cys Leu Ser Leu Cys Asn Asp Xaa Pro Ile Thr Asn Asp
1               5                   10                  15

Gln Lys Lys Leu Cys Ser Ser Asn Cys Gln Ser Val Arg Xaa
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 56

Gly Ser Glu Cys Leu Ser Leu Cys Asn Asp Xaa Pro Ile Thr Asn Asp
1               5                   10                  15

Gln Lys Lys Leu Cys Ser Ser Gln Cys Gln Ser Val Arg Xaa
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (30)..(30)
<223> OTHER INFORMATION: D-alanine

<400> SEQUENCE: 57

Gly Ser Glu Cys Leu Ser Leu Cys Asn Asp Xaa Pro Ile Thr Asn Asp
1               5                   10                  15

Gln Lys Lys Leu Cys Ser Ser Ser Cys Gln Ser Val Arg Xaa
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (1)..(1)
<223> OTHER INFORMATION: linker
<220> FEATURE:
<221> NAME/KEY: DISULFID
<222> LOCATION: (4)..(25)
<220> FEATURE:
<221> NAME/KEY: DISULFID
<222> LOCATION: (8)..(21)

```
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 58

Asn Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 59
<211> LENGTH: 55
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: lipid moiety
<220> FEATURE:
<221> NAME/KEY: BINDING
<222> LOCATION: (54)..(54)
<223> OTHER INFORMATION: linker
<220> FEATURE:
<221> NAME/KEY: MISC_FEATURE
<222> LOCATION: (55)..(55)
<223> OTHER INFORMATION: D-alanine
<220> FEATURE:
<221> NAME/KEY: MOD_RES
<222> LOCATION: (55)..(55)
<223> OTHER INFORMATION: AMIDATION

<400> SEQUENCE: 59

Gly Gly Ile Glu Lys Lys Ile Glu Ser Ile Glu Lys Lys Ile Glu Ser
1               5                   10                  15

Ile Glu Lys Lys Ile Glu Ser Ile Glu Lys Lys Ile Glu Ser Ile Glu
            20                  25                  30

Lys Lys Ile Ala Lys Met Glu Lys Ala Ser Ser Val Phe Asn Val Val
        35                  40                  45

Asn Ser Lys Lys Lys Cys Xaa
    50                  55

<210> SEQ ID NO 60
<211> LENGTH: 55
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: lipid moiety
<220> FEATURE:
<221> NAME/KEY: BINDING
<222> LOCATION: (54)..(54)
<223> OTHER INFORMATION: linker
<220> FEATURE:
```

```
<221> NAME/KEY: MOD_RES
<222> LOCATION: (55)..(55)
<223> OTHER INFORMATION: AMIDATION
<220> FEATURE:
<221> NAME/KEY: MISC_FEATURE
<222> LOCATION: (55)..(55)
<223> OTHER INFORMATION: D-alanine

<400> SEQUENCE: 60

Gly Gly Ile Glu Lys Lys Ile Glu Ala Ile Glu Lys Lys Ile Glu Ala
1               5                   10                  15

Ile Glu Lys Lys Ile Glu Ala Ile Glu Lys Lys Ile Glu Ala Ile Glu
            20                  25                  30

Lys Lys Ile Ala Lys Met Glu Lys Ala Ser Ser Val Phe Asn Val Val
            35                  40                  45

Asn Ser Lys Lys Lys Cys Xaa
        50                  55

<210> SEQ ID NO 61
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: linker
<220> FEATURE:
<221> NAME/KEY: DISULFID
<222> LOCATION: (4)..(25)
<220> FEATURE:
<221> NAME/KEY: DISULFID
<222> LOCATION: (8)..(24)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MOD_RES
<222> LOCATION: (30)..(30)
<223> OTHER INFORMATION: AMIDATION
<220> FEATURE:
<221> NAME/KEY: MISC_FEATURE
<222> LOCATION: (30)..(30)
<223> OTHER INFORMATION: D-alanine

<400> SEQUENCE: 61

Asn Ser Glu Cys Leu Ser Leu Cys Asn Asp Xaa Pro Ile Thr Asn Asp
1               5                   10                  15

Gln Lys Lys Leu Cys Ser Asn Xaa Cys Gln Ser Val Arg Xaa
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (4)..(21)
<220> FEATURE:
```

```
<221> NAME/KEY: DISULFID
<222> LOCATION: (8)..(25)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: ACETYLATION
<220> FEATURE:
<221> NAME/KEY: BINDING
<222> LOCATION: (24)..(24)
<223> OTHER INFORMATION: linker
<220> FEATURE:
<221> NAME/KEY: MOD_RES
<222> LOCATION: (30)..(30)
<223> OTHER INFORMATION: AMIDATION
<220> FEATURE:
<221> NAME/KEY: MISC_FEATURE
<222> LOCATION: (30)..(30)
<223> OTHER INFORMATION: D-alanine

<400> SEQUENCE: 62

Asn Ser Glu Cys Leu Ser Leu Cys Asn Asp Xaa Pro Ile Thr Asn Asp
1               5                   10                  15

Gln Lys Lys Leu Cys Ser Asn Lys Cys Gln Ser Val Arg Xaa
            20                  25                  30

<210> SEQ ID NO 63
<211> LENGTH: 55
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: lipid moiety
<220> FEATURE:
<221> NAME/KEY: MISC_FEATURE
<222> LOCATION: (55)..(55)
<223> OTHER INFORMATION: D-alanine
<220> FEATURE:
<221> NAME/KEY: MOD_RES
<222> LOCATION: (55)..(55)
<223> OTHER INFORMATION: AMIDATION

<400> SEQUENCE: 63

Gly Gly Ile Glu Lys Lys Ile Glu Ala Ile Glu Lys Lys Ile Glu Ala
1               5                   10                  15

Ile Glu Lys Lys Ile Glu Ala Ile Glu Lys Lys Ile Glu Ala Ile Glu
            20                  25                  30

Lys Lys Ile Ala Lys Met Glu Lys Ala Ser Ser Val Phe Asn Val Val
        35                  40                  45

Asn Ser Lys Lys Lys Cys Xaa
        50                  55

<210> SEQ ID NO 64
<211> LENGTH: 55
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: linker
<220> FEATURE:
<221> NAME/KEY: MISC_FEATURE
<222> LOCATION: (55)..(55)
```

```
<223> OTHER INFORMATION: D-alanine
<220> FEATURE:
<221> NAME/KEY: MOD_RES
<222> LOCATION: (55)..(55)
<223> OTHER INFORMATION: AMIDATION

<400> SEQUENCE: 64

Gly Gly Ile Glu Lys Lys Ile Glu Ser Ile Glu Lys Lys Ile Glu Ser
1               5                   10                  15

Ile Glu Lys Lys Ile Glu Ser Ile Glu Lys Lys Ile Glu Ser Ile Glu
            20                  25                  30

Lys Lys Ile Ala Lys Met Glu Lys Ala Ser Ser Val Phe Asn Val Val
        35                  40                  45

Asn Ser Lys Lys Lys Cys Xaa
    50                  55

<210> SEQ ID NO 65
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: linker
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (21)..(21)
<223> OTHER INFORMATION: Nle
<220> FEATURE:
<221> NAME/KEY: MISC_FEATURE
<222> LOCATION: (30)..(30)
<223> OTHER INFORMATION: D-alanine
<220> FEATURE:
<221> NAME/KEY: MOD_RES
<222> LOCATION: (30)..(30)
<223> OTHER INFORMATION: AMIDATION

<400> SEQUENCE: 65

Asn Ser Glu Leu Leu Ser Leu Ile Asn Asp Xaa Pro Ile Thr Asn Asp
1               5                   10                  15

Gln Lys Lys Leu Xaa Ser Asn Asn Val Gln Ser Val Arg Xaa
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: Synthetic sequence
<220> FEATURE:
<221> NAME/KEY: BINDING
<222> LOCATION: (1)..(1)
<223> OTHER INFORMATION: linker
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (24)..(24)
<223> OTHER INFORMATION: Dbu
<220> FEATURE:
<221> NAME/KEY: MOD_RES
<222> LOCATION: (30)..(30)
<223> OTHER INFORMATION: AMIDATION
```

```
<220> FEATURE:
<221> NAME/KEY: MISC_FEATURE
<222> LOCATION: (30)..(30)
<223> OTHER INFORMATION: D-alaine

<400> SEQUENCE: 66

Asn Ser Glu Leu Leu Ser Leu Cys Asn Asp Xaa Pro Ile Thr Asn Asp
1               5                   10                  15

Gln Lys Lys Leu Cys Ser Asn Xaa Val Gln Ser Val Arg Xaa
            20                  25                  30
```

CYCLIC PEPTIDES FOR PROTECTION AGAINST RESPIRATORY SYNCYTIAL VIRUS

REFERENCE TO AN ELECTRONIC SEQUENCE LISTING

The contents of the electronic sequence listing (0192-0101US1_SL.txt; Size: 36,344 bytes; and Date of Creation Nov. 10, 2021) is herein incorporated by reference in its entirety.

The present invention relates to a cyclic peptide, a conjugate comprising said cyclic peptide and a lipopeptide building block, a bundle of said conjugates, a synthetic virus-like particle comprising at least one bundle of conjugates and pharmaceutical compositions comprising the same. The present invention further relates to said cyclic peptide, said conjugate said bundle of conjugates, said synthetic virus-like particle and said pharmaceutical compositions for use as a medicament, preferably for use in a method for preventing of an infectious disease or reducing the risk of an infectious disease, more preferably for use in a method for preventing or reducing the risk of an infectious disease associated with or caused by a respiratory syncytial virus.

RELATED ART

Human respiratory syncytial virus (RSV) is a member of the virus family Pneumoviridae and a highly contagious seasonal respiratory virus that infects the lungs and breathing passages. It can spread via droplets sneezed or coughed into the air by an infected person. In particular, RSV is a main cause of lower and upper respiratory tract infections and hospital visits in particular during infancy and childhood but affects older adults and immunocompromised persons as well. In children younger than 1 year of age, RSV is the most common cause of bronchiolitis, an inflammation of the small airways in the lung, and pneumonia, an infection of the lungs (National Center for Immunization and Respiratory Diseases (NCIRD), Division of Viral Diseases, cdc.gov/rsv/about/infection.html, Nov. 4, 2014). Moreover, RSV is a major cause of respiratory illness in elderly. The immune response elicited after natural RSV infection is short-lived and does not protect hosts from future re-infection(s) (Johnson, K. M. et al., N Engl J Med, 1962, vol. 267, 68-72).

Current RSV treatment options are limited to humidified oxygen and Ribavirin. Both approaches have drawbacks: (1) Oxygen treatment requires significant supportive care and respiratory assistance, which makes the treatment expensive. (2) Ribavirin requires long aerosol administration and is teratogenic, in particular, posing a safety risk for pregnant and breastfeeding women.

Due to high health costs associated with hospitalizations caused by RSV infections, there is a need for prophylaxis of RSV infections. Neutralizing antibodies to the RSV-F protein are known to be protective in children. The humanized monoclonal antibody Palivizumab (Synagis®) is an RSV-F specific neutralizing and prophylactic antibody approved for use in infants at risk of severe infection, such as preterm babies or children with congenital heart disease. Palivizumab antibody blocks both cell-to-cell and virus-to-cell fusion (Huang, K. et al., J. Virol., 2010, 16, 8132-40), and may prevent syncytia formation. However, due to its short half-life, multiple intramuscular doses of 15 mg/kg are required during the RSV season to achieve a prophylactic effect. This inconvenience increases the costs of RSV prophylaxis and bears the risk of missed doses due to missed visits at the doctor. In addition, the manufacturing of Synagis® is very expensive, its scalability is limited, and Synagis® is not approved for adults or general pediatric use.

An alternative approach is active immunization by an RSV vaccine. However, to date, attempts to produce a vaccine have been not promising due to safety issues and/or low efficacy. For example, immunization with a formalin inactivated vaccine was found to cause severely enhanced disease in a phase III trial in infants in the 1960s (Chin, J. et al., Am J. Epidemiol., 1969, 89, 449-463; Kim, H. W. et al., Am. J. Epidemiol., 1969, 89, 422-434; Kapikian, A. Z. et al., Am. J. Epidemiol., 1969, 89, 405-421). This enhancement appears to be related to imbalanced cell-mediated immune responses (Chang, J., BMB Rep., 2011, 44, 232-237).

In further approaches, RSV vaccines have been tested that should have induced antibodies similar to Synagis® in a patient. For this purpose, scaffold proteins and VLPs have been developed that display the Palivizumab epitope on their surface (WO 2014/144756, WO 2012/048115). However, these approaches did not elicit adequate titers of neutralizing antibodies and/or required very strong adjuvants not approved for human use.

Furthermore, attempts have been made to develop modified recombinant F-protein-based peptides or RSV vaccines (WO 2006/034292, US 2010/0239617, WO 2010/149745). For example, modifications have been introduced to increase the expression by deleting amino acids and inactivating a furin cleavage site (US 2010/0239617). Another approach aimed to stabilize F-protein in a more effective pre-fusion conformation by altering F-protein glycosylation (WO 2010/149745).

However, none of the candidates evaluated to date have been approved as safe and effective vaccine for the purpose of preventing RSV infections. For this reasons, there exists a great necessity for addressing such an unmet medical need, and further for identification of improved prophylactic approaches that can reduce costs of RSV vaccination and allow addressing a broader pediatric and adult population.

SUMMARY OF THE INVENTION

We have now surprisingly identified a specific family of cyclic peptides that, when coupled to synthetic virus-like particles (SVLPs), elicit neutralizing and protective antibodies against the RSV virus without administration of an adjuvant. The cyclic peptides of the invention are capable of mimicking the Palivizumab antigenic peptide (antigenic site II) from the Respiratory Syncytial Virus F protein (RSV-F) and, after administration, induces production of potent neutralizing RSV antibodies, as shown in in vivo experiments. Thus, mice immunized with SVLPs carrying the cyclic peptides of the invention are protected against lung RSV replication in challenge experiments. In addition, SVLPs carrying the cyclic peptides of the invention elicited anti-RSV neutralizing antibodies in mice and rabbits. Thus, said cyclic peptides represent promising leads for the research and development of a human respiratory syncytial virus vaccine in order to protect a broad population, including infants, young children and elderly against an RSV infection.

In the cyclic peptides of the invention, the specific disulfide bridges between cysteines C4 and C25 and cysteines C8 and C21 stabilize said peptides by a "helical hairpin" or "helix-turn-helix" conformation and provide also biological activity. The cyclic peptides of the invention may thus overcome efficacy problems in vaccination observed when whole virus or protein based RSV vaccines are used. Notably, peptides with no or only one disulfide bridge or with disulfide bridges at different positions failed to elicit neutralizing antibodies.

Moreover, the inventive cyclic peptides are promising RSV antigens that may lead to well-tolerated vaccines. An undesired side effect frequently accompanying vaccination against respiratory infections is a phenomenon called "vaccine associated enhanced respiratory disease" (VAERD). In this adverse reaction, clinical signs of the respiratory disease are exacerbated and disease severity is increased. However, immune responses elicited by the cyclic peptides of the invention coupled to SVLPs did not activate VAERD after life RSV infection. The cyclic peptides of the present invention did not show any evidence for potential disease enhancement in rodent models and thus their use as a safe vaccine is suggested.

Finally, the cyclic peptides of the invention can be produced cost-effectively, whereby an affordable vaccination approach can be provided to the broader population.

Thus, in a first aspect, the present invention provides for a cyclic peptide, wherein said cyclic peptide comprises an amino acid sequence (I), wherein said amino acid sequence (I) comprises the following amino acid sequence:

X1-X2-X3-C4-X5-X6-X7-C8-X9-X10-X11-P12-I13-
T14-N15-D16-Q17-K18-K19-L20-C21-X22-
X23-X24-C25-X26-X27-
X28-X29-X30  (SEQ ID NO: 1), wherein X1, X2, X3, X5, X6, X7, X9, X10, X11, X22, X23, X24, X26, X27, X28 and X29 are independently of each other an amino acid;
C4, C8, C21 and C25 are independently of each other cysteine;
P12 is proline;
I13 is isoleucine;
T14 is threonine;
N15 is asparagine;
D16 is aspartic acid;
Q17 is glutamine;
K18 and K19 are independently of each other lysine;
L20 is leucine; and
X30 is an amino acid or a deletion,
wherein said cysteines C4 and C25 form a first disulfide bond and said cysteines C8 and C21 form a second disulfide bond.

In a second aspect, the present invention provides a conjugate comprising (a) a lipopeptide building block, and (b) a cyclic peptide, wherein said lipopeptide building block consists of (i) a peptide moiety comprising at least one coiled coil peptide chain segment, and (ii) a lipid moiety comprising two or three, preferably two hydrocarbyl chains; and wherein said cyclic peptide is connected, directly or via a linker, to said lipopeptide building block, and wherein said cyclic peptide comprises an amino acid sequence (I), wherein said amino acid sequence (I) comprises, preferably consists of, the amino acid sequence:

X1-X2-X3-C4-X5-X6-X7-C8-X9-X10-X11-P12-I13-
T14-N15-D16-Q17-K18-K19-L20-C21-X22-
X23-X24-C25-X26-X27-
X28-X29-X30  (SEQ ID NO: 1), wherein X1, X2, X3, X5, X6, X7, X9, X10, X11, X22, X23, X24, X26, X27, X28 and X29 are independently of each other an amino acid; C4, C8, C21 and C25 are independently of each other cysteine; P12 is proline; I13 is isoleucine; T14 is threonine; N15 is asparagine; D16 is aspartic acid; Q17 is glutamine; K18 and K19 are independently of each other lysine; L20 is leucine; and X30 is an amino acid or a deletion,
wherein said cysteines C4 and C25 form a first disulfide bond and said cysteines C8 and C21 form a second disulfide bond.

In another aspect, the present invention provides for a bundle of conjugates comprising 2, 3, 4, 5, 6 or 7, preferably 2, 3, 4 or 5, more preferably 3, of the inventive conjugate.

In a further aspect, the present invention provides for a synthetic virus-like particle comprising the cyclic peptide of the present invention.

In another aspect, the present invention provides for a synthetic virus-like particle comprising at least one bundle of conjugates of the present invention.

In another aspect, the present invention provides for a pharmaceutical composition comprising an immunologically effective amount of the cyclic peptide of the present invention, the conjugate of the present invention or the synthetic virus like particle of the present invention, together with a pharmaceutically acceptable diluent, carrier or excipient, wherein preferably said pharmaceutical composition is a vaccine.

In again another aspect, the present invention provides for the cyclic peptide of the present invention, the conjugate of the present invention or the synthetic virus like particle of the present invention for use as a medicament.

In again another aspect, the present invention provides for the cyclic peptide of the present invention, the conjugate of the present invention or the synthetic virus like particle of the present invention for use in a method for preventing of an infectious disease or reducing the risk of an infectious disease, preferably for use in a method for preventing or reducing the risk of an infectious disease associated with or caused by a respiratory syncytial virus.

Further aspects and embodiments of the present invention will become apparent as this description continues.

DETAILED DESCRIPTION OF THE INVENTION

Unless defined otherwise, all technical and scientific terms used herein have the same meaning as commonly understood by one of ordinary skill in the art to which this invention belongs.

Throughout this specification and the claims, which follow, unless the context requires otherwise, the term "comprise" and its variations such as "comprises" and "comprising" etc., are to be understood as a non-exhaustive wording and imply the inclusion of a stated feature or element but not the exclusion of any other feature or element. The term "comprise" and its variations cover the term "consisting of". As used in this specification and the appended claims, the singular forms "a", "an", and "the" include plural referents, unless the content clearly dictates otherwise. The terms "reduce", "inhibit" or "decrease", as used herein, include a just detectable reduction but also a reduction down to zero (reduction by 100%).

A peptide or peptide moiety, as defined herein, is any peptide-bond-linked chain of amino acids, regardless of length, secondary and tertiary structure, number of subunits or post-translational modification. Thus, the term "peptide" is to be understood as covering the terms "polypeptide", "protein", "amino acid chain" and "polypeptide chain". Amino acids included in the peptide of the invention are proteinogenic, non-proteinogenic and synthetic amino acids. Peptides in accordance with the invention can be an open linear peptide chain or cyclic peptides; alternatively or additionally, peptides of the invention may include at least one chemical modification, such as lipidation, glycosylation and phosphorylation. Peptides, as understood herein, especially peptides of the invention, are isolated or, preferably can be produced by chemical synthesis, RNA translation and/or recombinant processes. Preferably, the peptide of the invention is a chemically synthesized peptide.

The term "cyclic peptide", as used herein, refers to a peptide in which the amino acid chain forms at least one ring structure by a covalent bond. The cyclic peptide of the invention comprises two ring structures each formed by a disulfide bond: Side chains of cysteines C4 and C25 are linked forming a first disulfide bond, and side chains of cysteines C8 and C21 are linked forming a second disulfide bond.

The term "amino acid", as used herein, refers to organic compounds containing the functional groups amine (—NH2) and carboxylic acid (—COOH) and its zwitterions, typically and preferably, along with a side chain specific to each amino acid. The term "amino acid" typically and preferably includes amino acids that occur naturally, such as proteinogenic amino acids (produced by RNA-translation), non-proteinogenic amino acids (produced by other metabolic mechanisms, e.g. posttranslational modification), standard or canonical amino acids (that are directly encoded by the codons of the genetic code) and non-standard or non-canonical amino acids (not directly encoded by the genetic code). Naturally occurring amino acids include non-eukaryotic and eukaryotic amino acids.

The term "amino acid", as used herein, also includes unnatural amino acids that are chemically synthesized; alpha-($\alpha$-), beta- ($\beta$-), gamma- ($\gamma$-) and delta- ($\delta$-) etc. amino acids as well as mixtures thereof in any ratio; and, if applicable, any isomeric form of an amino acid, i.e. its D-stereoisomers (labelled with a lower-case initial letter) and L-stereoisomers (labelled with a capital initial letter) (alternatively addressed by the (R) and (S) nomenclature) as well as mixtures thereof in any ratio, preferably in a racemic ratio of 1:1. Amino acids in this invention are preferably in L-configuration, unless mentioned specifically as D-configuration. The term "D-stereoisomer", "L-stereoisomer", "D-amino acid" or "L-amino acid" refers to the chiral alpha carbon of the amino acids. Amino acid can include one or more modifications and/or attached groups, for example protecting groups used for peptide synthesis, such as Boc, Fmoc or both. The term "deletion" refers herein to a position in an amino acid sequence that is not occupied by an amino acid.

The term "N-terminus", as used herein, refers to an end of a peptide having a free (—NH$_2$) or modified amino or amine group. Preferred N-terminal modifications are those that protect the N-terminus from proteolytic degradation. N-terminal modifications in accordance with the invention include but are not limited to acetylation, attachment of at least one polymer, preferably polyethylene glycol (PEGylation) or poly(lactic acid), or attachment of at least one amino acid, preferably of at least one D-amino acid, or attachment of at least one compound, such as a cell penetrating peptide, nucleic acid, a carbamate, such as fluorenylmethoxycarbamate or benzyloxy carbamate, aldehyde, hydrazinonicotinic acid, 4-formyl benzamide, methyl, myristoyl, prenyl group, palmitoyl, ubiquitin, 7-methoxycoumarin acetic acid (Mca), dansyl, formyl, 4-diniphenyl, pyroglutamyl, urea, carbamate, sulphonamide, alkylamine, fatty acids, such as palmitic acids, radioligand, quencher, fluorescein or another dye or label such as biotin.

The term "C-terminus", as used herein, refers to an end of a peptide having a free (—COOH) or modified carboxyl group. Preferred C-terminal modifications are those that protect the C-terminus from proteolytic degradation. C-terminal modifications in accordance with the invention include but are not limited to amidation or attachment of at least one amino acid, preferably of at least one D-amino acid, or attachment of at least one compound, such as a cell penetrating peptide, nucleic acid, polyethylene glycol (PEGylation), thiol, ester, aldehyde, sulphonamide, pNA (para-nitroanilide), Amc (7-amino-4-methylcoumarinyl), hydrazide, hydroxamic acid, chloromethyl ketone, biotin, radioligand, quencher, Abz or other dyes and labels. Herein and by general convention, peptide sequences are written from N-terminal on the left to C-terminal on the right (according to the direction of translation).

As used herein, the term "coiled coil peptide chain segment" is a sequence of a peptide chain capable of forming a coiled coil (super coil) with at least one other coiled coil peptide chain segment. A coiled coil is a peptide structure in which at least two coiled coil peptide chain segments, each having preferably an alpha helical secondary structure, are associated into a bundle.

In a first aspect, the invention provides for a cyclic peptide comprising an amino acid sequence (I), wherein said amino acid sequence (I) comprises, preferably consists of, the amino acid sequence:

X1-X2-X3-C4-X5-X6-X7-C8-X9-X10-X11-P12-I13-
T14-N15-D16-Q17-K18-K19-L20-C21-X22-
X23-X24-C25-X26-X27-X28-X29-X30    (SEQ ID NO: 1), wherein X1, X2, X3, X5, X6, X7, X9, X10, X11, X22, X23, X24, X26, X27, X28 and X29 are independently of each other an amino acid;

C4, C8, C21 and C25 are independently of each other cysteine;

P12 is proline;

I13 is isoleucine;

T14 is threonine;

N15 is asparagine;

D16 is aspartic acid;

Q17 is glutamine;

K18 and K19 are independently of each other lysine;

L20 is leucine; and

X30 is an amino acid or a deletion, wherein said cysteines C4 and C25 form a first disulfide bond and said cysteines C8 and C21 form a second disulfide bond.

The cyclic peptides of the invention were successfully produced by using automated solid-phase peptide synthesis. Said disulfide bonds between cysteines C4 and C25 and cysteines C8 and C21 were obtained by oxidative refolding resulting in a beneficial spatial conformation.

In a preferred embodiment, said cyclic peptide has a length of at most 80 amino acids. In a further preferred embodiment, said cyclic peptide has a length of at most 60 amino acids. In a further preferred embodiment, said cyclic peptide has a length of at most 40 amino acids. In a further preferred embodiment, said cyclic peptide has a length of at most 30 amino acids.

In a preferred embodiment, said X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide, wherein preferably X11 is norleucine.

In another preferred embodiment, said X23 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, or cysteine-s-acetamide, wherein preferably X23 is asparagine.

In another preferred embodiment, said X23 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine. In another preferred embodiment, said X23 is selected from serine, homoserine, allo-threonine, 3,3-dihydroxy-alanine, 2-amino-5-hydroxypentanoic acid, 4-hydroxy-l-threonine, threonine, hydroxynorvaline, and 6-hydroxy-l-norleucine. In another preferred embodiment, said X23 is selected from glutamine, glycine, asparagine or serine. In another preferred embodiment, said X23 is selected from glutamine, glycine or serine. In another preferred embodiment, said X23 is asparagine or serine. In a further preferred embodiment, said X23 is serine. In a further preferred embodiment, said X23 is glutamine. In a further preferred embodiment, said X23 is glycine. In a further preferred embodiment, said X23 is asparagine.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; aspartic acid, 2-amino-6-oxopimelic acid, 3-methyl-aspartic acid, l-2-amino-6-methylene-pimelic acid, 4-hydroxy-glutamic-acid, 6-carboxylysine, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, or cysteine-s-acetamide.

In another preferred embodiment, said X24 is selected from lysine, 2,4-diaminobutyric acid, 2,3-diaminopropanoic acid, 2,8-diaminooctanoic acid, ornithine, amino-adipic acid or thialysine.

In another preferred embodiment, X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; aspartic acid, 2-amino-6-oxopimelic acid, 3-methyl-aspartic acid, l-2-amino-6-methylene-pimelic acid, 4-hydroxy-glutamic-acid, 6-carboxylysine, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid; wherein preferably X24 is selected from lysine, 2,4-diaminobutyric acid, 2,3-diaminopropanoic acid, 2,8-diaminooctanoic acid, ornithine, amino-adipic acid, asparagine, aspartic acid, or thialysine; wherein more preferably X24 is selected from lysine, 2,4-diaminobutyric acid, aspartic acid, or asparagine.

In another preferred embodiment, said X24 is selected from 2-amino-6-oxopimelic acid, 3-methyl-aspartic acid, l-2-amino-6-methylene-pimelic acid, 4-hydroxy-glutamic-acid, 6-carboxylysine, aspartic acid, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid. More preferably, X24 is selected of 3-methyl-aspartic acid, 6-carboxylysine, aspartic acid, beta-hydroxyaspartic acid, 3,3-dimethyl aspartic acid, or 2-amino-propanedioic acid.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, aspartic acid or thialysine, wherein preferably X24 is selected from lysine, 2,4-diaminobutyric acid, 2,3-diaminopropanoic acid, 2,8-diaminooctanoic acid, ornithine, amino-adipic acid, asparagine, aspartic acid or thialysine. In another preferred embodiment, X24 is selected from lysine, 2,4-diaminobutyric acid, asparagine, ornithine or aspartic acid. In another preferred embodiment, X24 is selected from lysine, 2,4-diaminobutyric acid, aspartic acid or asparagine. In another more preferred embodiment, X24 is selected from lysine, 2,4-diaminobutyric acid or asparagine. In another preferred embodiment, X24 is lysine. In another preferred embodiment, X24 is 2,4-diaminobutyric acid. In another preferred embodiment, X24 is asparagine. In another preferred embodiment, X24 is aspartic acid. In another preferred embodiment, X24 is ornithine.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; aspartic acid, 2-amino-6-oxopimelic acid, 3-methyl-aspartic acid, l-2-amino-6-methylene-pimelic acid, 4-hydroxy-glutamic-acid, 6-carboxylysine, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate, 2-aminoadipic acid; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, X24 is selected from glutamine, glutamine hydroxamate, 3-methyl-glutamine, n5-methyl-glutamine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, X24 is selected from asparagine, lysine, ornithine, 2,4-diaminobutyric acid (Dab), glutamine, glycine or serine. In another preferred embodiment, X24 is glycine, glutamine or serine. In another preferred embodiment, X24 is glutamine or serine. In another preferred embodiment, X24 is serine. In another preferred embodiment, X24 is glutamine. In another preferred embodiment, X24 is glycine.

In another preferred embodiment, X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide, and X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide, lysine, 2,4-diaminobutyric acid, 2,3-diaminopropanoic acid, 2,8-diaminooctanoic acid, ornithine, amino-adipic acid, aspartic acid or thialysine, wherein preferably X24 is selected from lysine, 2,4-diaminobutyric acid, 2,3-diaminopropanoic acid, 2,8-diaminooctanoic acid, ornithine, amino-adipic acid, asparagine, aspartic acid or thialysine. In another preferred embodiment, X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide; and X24 is selected from lysine, 2,4-diaminobutyric acid or asparagine, preferably X24 is lysine or 2,4-diaminobutyric acid.

In another preferred embodiment, X11 is norleucine, and X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide, lysine, 2,4-diaminobutyric acid, 2,3-diaminopropanoic acid, 2,8-diaminooctanoic acid, ornithine, amino-adipic acid, aspartic acid or thialysine, wherein preferably X24 is selected from lysine, 2,4-diaminobutyric acid, 2,3-diaminopropanoic acid, 2,8-diaminooctanoic acid, ornithine, amino-adipic acid, asparagine, aspartic acid or thialysine.

In a preferred embodiment, X11 is norleucine and X24 is lysine, 2,4-diaminobutyric acid, aspartic acid, ornithine or asparagine, preferably X24 is ornithine, aspartic acid, lysine or 2,4-diaminobutyric. In another preferred embodiment, X11 is norleucine and X24 is ornithine, aspartic acid, 2,4-diaminobutyric acid or asparagine. In another preferred embodiment, X11 is norleucine and X24 is ornithine, lysine, asparagine, or aspartic acid. In a preferred embodiment, X11 is norleucine and X24 is selected from ornithine, lysine, 2,4-diaminobutyric acid or asparagine. In a preferred embodiment, X11 is norleucine and X24 is selected from lysine, 2,4-diaminobutyric acid, aspartic acid or asparagine.

In another preferred embodiment, X11 is norleucine and X24 is selected from lysine, 2,4-diaminobutyric acid, aspartic acid, ornithine, serine, glutamine, glycine or asparagine, preferably X24 is selected from ornithine, aspartic acid, lysine or 2,4-diaminobutyric. In another preferred embodiment, X11 is norleucine and X24 is selected from 2,4-diaminobutyric acid, aspartic acid, ornithine serine, glutamine, glycine or asparagine. In another preferred embodiment, X11 is norleucine and X24 is selected from ornithine, lysine, asparagine, serine, glutamine, glycine or aspartic acid. In another preferred embodiment, X11 is norleucine and X24 is selected from ornithine, lysine, 2,4-diaminobutyric acid, serine, glutamine, glycine or asparagine. In another preferred embodiment, X11 is norleucine and X24 is selected from lysine, 2,4-diaminobutyric acid, aspartic acid, serine, glutamine, glycine or asparagine. In another preferred embodiment, X11 is norleucine and X24 is selected from serine, glutamine, glycine or asparagine. In another preferred embodiment, X11 is norleucine and X24 is selected from serine, glutamine, or glycine. In another preferred embodiment, X11 is norleucine and X24 is selected from serine, or glutamine. In another preferred embodiment, X11 is norleucine and X24 is selected from serine, or glutamine. In another preferred embodiment, X11 is norleucine and X24 is serine. In another preferred embodiment, X11 is norleucine and X24 is glutamine. In another preferred embodiment, X11 is norleucine and X24 is asparagine.

In another preferred embodiment, X11 is norleucine and X24 is aspartic acid, lysine or 2,4-diaminobutyric acid. In another preferred embodiment, X11 is norleucine and X24 is aspartic acid, 2,4-diaminobutyric acid or asparagine. In another preferred embodiment, X11 is norleucine and X24 is aspartic acid, 2,4-diaminobutyric acid or ornithine. In another preferred embodiment, X11 is norleucine and X24 is lysine, asparagine, or aspartic acid. In another preferred embodiment, X11 is norleucine and X24 is lysine, asparagine, or ornithine. In another preferred embodiment, X11 is norleucine and X24 is lysine, ornithine or aspartic acid. In another preferred embodiment, X11 is norleucine and X24 is ornithine, asparagine, or aspartic acid. In a preferred embodiment, X11 is norleucine and X24 is selected from lysine, 2,4-diaminobutyric acid or asparagine. In a preferred embodiment, X11 is norleucine and X24 is selected from lysine, 2,4-diaminobutyric acid or ornithine. In a preferred embodiment, X11 is norleucine and X24 is selected from asparagine, 2,4-diaminobutyric acid or ornithine.

In another preferred embodiment, X11 is norleucine and X24 is selected from aspartic acid, lysine, 2,4-diaminobutyric acid, serine, glutamine, or glycine. In another preferred embodiment, X11 is norleucine and X24 is selected from aspartic acid, 2,4-diaminobutyric acid, asparagine, serine, glutamine, or glycine. In another preferred embodiment, X11 is norleucine and X24 is selected from aspartic acid, 2,4-diaminobutyric acid, ornithine, serine, glutamine, or glycine. In another preferred embodiment, X11 is norleucine and X24 is selected from lysine, asparagine, aspartic acid, serine, glutamine, or glycine. In another preferred embodiment, X11 is norleucine and X24 is selected from lysine, asparagine, ornithine, serine, glutamine, or glycine. In another preferred embodiment, X11 is norleucine and X24 is selected from lysine, ornithine, aspartic acid, serine, glutamine, or glycine. In another preferred embodiment, X11 is norleucine and X24 is selected from ornithine, asparagine, or aspartic acid. In a preferred embodiment, X11 is norleucine and X24 is selected from lysine, 2,4-diaminobutyric acid, asparagine, serine, glutamine, or glycine. In a preferred embodiment, X11 is norleucine and X24 is selected from lysine, 2,4-diaminobutyric acid, ornithine, serine, glutamine, or glycine. In a preferred embodiment, X11 is norleucine and X24 is selected from asparagine, 2,4-diaminobutyric acid, ornithine, serine, glutamine, or glycine.

In a more preferred embodiment, X11 is norleucine and X24 is lysine or 2,4-diaminobutyric. In another preferred embodiment, X11 is norleucine and X24 is 2,4-diaminobutyric acid or asparagine. In another preferred embodiment, X11 is norleucine and X24 is 2,4-diaminobutyric acid or aspartic acid. In another preferred embodiment, X11 is norleucine and X24 is 2,4-diaminobutyric acid or ornithine. In another preferred embodiment, X11 is norleucine and X24 is lysine or asparagine. In another preferred embodiment, X11 is norleucine and X24 is lysine or ornithine. In another preferred embodiment, X11 is norleucine and X24 is aspartic acid or lysine. In another preferred embodiment, X11 is norleucine and X24 is aspartic acid or asparagine. In another preferred embodiment, X11 is norleucine and X24 is ornithine or asparagine. In another preferred embodiment, X11 is norleucine and X24 is aspartic acid or ornithine.

In a more preferred embodiment, X11 is norleucine and X24 is selected from lysine, 2,4-diaminobutyric, serine, glutamine, or glycine. In another preferred embodiment, X11 is norleucine and X24 is selected from 2,4-diaminobutyric acid, asparagine, serine, glutamine, or glycine. In another preferred embodiment, X11 is norleucine and X24 is selected from 2,4-diaminobutyric acid, aspartic acid, serine, glutamine, or glycine. In another preferred embodiment, X11 is norleucine and X24 is selected from 2,4-diaminobutyric acid, ornithine, serine, glutamine, or glycine. In another preferred embodiment, X11 is norleucine and X24 is selected from lysine, asparagine, serine, glutamine, or glycine. In another preferred embodiment, X11 is norleucine and X24 is selected from lysine, ornithine, serine, glutamine, or glycine. In another preferred embodiment, X11 is norleucine and X24 is selected from aspartic acid, lysine, serine, glutamine, or glycine. In another preferred embodiment, X11 is norleucine and X24 is selected from aspartic acid, asparagine, serine, glutamine, or glycine. In another preferred embodiment, X11 is norleucine and X24 is selected from ornithine, asparagine, serine, glutamine, or glycine. In another preferred embodiment, X11 is norleucine and X24 is selected from aspartic acid, ornithine, serine, glutamine, or glycine.

In another preferred embodiment, X11 is norleucine and X24 is aspartic acid. In another preferred embodiment, X11 is norleucine and X24 is asparagine. In another preferred embodiment, X11 is norleucine and X24 is ornithine. In another preferred embodiment, X11 is norleucine and X24 is 2,4-diaminobutyric acid. In another preferred embodiment, X11 is norleucine and X24 is lysine.

In another preferred embodiment, X11 is norleucine and X24 is selected from aspartic acid, ornithine, serine, glutamine, or glycine. In another preferred embodiment, X11 is norleucine and X24 is selected from asparagine, ornithine, serine, glutamine, or glycine. In another preferred embodiment, X11 is norleucine and X24 is selected from ornithine, ornithine, serine, glutamine, or glycine. In another preferred embodiment, X11 is norleucine and X24 is selected from 2,4-diaminobutyric acid, ornithine, serine, glutamine, or glycine. In another preferred embodiment, X11 is norleucine and X24 is selected from lysine, ornithine, serine, glutamine, or glycine.

In a preferred embodiment, the C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, the C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, 2-aminoheptanoic acid, serine, glutamine or glycine.

In another preferred embodiment, X11 is norleucine, X24 is ornithine, aspartic acid, 2,4-diaminobutyric acid, lysine or asparagine, and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another more preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid.

In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another more preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid.

In another preferred embodiment, X11 is norleucine, X24 is selected from serine, glutamine, glycine, or asparagine, preferably from serine, glutamine, or glycine; and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid; preferably, said C-terminal amino acid of said amino acid sequence (I) is a D-stereoisomer. In another more preferred embodiment, X11 is norleucine, X24 is selected from serine, glutamine, glycine, or asparagine, preferably from serine, glutamine, or glycine; and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid; preferably, said C-terminal amino acid of said amino acid sequence (I) is a D-stereoisomer.

In another preferred embodiment, X11 is norleucine, X24 is ornithine, aspartic acid, 2,4-diaminobutyric acid, lysine or asparagine, and said C-terminal amino acid of said amino acid sequence (I) is a D-amino acid. In another preferred embodiment, X11 is norleucine, X24 is ornithine, aspartic acid, 2,4-diaminobutyric acid, lysine or asparagine, and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is a D-amino acid. In another preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is ornithine, aspartic acid, 2,4-diaminobutyric acid, lysine or asparagine, and said C-terminal amino acid of said amino acid sequence (I) is alanine, preferably D-alanine. In another more preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is alanine, preferably D-alanine.

In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is a D-amino acid. In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is a D-amino acid. In another preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is alanine, preferably D-alanine. In another more preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is alanine, preferably D-alanine.

In another preferred embodiment, said X1 is a polar or hydrophobic amino acid. Preferably, X1 is selected of asparagine, beta-hydroxyasparagine, 2,5-diamino-4-hydroxy-5-oxopentanoic acid, glutamine, glutamine hydroxamate, 3-methyl-l-glutamine, n-methyl-asparagine, n5-methyl-glutamine, cysteine-s-acetamide; leucine, alloleucine, alloisoleucine, homoleucine, isoleucine, 2-aminobutyric acid, norleucine, norvaline or valine. In another more preferred embodiment, X1 is asparagine or leucine. In another again more preferred embodiment, X1 is asparagine. In another again more preferred embodiment, X1 is leucine.

In another preferred embodiment, said X1 is selected from asparagine, beta-hydroxyasparagine, 2,5-diamino-4-hydroxy-5-oxopentanoic acid, glutamine, glutamine hydroxamate, 3-methyl-l-glutamine, n-methyl-asparagine, n5-methyl-glutamine, cysteine-s-acetamide; leucine, alloleucine, alloisoleucine, homoleucine, isoleucine, 2-aminobutyric acid, norleucine, norvaline, valine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine; or glycine.

In another preferred embodiment, said X1 is selected from glutamine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine; or glycine. In another preferred embodiment, said X1 is selected from serine, homoserine, allo-threonine, 3,3-dihydroxy-alanine, 2-amino-5-hydroxypentanoic acid, 4-hydroxy-l-threonine, threonine, hydroxynorvaline, or 6-hydroxy-l-norleucine.

In another preferred embodiment, said X1 is selected from asparagine, glutamine, leucine, serine, or glycine. In another preferred embodiment, said X1 is selected from asparagine, glutamine, serine, or glycine. In another preferred embodiment, said X1 is selected from asparagine, or serine. In another preferred embodiment, said X1 is selected from asparagine, or glutamine. In another preferred embodiment, said X1 is selected from glutamine, serine, or glycine. In another preferred embodiment, said X1 is glycine. In another preferred embodiment, said X1 is glutamine. In another preferred embodiment, said X1 is serine.

In another preferred embodiment, said X1, X23 and X24 are each independently selected from the group consisting of ornithine, aspartic acid, lysine, asparagine, 2,4-diaminobutyric acid (Dab), glutamine, leucine, serine, and glycine. In another preferred embodiment, said X1, X23 and X24 are each independently selected from the group consisting of asparagine, 2,4-diaminobutyric acid (Dab), glutamine, leucine, serine, and glycine. In another preferred embodiment, said X1, X23 and X24 are each independently selected from the group consisting of asparagine, glutamine, serine, and glycine. In another preferred embodiment, said X1, X23 and X24 are each independently selected from the group consisting of glutamine, serine, and glycine. In another preferred embodiment, said X1 is selected from asparagine, glutamine, leucine, serine, or glycine; said X23 is selected from asparagine or serine; and said X24 is selected from asparagine, 2,4-diaminobutyric acid (Dab), glutamine, or serine. In another preferred embodiment, said X1 is selected from glutamine, serine, or glycine; said X23 is serine; and said X24 is glutamine or serine.

In another preferred embodiment, said X2, X6 and X22 are independently of each other a polar amino acid. Preferably, X2, X6 and X22 are independently of each other selected of 2-amino-5-hydroxypentanoic acid, allo-threonine, 4-chloro-threonine, 3,3-dihydroxy-alanine, 4-hydroxy-L-isoleucine, (2s,3r)-2-amino-3-hydroxy-4-methylpentanoic acid, beta-hydroxy-leucine, homoserine, 3-hydroxy-l-valine, 4,5-dihydroxy-isoleucine, 6-hydroxy-l-norleucine, s-(2-hydroxyethyl)-1-cysteine, phosphoserine, serine, 4-hydroxy-l-threonine, threonine, phosphothreonine or hydroxynorvaline. Again more preferably, X2, X6 and X22 are independently of each other serine. In another preferred embodiment, X2 and X6 are serine. In another preferred embodiment, X6 and X22 are serine. In another preferred embodiment, X2 and X22 are serine. In another preferred embodiment, X2, X6 and X22 are serine.

In another preferred embodiment, said X3 is an amino acid having an acidic or negatively charged side chain at a physiological pH (about pH 7). Preferably, X3 is selected of glutamate, 5-o-methyl-glutamic acid, (3r)-3-methyl-l-glutamic acid, (3s)-3-methyl-l-glutamic acid, 2s,4r-4-methylglutamate, 4-hydroxy-glutamic-acid, 2-aminoadipic acid, l-2-amino-6-methylene-pimelic acid, 2-amino-6-oxopimelic acid; 3-methyl-aspartic acid, 6-carboxylysine, aspartic acid, beta-hydroxyaspartic acid, 3,3-dimethyl aspartic acid, or 2-amino-propanedioic acid. More preferably, X3 is selected of glutamate, 5-o-methyl-glutamic acid, (3r)-3-methyl-l-glutamic acid, (3s)-3-methyl-l-glutamic acid, 2s,4r-4-methylglutamate, 4-hydroxy-glutamic-acid, 2-aminoadipic acid, l-2-amino-6-methylene-pimelic acid or 2-amino-6-oxopimelic acid. In another again more preferred embodiment, X3 is glutamate.

In another preferred embodiment, said X5 and X7 are independently of each other a hydrophobic amino acid. Preferably, X5 and X7 are independently of each other selected of leucine, alloleucine, alloisoleucine, homoleucine, isoleucine, 2-aminobutyric acid, norleucine, norvaline or valine. More preferably, X5 or X7 is leucine. In another more again preferred embodiment, X5 and X7 are leucine.

In another preferred embodiment, said X9 and X23 are independently of each other a polar amino acid. Preferably, X9 and X23 are independently of each other selected of asparagine, beta-hydroxyasparagine, 2,5-diamino-4-hydroxy-5-oxopentanoic acid, glutamine, glutamine hydroxamate, 3-methyl-l-glutamine, n-methyl-asparagine, n5-methyl-glutamine or cysteine-s-acetamide. In another more preferred embodiment, X9 or X23 is asparagine. In another again more preferred embodiment, X9 and X23 are asparagine.

Preferably, X9 and X23 are independently of each other selected of asparagine, glutamine, serine or glycine. In another more preferred embodiment, X9 or X23 is selected from asparagine, glutamine, serine or glycine. In another again more preferred embodiment, X9 and X23 are both selected from asparagine, glutamine, serine or glycine.

In another preferred embodiment, said X10 is an amino acid having an acidic or negatively charged side chain at a physiological pH (about pH 7). Preferably, X10 is selected of 2-amino-6-oxopimelic acid, 3-methyl-aspartic acid, l-2-amino-6-methylene-pimelic acid, 4-hydroxy-glutamic-acid, 6-carboxylysine, aspartic acid, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid. More preferably, X10 is selected of 3-methyl-aspartic acid, 6-carboxylysine, aspartic acid, beta-hydroxyaspartic acid, 3,3-dimethyl aspartic acid, or 2-amino-propanedioic acid. In another again more preferred embodiment, X10 is aspartic acid.

In another preferred embodiment, said X26 is a hydrophobic or polar amino acid. Preferably, X26 is selected of leucine, alloleucine, alloisoleucine, homoleucine, isoleucine, 2-aminobutyric acid, norleucine, norvaline, valine; 2,5-diamino-4-hydroxy-5-oxopentanoic acid, glutamine hydroxamate, 3-methyl-l-glutamine, n5-methyl-glutamine, asparagine, 2,5-diamino-4-hydroxy-5-oxopentanoic acid, or n-methyl-asparagine. More preferably, X26 is leucine or glutamine.

In another preferred embodiment, said X27 is a polar or hydrophobic amino acid or an amino acid having an acidic or negatively charged side chain at a physiological pH (about pH 7). Preferably, X27 is selected of selected of 2-amino-5-hydroxypentanoic acid, allo-threonine, 4-chloro-threonine, 3,3-dihydroxy-alanine, 4-hydroxy-L-isoleucine, (2s,3r)-2-amino-3-hydroxy-4-methylpentanoic acid, beta-hydroxy-leucine, homoserine, 3-hydroxy-l-valine, 4,5-dihydroxy-isoleucine, 6-hydroxy-l-norleucine, s-(2-hydroxyethyl)-1-cysteine, phosphoserine, serine, 4-hydroxy-l-threonine, threonine, phosphothreonine, hydroxynorvaline; leucine, alloleucine, alloisoleucine, homoleucine, isoleucine, 2-aminobutyric acid, norleucine, norvaline, valine; diaminobutyric acid, 2,3-diaminopropanoic acid, (2s)-2,8-diaminooctanoic acid, lysine, ornithine, or thialysine. More preferably, X27 is serine, isoleucine, or lysine.

In another preferred embodiment, said X28 is a polar or hydrophobic amino acid. Preferably, X28 is selected of 2-amino-5-hydroxypentanoic acid, allo-threonine, 4-chloro-threonine, 3,3-dihydroxy-alanine, 4-hydroxy-L-isoleucine, (2s,3r)-2-amino-3-hydroxy-4-methylpentanoic acid, beta-hydroxy-leucine, homoserine, 3-hydroxy-l-valine, 4,5-dihydroxy-isoleucine, 6-hydroxy-l-norleucine, s-(2-hydroxyethyl)-1-cysteine, phosphoserine, serine, 4-hydroxy-l-threonine, threonine, phosphothreonine, hydroxynorvaline; leucine, alloleucine, alloisoleucine, homoleucine, isoleucine, 2-aminobutyric acid, norleucine, norvaline, or valine. More preferably, X28 is valine or serine.

In another preferred embodiment, said X29 is a hydrophobic amino acid or an amino acid having a negatively charged side chain at physiological pH (about pH 7). Preferably, X29 is selected of the D- or L-stereoisomer, preferably the D-stereoisomer of 2-allyl-glycine, 2-aminobutyric acid, 2-aminoheptanoic acid, alanine, tertleucine, diethylalanine, homoleucine, 3-methyl-l-alloisoleucine, allo-isoleucine, isoleucine, leucine, vinylglycine, norleucine, norvaline, valine; 5-methyl-arginine, arginine, c-gamma-hydroxy arginine, citrulline, 2-amino-4-guanidinobutryric acid, 2-amino-3-guanidinopropionic acid, canavanine, homoarginine, or thio-citrulline. In another preferred embodiment, X29 is D- or L-alanine or D- or L-arginine. In another more preferred embodiment, X29 is D-alanine or D-arginine.

In another preferred embodiment, said X30 is a deletion or a hydrophobic or polar D- or L-amino acid, preferably X30 is a hydrophobic or polar amino acid D-amino acid. Preferably, X30 is a deletion or X30 is selected of the D- or L-stereoisomer, preferably the D-stereoisomer of 2-allyl-glycine, 2-aminobutyric acid, 2-aminoheptanoic acid, alanine, tertleucine, diethylalanine, homoleucine, 3-methyl-l-alloisoleucine, allo-isoleucine, isoleucine, leucine, vinylglycine, norleucine, norvaline, valine; 2,5-diamino-4-hydroxy-5-oxopentanoic acid, glutamine hydroxamate, 3-methyl-l-glutamine, n5-methyl-glutamine, asparagine, 2,5-diamino-4-hydroxy-5-oxopentanoic acid, or n-methyl-asparagine. In another preferred embodiment, X30 is D- or L-glutamine or D- or L-alanine. In another more preferred embodiment, X30 is D-glutamine or D-alanine. In another again more preferred embodiment, X30 is D-alanine.

In a preferred embodiment, X30 is a deletion and X29 is alanine, preferably D-alanine. In another preferred embodiment, X30 is alanine, preferably D-alanine and X29 is arginine.

In another preferred embodiment, X1 is asparagine or leucine, X2 is serine, and X3 is glutamate.

In another preferred embodiment, X1 is serine, glycine, glutamine, asparagine or leucine, X2 is serine, and X3 is glutamate. In another preferred embodiment, X1 is serine, asparagine or leucine, X2 is serine, and X3 is glutamate. In another preferred embodiment, X1 is serine, X2 is serine, and X3 is glutamate.

In another preferred embodiment, X5 is leucine, X6 is serine, and X7 is leucine.

In another preferred embodiment, X9 is asparagine, X10 is aspartic acid and X11 is norleucine or methionine, preferably X11 is norleucine.

In another preferred embodiment, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X22 is serine, X23 is selected from asparagine, serine, glycine or glutamine, and X24 is selected from serine, glycine, glutamine, Dab (2,4-diaminobutyric acid), asparagine or lysine. In another preferred embodiment, X22 is serine, and X23 and X24 are selected from glutamine, glycine, serine, or asparagine. In another preferred embodiment, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, and X7 is leucine. In another preferred embodiment, X1 is asparagine or leucine, X2 is serine, X3 is glutamate, X9 is asparagine, X10 is aspartic acid and X11 is norleucine or methionine, preferably X11 is norleucine. In another preferred embodiment, X1 is asparagine or leucine, X2 is serine, X3 is glutamate, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, and X7 is leucine. In another preferred embodiment, X1 is asparagine or leucine, X2 is serine, X3 is glutamate, X9 is asparagine, X10 is aspartic acid and X11 is norleucine or methionine, preferably X11 is norleucine. In another preferred embodiment, X1 is asparagine or leucine, X2 is serine, X3 is glutamate, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X5 is leucine, X6 is serine, X7 is leucine, X9 is asparagine, X10 is aspartic acid and X11 is norleucine or methionine, preferably X11 is norleucine. In another preferred embodiment, X5 is leucine, X6 is serine, X7 is leucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X5 is leucine, X6 is serine, X7 is leucine, X22 is serine, X23 is selected from asparagine, serine, glycine, glutamine, and X24 is selected from serine, glycine, glutamine, Dab (2,4-diaminobutyric acid), asparagine or lysine, preferably X24 and X23 are asparagine, serine, glycine, or glutamine. In another preferred embodiment, X5 is leucine, X6 is serine, X7 is leucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X9 is asparagine, X10 is aspartic acid, X11 is norleucine or methionine, preferably X11 is norleucine, X22 is serine, X23 is serine, glycine, glutamine, asparagine, and X24 is selected from serine, glycine, glutamine, Dab (2,4-diaminobutyric acid), asparagine or lysine, preferably X23 and X24 are selected from serine, glycine, glutamine, asparagine. In another preferred embodiment, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is a deletion, D- or L-alanine, more preferably X30 is D-alanine.

In another preferred embodiment, X22 is serine, X23 is asparagine, X24 is Dab (2,4-diaminobutyric acid), asparagine or lysine, preferably X24 is Dab (2,4-diaminobutyric acid) or lysine, X26 is glutamine or leucine, X27 is serine, lysine or isoleucine, X28 is valine X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X22 is serine, X23 is asparagine, serine, glycine, glutamine, X24 is serine, glycine, glutamine, Dab (2,4-diaminobutyric acid), asparagine or lysine, X26 is glutamine or leucine, X27 is serine, lysine or isoleucine, X28 is valine X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine. In another preferred embodiment, X1 is asparagine or leucine, X2 is serine, X3 is glutamate, X5 is leucine, X6 is serine, X7 is leucine, X9 is asparagine, X10 is aspartic acid, and X11 is norleucine or methionine, preferably X11 is norleucine. In another preferred embodiment, X1 is asparagine or leucine, X2 is serine, X3 is glutamate, X5 is leucine, X6 is serine, X7 is leucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X5 is leucine, X6 is serine, X7 is leucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is serine, glycine, glutamine, asparagine or leucine, X2 is serine, X3 is glutamate, X5 is leucine, X6 is serine, X7 is leucine, X9 is asparagine, X10 is aspartic acid, and X11 is norleucine or methionine, preferably X11 is norleucine. In another preferred embodiment, X1 is serine, glycine, glutamine, asparagine or leucine, X2 is serine, X3 is glutamate, X5 is leucine, X6 is serine, X7 is leucine, X22 is serine, X23 is serine, glycine, glutamine, asparagine, and X24 is serine, glycine, glutamine Dab (2,4-diaminobutyric acid), asparagine or lysine. In another preferred embodiment, X1 is serine, glycine, glutamine, asparagine or leucine, X2 is serine, X3 is glutamate, X5 is leucine, X6 is serine, X7 is leucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is a deletion, D- or L-alanine, more preferably X30 is D-alanine.

In another preferred embodiment, X1 is selected from serine, glycine, glutamine, asparagine or leucine, X2 is serine, X3 is glutamate, X9 is asparagine, X10 is aspartic acid, X11 is norleucine or methionine, preferably X11 is norleucine, X22 is serine, X23 is selected from serine, glycine, glutamine, asparagine, and X24 is selected from serine, glycine, glutamine, Dab (2,4-diaminobutyric acid), asparagine or lysine. In another preferred embodiment, X1 is selected from serine, glycine, glutamine, asparagine or leucine, X2 is serine, X3 is glutamate, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is a deletion, D- or L-alanine, more preferably X30 is D-alanine. In another preferred embodiment, X5 is leucine, X6 is serine, X7 is leucine, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X5 is leucine, X6 is serine, X7 is leucine, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is D- or L-alanine, more preferably X30 is D-alanine. In another preferred embodiment, X5 is leucine, X6 is serine, X7 is leucine, X22 is serine, X23 is asparagine, X24 is Dab (2,4-diaminobutyric acid), asparagine or lysine, preferably X24 is Dab (2,4-diaminobutyric acid) or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine. In another preferred embodiment, X9 is asparagine, X10 is aspartic acid, X11 is norleucine or methionine, preferably X11 is norleucine, X22 is serine, X23 is asparagine, X24 is Dab (2,4-diaminobutyric acid), asparagine or lysine, preferably X24 is Dab (2,4-diaminobutyric acid) or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X5 is leucine, X6 is serine, X7 is leucine, X9 is asparagine, X10 is aspartic acid, X11 is norleucine or methionine, preferably X11 is norleucine, X22 is serine, X23 is selected from serine, glycine, glutamine, asparagine, and X24 is selected from serine, glycine, glutamine, Dab (2,4-diaminobutyric acid), ornithine, aspartic acid, asparagine or lysine. In another preferred embodiment, X5 is leucine, X6 is serine, X7 is leucine, X22 is serine, X23 is selected from serine, glycine, glutamine, asparagine, X24 is selected from serine, glycine, glutamine, ornithine, aspartic acid, Dab (2,4-diaminobutyric acid), asparagine or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine. In another preferred embodiment, X9 is asparagine, X10 is aspartic acid, X11 is norleucine or methionine, preferably X11 is norleucine, X22 is serine, X23 is selected from serine, glycine, glutamine, asparagine, X24 is selected from serine, glycine, glutamine, ornithine, aspartic acid, Dab (2,4-diaminobutyric acid), asparagine or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine.

In another preferred embodiment, X1 is selected from glutamine, serine, glycine, asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X22 is serine, X23 is selected from glutamine, serine, glycine, asparagine, and X24 is selected from glutamine, serine, glycine, ornithine, aspartic acid, Dab (2,4-diaminobutyric acid), asparagine or lysine.

In another preferred embodiment, X1 is asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is selected from glutamine, serine, glycine, asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid.

In a certain embodiment, the C-terminal amino acid of said amino acid sequence (1) is a D-amino acid, preferably said C-terminal amino acid is selected from D-alanine, D-leucine, D-valine, D-norleucine, D-norvaline, D-isoleucine, D-homoleucine, D-vinylglycine, D-2-aminobutyric acid, D-2-allylglycine, D-alloleucine D-alloisoleucine, or D-2-aminoheptanoic acid.

In a preferred embodiment, said X2, X3, X5, X6, X7, X9, X10, X11, X22, X23, X24, X26, X27, X28 and X29 are independently of each other L-amino acids.

In a preferred embodiment proline P12, isoleucine I13, threonine T14, asparagine N15, aspartic acid D16, glutamine Q17, lysines K18 and K19, and leucine L20 are independently of each other L-amino acids.

In a preferred embodiment, C4, C8, C21 and C25 are independently of each other D-cysteine or L-cysteine, preferably L-cysteine.

In a preferred embodiment, the cyclic peptide of the invention consists of said amino acid sequence (I).

In another preferred embodiment, said amino acid sequence (I) consists of said amino acid sequence of SEQ ID NO: 1.

In another very preferred embodiment, said amino acid sequence of SEQ ID NO: 1 is an amino acid selected from:

```
                                           (SEQ ID NO: 2)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Dab-
Cys-Gln-Ser-Val-Arg-ala, (SEQ ID NO: 3)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Lys-
Cys-Gln-Ser-Val-Arg-ala, (SEQ ID NO: 21)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Asn-
Cys-Gln-Ser-Val-Arg-ala, (SEQ ID NO: 22)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Asp-
Cys-Gln-Ser-Val-Arg-ala
or (SEQ ID NO: 23)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Orn-
Cys-Gln-Ser-Val-Arg-ala.
```

In another very preferred embodiment, said amino acid sequence of SEQ ID NO: 1 is selected from any one of SEQ ID NO: 2-5, 21-36, or

```
SEQ ID NO: 39:
NSECLSLCND-Nle-PITNDQKKLCSS-Dab-CQSVRa,

SEQ ID NO: 40:
NSECLSLCND-Nle-PITNDQKKLCSSNCQSVRa,

SEQ ID NO: 41:
NSECLSLCND-Nle-PITNDQKKLCSSQCQSVRa,

SEQ ID NO: 42:
NSECLSLCND-Nle-PITNDQKKLCSSSCQSVRa,

SEQ ID NO: 43:
QSECLSLCND-Nle-PITNDQKKLCSN-Dab-CQSVRa,

SEQ ID NO: 44:
QSECLSLCND-Nle-PITNDQKKLCSS-Dab-CQSVRa,

SEQ ID NO: 45:
QSECLSLCND-Nle-PITNDQKKLCSSNCQSVRa,

SEQ ID NO: 46:
QSECLSLCND-Nle-PITNDQKKLCSSQCQSVRa,

SEQ ID NO: 47:
QSECLSLCND-Nle-PITNDQKKLCSSSCQSVRa,

SEQ ID NO: 48:
SSECLSLCND-Nle-PITNDQKKLCSN-Dab-CQSVRa,

SEQ ID NO: 49:
SSECLSLCND-Nle-PITNDQKKLCSS-Dab-CQSVRa,

SEQ ID NO: 50:
SSECLSLCND-Nle-PITNDQKKLCSSNCQSVRa,

SEQ ID NO: 51:
SSECLSLCND-Nle-PITNDQKKLCSSQCQSVRa,

SEQ ID NO: 52:
SSECLSLCND-Nle-PITNDQKKLCSSSCQSVRa,

SEQ ID NO: 53:
GSECLSLCND-Nle-PITNDQKKLCSN-Dab-CQSVRa,

SEQ ID NO: 54:
GSECLSLCND-Nle-PITNDQKKLCSS-Dab-CQSVRa,

SEQ ID NO: 55:
GSECLSLCND-Nle-PITNDQKKLCSSNCQSVRa,

SEQ ID NO: 56:
GSECLSLCND-Nle-PITNDQKKLCSSQCQSVRa,
or

SEQ ID NO: 57:
GSECLSLCND-Nle-PITNDQKKLCSSSCQSVRa.
```

In another very preferred embodiment, said amino acid sequence of SEQ ID NO: 1 is an amino acid selected from SEQ ID NO: 2 or SEQ ID NO: 3.

In another very preferred embodiment, said amino acid sequence of SEQ ID NO: 1 is the amino acid of SEQ ID NO: 2. In another very preferred embodiment, said amino acid sequence of SEQ ID NO: 1 is the amino acid of SEQ ID NO: 3. In another very preferred embodiment, said amino acid sequence of SEQ ID NO: 1 is the amino acid of SEQ ID NO: 21. In another very preferred embodiment, said amino acid sequence of SEQ ID NO: 1 is the amino acid of SEQ ID NO: 22. In another very preferred embodiment, said amino acid sequence of SEQ ID NO: 1 is the amino acid of SEQ ID NO: 23.

In another very preferred embodiment, said amino acid sequence of SEQ ID NO: 1 is the amino acid of SEQ ID NO:

39. In another very preferred embodiment, said amino acid sequence of SEQ ID NO: 1 is the amino acid of SEQ ID NO: 40. In another very preferred embodiment, said amino acid sequence of SEQ ID NO: 1 is the amino acid of SEQ ID NO: 41. In another very preferred embodiment, said amino acid sequence of SEQ ID NO: 1 is the amino acid of SEQ ID NO: 42. In another very preferred embodiment, said amino acid sequence of SEQ ID NO: 1 is the amino acid of SEQ ID NO: 43. In another very preferred embodiment, said amino acid sequence of SEQ ID NO: 1 is the amino acid of SEQ ID NO: 44. In another very preferred embodiment, said amino acid sequence of SEQ ID NO: 1 is the amino acid of SEQ ID NO: 45. In another very preferred embodiment, said amino acid sequence of SEQ ID NO: 1 is the amino acid of SEQ ID NO: 46. In another very preferred embodiment, said amino acid sequence of SEQ ID NO: 1 is the amino acid of SEQ ID NO: 47. In another very preferred embodiment, said amino acid sequence of SEQ ID NO: 1 is the amino acid of SEQ ID NO: 48. In another very preferred embodiment, said amino acid sequence of SEQ ID NO: 1 is the amino acid of SEQ ID NO: 49. In another very preferred embodiment, said amino acid sequence of SEQ ID NO: 1 is the amino acid of SEQ ID NO: 50. In another very preferred embodiment, said amino acid sequence of SEQ ID NO: 1 is the amino acid of SEQ ID NO: 51. In another very preferred embodiment, said amino acid sequence of SEQ ID NO: 1 is the amino acid of SEQ ID NO: 52. In another very preferred embodiment, said amino acid sequence of SEQ ID NO: 1 is the amino acid of SEQ ID NO: 53. In another very preferred embodiment, said amino acid sequence of SEQ ID NO: 1 is the amino acid of SEQ ID NO: 54. In another very preferred embodiment, said amino acid sequence of SEQ ID NO: 1 is the amino acid of SEQ ID NO: 55. In another very preferred embodiment, said amino acid sequence of SEQ ID NO: 1 is the amino acid of SEQ ID NO: 56. In another very preferred embodiment, said amino acid sequence of SEQ ID NO: 1 is the amino acid of SEQ ID NO: 57.

In another very preferred embodiment, said amino acid sequence (I) is selected from:

(SEQ ID NO: 2)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Dab-
Cys-Gln-Ser-Val-Arg-ala, (SEQ ID NO: 3)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Lys-
Cys-Gln-Ser-Val-Arg-ala, (SEQ ID NO: 4)
Arg-Leu-Ser-Glu-Cys-Leu-Ser-Leu-Cys-Asn-Asp-Nle-
Pro-Ile-Thr-Asn-Asp-Gln-Lys-Lys-Leu-Cys-Ser-Asn-
Asn-Cys-Leu-Lys-Ser-ala, (SEQ ID NO: 5)
Pro-Val-Ser-Thr-Tyr-Met-Leu-Thr-Asn-Ser-Glu-Cys-
Leu-Ser-Leu-Cys-Asn-Asp-Met-Pro-Ile-Thr-Asn-Asp-
Gln-Lys-Lys-Leu-Cys-Ser-Asn-Asn-Cys-Gln-Ile-Val-
Arg-Gln-Gln-ala, (SEQ ID NO: 21)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Asn-
Cys-Gln-Ser-Val-Arg-ala, (SEQ ID NO: 22)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Asp-
Cys-Gln-Ser-Val-Arg-ala, (SEQ ID NO: 23)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Orn-
Cys-Gln-Ser-Val-Arg-ala, (SEQ ID NO: 24)
Arg-Leu-Ser-Glu-Cys-Leu-Ser-Leu-Cys-Asn-Asp-Nle-
Pro-Ile-Thr-Asn-Asp-Gln-Lys-Lys-Leu-Cys-Ser-Asn-
Lys-Cys-Leu-Lys-Ser-ala, (SEQ ID NO: 25)
Arg-Leu-Ser-Glu-Cys-Leu-Ser-Leu-Cys-Asn-Asp-Nle-
Pro-Ile-Thr-Asn-Asp-Gln-Lys-Lys-Leu-Cys-Ser-Asn-
Dab-Cys-Leu-Lys-Ser-ala, (SEQ ID NO: 26)
Pro-Val-Ser-Thr-Tyr-Met-Leu-Thr-Asn-Ser-Glu-Cys-
Leu-Ser-Leu-Cys-Asn-Asp-Met-Pro-Ile-Thr-Asn-Asp-
Gln-Lys-Lys-Leu-Cys-Ser-Asn-Lys-Cys-Gln-Ile-Val-
Arg-Gln-Gln-ala, (SEQ ID NO: 27)
Pro-Val-Ser-Thr-Tyr-Met-Leu-Thr-Asn-Ser-Glu-Cys-
Leu-Ser-Leu-Cys-Asn-Asp-Met-Pro-Ile-Thr-Asn-Asp-
Gln-Lys-Lys-Leu-Cys-Ser-Asn-Dab-Cys-Gln-Ile-Val-
Arg-Gln-Gln-ala, (SEQ ID NO: 28)
Arg-Leu-Ser-Glu-Cys-Leu-Ser-Leu-Cys-Asn-Asp-Nle-
Pro-Ile-Thr-Asn-Asp-Gln-Lys-Lys-Leu-Cys-Ser-Asn-
Asp-Cys-Leu-Lys-Ser-ala, (SEQ ID NO: 29)
Arg-Leu-Ser-Glu-Cys-Leu-Ser-Leu-Cys-Asn-Asp-Nle-
Pro-Ile-Thr-Asn-Asp-Gln-Lys-Lys-Leu-Cys-Ser-Asn-
Orn-Cys-Leu-Lys-Ser-ala, (SEQ ID NO: 30)
Pro-Val-Ser-Thr-Tyr-Met-Leu-Thr-Asn-Ser-Glu-Cys-
Leu-Ser-Leu-Cys-Asn-Asp-Met-Pro-Ile-Thr-Asn-Asp-
Gln-Lys-Lys-Leu-Cys-Ser-Asn-Asp-Cys-Gln-Ile-Val-
Arg-Gln-Gln-ala, (SEQ ID NO: 31)
Pro-Val-Ser-Thr-Tyr-Met-Leu-Thr-Asn-Ser-Glu-Cys-
Leu-Ser-Leu-Cys-Asn-Asp-Met-Pro-Ile-Thr-Asn-Asp- Gln-Lys-Lys-Leu-Cys-Ser-Asn-Orn-Cys-Gln-Ile-Val- Arg-Gln-Gln-ala, (SEQ ID NO: 32)
Pro-Val-Ser-Thr-Tyr-Met-Leu-Thr-Asn-Ser-Glu-Cys- Leu-Ser-Leu-Cys-Asn-Asp-Nle-Pro-Ile-Thr-Asn-Asp- Gln-Lys-Lys-Leu-Cys-Ser-Asn-Asn-Cys-Gln-Ile-Val- Arg-Gln-Gln-ala, (SEQ ID NO: 33)
Pro-Val-Ser-Thr-Tyr-Met-Leu-Thr-Asn-Ser-Glu-Cys- Leu-Ser-Leu-Cys-Asn-Asp-Nle-Pro-Ile-Thr-Asn-Asp- Gln-Lys-Lys-Leu-Cys-Ser-Asn-Lys-Cys-Gln-Ile-Val- Arg-Gln-Gln-ala,
or (SEQ ID NO: 34)
Pro-Val-Ser-Thr-Tyr-Met-Leu-Thr-Asn-Ser-Glu-Cys- Leu-Ser-Leu-Cys-Asn-Asp-Nle-Pro-Ile-Thr-Asn-Asp- Gln-Lys-Lys-Leu-Cys-Ser-Asn-Dab-Cys-Gln-Ile-Val- Arg-Gln-Gln-ala.

(SEQ ID NO: 35)
Pro-Val-Ser-Thr-Tyr-Met-Leu-Thr-Asn-Ser-Glu-Cys-

Leu-Ser-Leu-Cys-Asn-Asp-Nle-Pro-Ile-Thr-Asn-Asp-

Gln-Lys-Lys-Leu-Cys-Ser-Asn-Asp-Cys-Gln-Ile-Val-

Arg-Gln-Gln-ala,
or (SEQ ID NO: 36)
Pro-Val-Ser-Thr-Tyr-Met-Leu-Thr-Asn-Ser-Glu-Cys- Leu-Ser-Leu-Cys-Asn-Asp-Nle-Pro-Ile-Thr-Asn-Asp- Gln-Lys-Lys-Leu-Cys-Ser-Asn-Orn-Cys-Gln-Ile-Val- Arg-Gln-Gln-ala.

In another very preferred embodiment, said amino acid sequence (I) is selected from any one of SEQ ID NO: 2-5, 21-36, or SEQ ID NO: 39-57.

In another very preferred embodiment, said amino acid sequence (I) is selected from any one of (SEQ ID NO: 2), (SEQ ID NO: 3), (SEQ ID NO: 4), (SEQ ID NO: 5) or (SEQ ID NO: 32). In another very preferred embodiment, said amino acid sequence (I) is selected from any one of (SEQ ID NO: 2), (SEQ ID NO: 3), (SEQ ID NO: 4) or (SEQ ID NO: 32).

In another very preferred embodiment, said amino acid sequence (I) is selected from any one of (SEQ ID NO: 2), (SEQ ID NO: 3), (SEQ ID NO: 4), (SEQ ID NO: 5), (SEQ ID NO: 21), (SEQ ID NO: 24), (SEQ ID NO: 25), (SEQ ID NO: 26), (SEQ ID NO: 27), (SEQ ID NO: 32), (SEQ ID NO: 33), or (SEQ ID NO: 34).

In another very preferred embodiment, said amino acid sequence (I) is selected from any one of (SEQ ID NO: 2), (SEQ ID NO: 3), (SEQ ID NO: 4), (SEQ ID NO: 21), (SEQ ID NO: 24), (SEQ ID NO: 25), (SEQ ID NO: 32), (SEQ ID NO: 33), or (SEQ ID NO: 34).

In another very preferred embodiment, said amino acid sequence (I) is selected from any one of (SEQ ID NO: 2), (SEQ ID NO: 3), (SEQ ID NO: 4), (SEQ ID NO: 5), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), or (SEQ ID NO: 36).

In another very preferred embodiment, said amino acid sequence (I) is selected from any one of (SEQ ID NO: 2), (SEQ ID NO: 3), (SEQ ID NO: 4), (SEQ ID NO: 21), (SEQ ID NO: 22), (SEQ ID NO: 23), (SEQ ID NO: 24), (SEQ ID NO: 25), (SEQ ID NO: 28), (SEQ ID NO: 29 (SEQ ID NO: 32), (SEQ ID NO: 33), (SEQ ID NO: 34), (SEQ ID NO: 35), or (SEQ ID NO: 36).

In another very preferred embodiment, said amino acid sequence (I) is SEQ ID NO: 2.

In another very preferred embodiment, said amino acid sequence (I) is SEQ ID NO: 3.

In another very preferred embodiment, said amino acid sequence (I) is SEQ ID NO: 4.

In another very preferred embodiment, said amino acid sequence (I) is SEQ ID NO: 5.

In another very preferred embodiment, said amino acid sequence (I) is SEQ ID NO: 21.

In another very preferred embodiment, said amino acid sequence (I) is SEQ ID NO: 22.

In another very preferred embodiment, said amino acid sequence (I) is SEQ ID NO: 23.

In another very preferred embodiment, said amino acid sequence (1) is SEQ ID NO: 24.

In another very preferred embodiment, said amino acid sequence (I) is SEQ ID NO: 25.

In another very preferred embodiment, said amino acid sequence (I) is SEQ ID NO: 26.

In another very preferred embodiment, said amino acid sequence (I) is SEQ ID NO: 27.

In another very preferred embodiment, said amino acid sequence (I) is SEQ ID NO: 28.

In another very preferred embodiment, said amino acid sequence (I) is SEQ ID NO: 29.

In another very preferred embodiment, said amino acid sequence (I) is SEQ ID NO: 30).

In another very preferred embodiment, said amino acid sequence (I) is SEQ ID NO: 31.

In another very preferred embodiment, said amino acid sequence (I) is SEQ ID NO: 32.

In another very preferred embodiment, said amino acid sequence (I) is SEQ ID NO: 33.

In another very preferred embodiment, said amino acid sequence (I) is SEQ ID NO: 34.

In another very preferred embodiment, said amino acid sequence (I) is SEQ ID NO: 35.

In another very preferred embodiment, said amino acid sequence (I) is SEQ ID NO: 36.

In another very preferred embodiment, said amino acid sequence (I) is SEQ ID NO: 39.

In another very preferred embodiment, said amino acid sequence (I) is SEQ ID NO: 40.

In another very preferred embodiment, said amino acid sequence (I) is SEQ ID NO: 41.

In another very preferred embodiment, said amino acid sequence (I) is SEQ ID NO: 42.

In another very preferred embodiment, said amino acid sequence (I) is SEQ ID NO: 43.

In another very preferred embodiment, said amino acid sequence (I) is SEQ ID NO: 44.

In another very preferred embodiment, said amino acid sequence (I) is SEQ ID NO: 45.

In another very preferred embodiment, said amino acid sequence (I) is SEQ ID NO: 46.

In another very preferred embodiment, said amino acid sequence (I) is SEQ ID NO: 47.

In another very preferred embodiment, said amino acid sequence (I) is SEQ ID NO: 48.

In another very preferred embodiment, said amino acid sequence (I) is SEQ ID NO: 49.

In another very preferred embodiment, said amino acid sequence (I) is SEQ ID NO: 50.

In another very preferred embodiment, said amino acid sequence (I) is SEQ ID NO: 51.

In another very preferred embodiment, said amino acid sequence (I) is SEQ ID NO: 52.

In another very preferred embodiment, said amino acid sequence (I) is SEQ ID NO: 53.

In another very preferred embodiment, said amino acid sequence (I) is SEQ ID NO: 54.

In another very preferred embodiment, said amino acid sequence (I) is SEQ ID NO: 55.

In another very preferred embodiment, said amino acid sequence (I) is SEQ ID NO: 56.

In another very preferred embodiment, said amino acid sequence (I) is SEQ ID NO: 57. In a certain embodiment, said amino acid sequence (I) of the cyclic peptide of the invention comprises (i) an N-terminus selected from a free amino group or an acetylated N-terminus, and/or (ii) a C-terminus selected from a free carboxyl group or an amidated C-terminus.

In another preferred embodiment, said cyclic peptide further comprises a linker, wherein said linker is attached to said amino acid sequence (I), and wherein said linker comprises (i) at least one attachment moiety, (ii) at least one spacer moiety, (iii) at least one linking moiety, or (iv) any combination of (i), (ii) and (iii).

In another preferred embodiment, said cyclic peptide further comprises a linker, wherein said linker is attached to said amino acid sequence (I), and wherein said linker comprises (i) one attachment moiety, (ii) one spacer moiety, (iii) one linking moiety, or (iv) any combination of (i), (ii) and (iii).

In another preferred embodiment, said at least one attachment moiety comprises or preferably consists of —O—$NH_2$, —O—NH— (an aminooxy moiety), —C(O)—$CH_2$—O—$NH_2$, —C(O)—$CH_2$—O—NH— (aminooxy acetyl moiety), —NH—$NH_2$, —NH—NH— (hydrazine moiety), -E(O)—NH—$NH_2$, or -E(O)—NH—NH— (hydrazide moiety), wherein E is C, S(O) or P. In a further preferred embodiment, said attachment moiety comprises or preferably consists of an —O—$NH_2$, —O—NH— (an aminooxy moiety), —C(O)—$CH_2$—O—$NH_2$, —C(O)—$CH_2$—O—NH— (aminooxy acetyl moiety), —NH—$NH_2$, —NH—NH— (hydrazine moiety), or (—C(O)—NH—$NH_2$, —C(O)—NH—NH-(carbohydrazide moiety). In another further preferred embodiment, said attachment moiety comprises or preferably consists of —O—$NH_2$ or —O—NH— (an aminooxy moiety).

In another preferred embodiment, said at least one spacer moiety comprises or preferably consists of $NH_2$—$CH_2$—$CH_2$—(O—$CH_2$—$CH_2$)$_n$—C(O)— or —NH—$CH_2$—$CH_2$—(O—$CH_2$—$CH_2$)$_n$—C(O)—, wherein n is an integer of 1 to 45, preferably 2 to 20, more preferably 6 to 8; or $NH_2$—$(CH_2)_m$—C(O)— or —NH—$(CH_2)_m$—C(O)—, wherein m is an integer of 2 to 45, preferably 2 to 20, more preferably 2 to 6.

In another preferred embodiment, said at least one linking moiety is capable of cross-linking the cyclic peptide with a second peptide. Linking moieties capable of cross-linking a cyclic peptide with a second peptide are well known in the art. In one embodiment of the invention, said linking moiety capable of cross-linking the cyclic peptide with a second peptide comprises or consists of an aldehyde moiety, such as a glutaraldehyde moiety, octanedialdehyde moiety, dialdehyde moiety, succinaldehyde moiety; carbodiimide moiety, such as 1-ethyl-3-(3-dimethylaminopropyl)carbodiimide hydrochloride moiety; glyoxol moiety; N-hydroxy-sulphosuccinimidyl moiety, such as N-hydroxy-sulphosuccinimidyl moiety; a cationic linking moiety; polyethyleneglycol moiety; benzoyl benzoic acid moiety. Further suitable linking moieties are listed in the Pierce Catalog and Handbook, Pierce Chemical Company, Rockford (1997); Bioconjugate Techniques, Greg T. Hermanson, Pierce Biotechnology, Thermo Fisher Scientific, Rockford (2013); and are described in EP 1321466 A1, DE 19821859 A1, U.S. Pat. Nos. 6,875,737, 5,456,911, 5,612,036, 5,965,532, WO 2001004135, WO 2001070685, US 20140302001 A1, U.S. Pat. No. 6,800,728, US 20140171619 A1, U.S. Pat. No. 8,168,190, WO 2012/166594 A1 and WO 2015/082501.

In one embodiment, said linker is at least one, preferably exactly one attachment moiety. In another embodiment, said linker is at least one, preferably exactly one, two or three spacer moieties, wherein in case of more than one spacer moiety, they are preferably linked together, either directly or via an interconnecting group. In another embodiment, said linker is at least one, preferably exactly one spacer moiety. In another embodiment, said linker is at least one, preferably exactly one linking moiety.

In another embodiment, said linker comprises at least one, preferably exactly one attachment moiety and at least one, preferably exactly one, two or three spacer moieties, further preferably exactly one spacer moiety. In another embodiment, said linker comprises at least one, preferably exactly one attachment moiety and at least one, preferably exactly one linking moiety. In another embodiment, said linker comprises at least one, preferably exactly one, two or three spacer moieties, further preferably exactly one spacer moiety, and at least one, preferably exactly one linking moiety. In another embodiment, said linker comprises at least one, preferably exactly one attachment moiety and at least one, preferably exactly one, two or three spacer moieties, further preferably exactly one spacer moiety, and at least one, preferably exactly one linking moiety.

In another embodiment, said linker comprises at least one attachment moiety and at least one, preferably exactly one spacer moiety, wherein the at least one attachment moiety is attached to the N-terminus of said amino acid sequence (I), and the at least one spacer moiety is attached to the attachment moiety.

In another embodiment, said linker comprises at least one attachment moiety and at least one, preferably exactly one spacer moiety wherein the at least one spacer moiety is attached to the N-terminus of said amino acid sequence (I), and the at least one attachment moiety is attached to the spacer moiety.

In another embodiment, said at least one linker comprises at least one attachment moiety and at least one linking moiety, wherein the at least one attachment moiety is attached to the N-terminus of said amino acid sequence (I), and the least one linking moiety is attached to the attachment moiety. In another embodiment, said at least one linker comprises at least one spacer moiety and at least one linking moiety, wherein the at least one spacer moiety is attached to the N-terminus of said amino acid sequence (I), and the at least one linking moiety is attached to the at least one spacer moiety.

In one embodiment, said at least one linker comprises at least one attachment moiety and at least one spacer moiety and at least one linking moiety, wherein the at least one linking moiety or the at least one spacer moiety is attached to the N-terminus of said amino acid sequence (I). In another embodiment, the at least one attachment moiety is attached to the N-terminus of said amino acid sequence (I), the at least one spacer moiety is attached to the attachment moiety and the at least one linking moiety is attached to the spacer moiety. In another embodiment, the at least one spacer moiety is attached to the N-terminus of the amino acid sequence (I), the at least one attachment moiety is attached to the spacer moiety and the at least one linking moiety is attached to the attachment moiety.

In a preferred embodiment, the linker is attached to the amino acid sequence (I) typically and preferably via an amide bond to the N-terminus of said amino acid sequence (I) or to a free amino group of a side chain of an amino acid of said amino acid sequence (I), preferably to the N-terminus of said amino acid sequence (I).

In a preferred embodiment, said linking moiety is capable of cross-linking said cyclic peptide with a thiol group of a second peptide. In a preferred embodiment, said linking moiety comprises a maleimide moiety.

In a preferred embodiment, said linker is attached to an amino group included in said amino acid sequence (I), wherein preferably said linker is attached to a free amino group of (i) the N-terminus of said amino acid sequence (I), or (ii) a side chain of an amino acid of said amino acid sequence (I). Preferably, the linker is attached to said amino group included in said amino acid sequence (I) by an amide bond. Said side chain is preferably of the amino acid lysine. In a preferred embodiment, X24 is lysine and said linker is attached to the free amino group of the side chain of X24.

In a very preferred embodiment, said linker is selected from the following formulas:

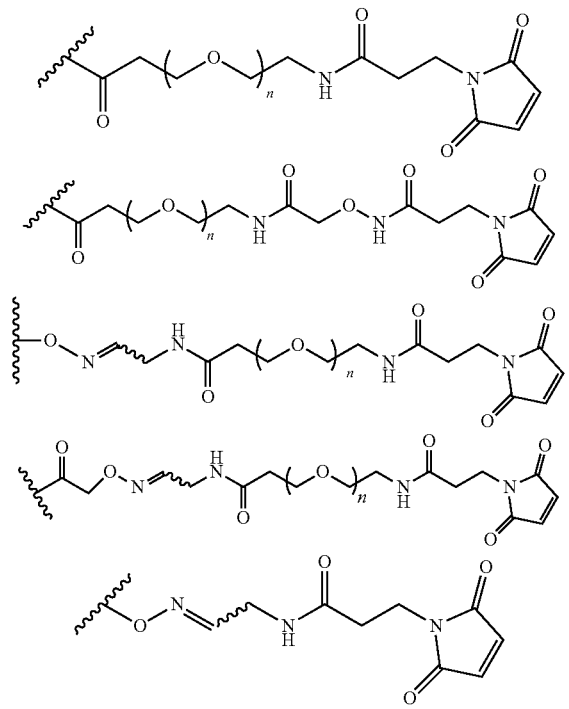

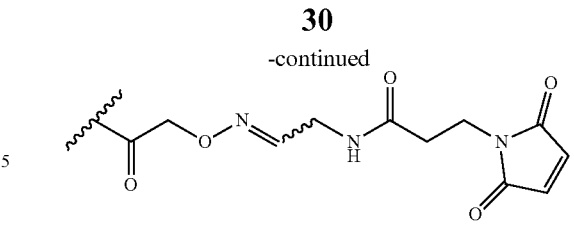

wherein n is an integer of 1 to 45, preferably 6 to 8, and the wavy line indicates the attachment site to said amino acid sequence (I).

In case the compounds of the present invention such as the cyclic peptide or the conjugate, and hereby including the linker of the present invention, comprise one or more double bonds, said double bonds can be of either the (E)- or (Z)-configuration, or mixtures thereof in any ratio. The same applies for the preferred linker of the present invention comprising an oxime moiety. Thus, the preferred linker of the present invention comprising an oxime moiety thus may include either said linker with said oxime moiety in its syn-configuration (and thus as syn-isomer), said linker with said oxime moiety in its anti-configuration (and thus as anti-isomer) and mixtures thereof in any ratio. Within the chemical formulas presented herein for said double bond or said oxime moiety, this is typically and preferably represented by a wavy line.

In a further very preferred embodiment, said linker is selected from the following formulas:

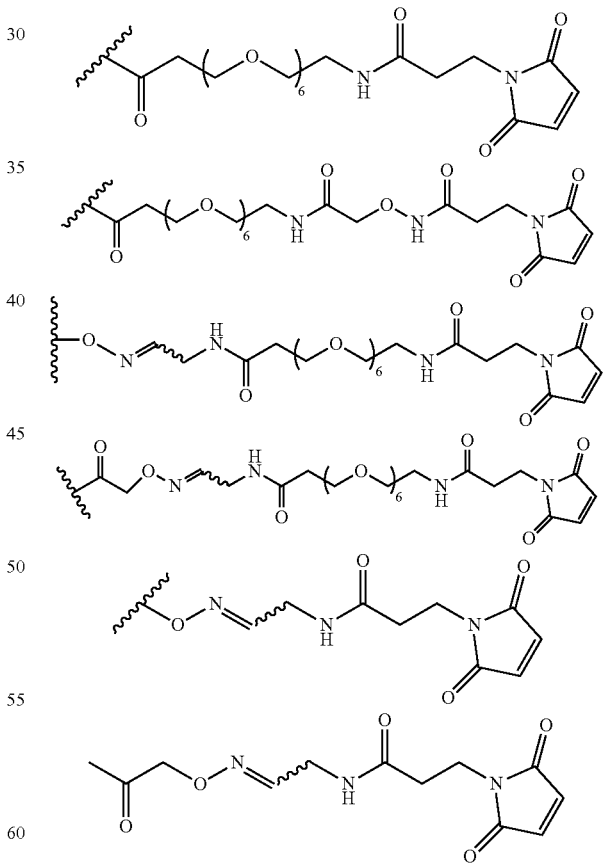

wherein the wavy line indicates the attachment site to said amino acid sequence (I).

In a further very preferred embodiment, said cyclic peptide comprises, preferably is, a formula selected from any one of following formulas:

(3) (SEQ ID NO: 16)

H₂N-O-CH₂-C(=O)-NH-(CH₂-CH₂-O)₆-CH₂-CH₂-C(=O)-NSECLSLCND-Nle-PITNDQKKLCSN-Dab-CQSVRa-NH₂,
[bond between residues shown]

(4) (SEQ ID NO: 17)

AOAc-NSECLSLCND-Nle-PITNDQKKLCSN-Dab-CQSRVa-NH₂, (5) (SEQ ID NO: 18)

Ac-NSECLSLCND-Nle-PITNDQKKLCSN-Lys-(AOAc)-CQSRVa-NH₂, (6) (SEQ ID NO: 19)

AOAc-RLSECLSLCND-Nle-PITNDQKKLCSNNCLKSa-NH₂,  or (7) (SEQ ID NO: 20)

AOAc-PVSTYMLTNSECLSLCNDMPITNDQKKLCSNNCQIVRQQa-NH₂.

In a further very preferred embodiment, said cyclic peptide comprises, preferably is, a formula selected from any one of formulas (3) (SEQ ID NO: 16), formula (4) (SEQ ID NO: 17), formula (5) (SEQ ID NO: 18), formula (6) (SEQ ID NO: 19), formula (7) (SEQ ID NO: 20), formula (19)

AOAc-NSECLSLCND-Nle-PITNDQKKLCSS-Dab-CQSVRa-NH₂ with SEQ ID NO: 39 formula (20)

AOAc-NSECLSLCND-Nle-PITNDQKKLCSSNCQSVRa-NH₂, with SEQ ID NO: 40 formula (21)

AOAc-NSECLSLCND-Nle-PITNDQKKLCSSQCQSVRa-NH₂, with SEQ ID NO: 41 formula (22)

AOAc-NSECLSLCND-Nle-PITNDQKKLCSSSCQSVRa-NH₂, with SEQ ID NO: 42 formula (23)

AOAc-QSECLSLCND-Nle-PITNDQKKLCSN-Dab-CQSVRa-NH₂, with SEQ ID NO: 43 formula (24)

AOAc-QSECLSLCND-Nle-PITNDQKKLCSS-Dab-CQSVRa-NH₂, with SEQ ID NO: 44 formula (25)

AOAc-QSECLSLCND-Nle-PITNDQKKLCSSNCQSVRa-NH₂, with SEQ ID NO: 45

formula (26)

AOAc-QSECLSLCND-Nle-PITNDQKKLCSSCQSVRa-NH$_2$, with SEQ ID NO: 46

formula (27)

AOAc-QSECLSLCND-Nle-PITNDQKKLCSSSCQSVRa-NH$_2$, with SEQ ID NO: 47

formula (28)

AOAc-SSECLSLCND-Nle-PITNDQKKLCSN-Dab-CQSVRa-NH$_2$, with SEQ ID NO: 48

formula (29)

AOAc-SSECLSLCND-Nle-PITNDQKKLCSS-Dab-CQSVRa-NH$_2$, with SEQ ID NO: 49

formula (30)

AOAc-SSECLSLCND-Nle-PITNDQKKLCSSNCQSVRa-NH$_2$, with SEQ ID NO: 50

formula (31)

AOAc-SSECLSLCND-Nle-PITNDQKKLCSSQCQSVRa-NH$_2$, with SEQ ID NO: 51

formula (32)

AOAc-SSECLSLCND-Nle-PITNDQKKLCSSSCQSVRa-NH$_2$, with SEQ ID NO: 52

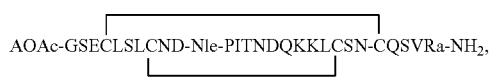

formula (33)

AOAc-GSECLSLCND-Nle-PITNDQKKLCSN-CQSVRa-NH$_2$, with SEQ ID NO: 53

formula (34)

AOAc-GSECLSLCND-Nle-PITNDQKKLCSS-Dab-CQSVRa-NH$_2$, with SEQ ID NO: 54

formula (35)

AOAc-GSECLSLCND-Nle-PITNDQKKLCSSNCQSVRa-NH$_2$, with SEQ ID NO: 55

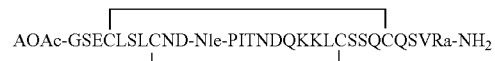

formula (36)

AOAc-GSECLSLCND-Nle-PITNDQKKLCSSQCQSVRa-NH$_2$ with SEQ ID NO: 56 or

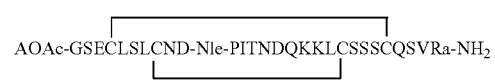

formula (37)

AOAc-GSECLSLCND-Nle-PITNDQKKLCSSSCQSVRa-NH$_2$ with SEQ ID NO: 57.

In a further very preferred embodiment, said cyclic peptide comprises, preferably is, formula (3) (SEQ ID NO: 16). In a further very preferred embodiment, said cyclic peptide comprises, preferably is, formula (4) (SEQ ID NO: 17). In a further very preferred embodiment, said cyclic peptide comprises, preferably is, formula (5) (SEQ ID NO: 18). In a further very preferred embodiment, said cyclic peptide comprises, preferably is, formula (6) (SEQ ID NO: 19). In a further very preferred embodiment, said cyclic peptide comprises, preferably is, formula (7) (SEQ ID NO: 20). In a further very preferred embodiment, said cyclic peptide comprises, preferably is, formula (19). In a further very preferred embodiment, said cyclic peptide comprises, preferably is, formula (20). In a further very preferred embodiment, said cyclic peptide comprises, preferably is, formula (21). In a further very preferred embodiment, said cyclic peptide comprises, preferably is, formula (22). In a further very preferred embodiment, said cyclic peptide comprises, preferably is, formula (23). In a further very preferred embodiment, said cyclic peptide comprises, preferably is, formula (24). In a further very preferred embodiment, said cyclic peptide comprises, preferably is, formula (25). In a further very preferred embodiment, said cyclic peptide comprises, preferably is, formula (26). In a further very preferred embodiment, said cyclic peptide comprises, preferably is, formula (27). In a further very preferred embodiment, said cyclic peptide comprises, preferably is, formula (28). In a further very preferred embodiment, said cyclic peptide comprises, preferably is, formula (29). In a further very preferred embodiment, said cyclic peptide comprises, preferably is, formula (30). In a further very preferred embodiment, said cyclic peptide comprises, preferably is, formula (31). In a further very preferred embodiment, said cyclic peptide comprises, preferably is, formula (32). In a further very preferred embodiment, said cyclic peptide comprises, preferably is, formula (33). In a further very preferred embodiment, said cyclic peptide comprises, preferably is, formula (34). In a further very preferred embodiment, said cyclic peptide comprises, preferably is, formula (35). In a further very preferred embodiment, said cyclic peptide comprises, preferably is, formula (36). In a further very preferred embodiment, said cyclic peptide comprises, preferably is, formula (37).

In another aspect, the present invention provides for a conjugate comprising (a) a lipopeptide building block, and (b) the inventive cyclic peptide, wherein said lipopeptide building block consists of (i) a peptide moiety comprising at least one coiled coil peptide chain segment, and (ii) a lipid moiety comprising two or three, preferably two hydrocarbyl chains; and wherein said cyclic peptide is connected, directly or via a linker, to said lipopeptide building block.

In another aspect, the present invention provides for a conjugate comprising (a) a lipopeptide building block, and (b) a cyclic peptide, wherein said lipopeptide building block consists of (i) a peptide moiety comprising at least one coiled coil peptide chain segment, and (ii) a lipid moiety comprising two or three, preferably two hydrocarbyl chains; and wherein said cyclic peptide is connected, directly or via a linker, to said lipopeptide building block, and wherein said cyclic peptide comprises an amino acid sequence (I), wherein said amino acid sequence (I) comprises, preferably consists of, the amino acid sequence:

X1-X2-X3-C4-X5-X6-X7-C8-X9-X10-X11-P12-I13-
T14-N15-D16-Q17-K18-K19-L20-C21-X22-
X23-X24-C25-X26-X27-X28-X29-X30 (SEQ ID NO: 1), wherein X1, X2, X3, X5, X6, X7, X9, X10, X11, X22, X23, X24, X26, X27, X28 and X29 are independently of each other an amino acid;
C4, C8, C21 and C25 are independently of each other cysteine;
P12 is proline;
I13 is isoleucine;
T14 is threonine;
N15 is asparagine;
D16 is aspartic acid;
Q17 is glutamine;
K18 and K19 are independently of each other lysine;
L20 is leucine; and
X30 is an amino acid or a deletion,
wherein said cysteines C4 and C25 form a first disulfide bond and said cysteines C8 and C21 form a second disulfide bond.

Conjugation procedures that may be used to attach the cyclic peptide to the lipopeptide building block are well known to those skilled in the art (see for example Hermanson, G. T, Bioconjugate Techniques, 2nd edition, Academic Press, 2008). Any method used for conjugating peptides or other antigens to an antigen delivery system, such as carrier protein, polymer, dendrimer, nanoparticle or virus-like particle, can be used to conjugate said cyclic peptide to said lipopeptide building block. Free amino groups in the side chains of amino acids in the peptide moiety of the lipopeptide building block may be coupled to reactive esters in the cyclic peptide or the linker (e.g. N-hydroxysuccinimide esters prepared from carboxylic acids); thiols in the peptide moiety may be coupled to maleimide groups in the linker; azides may be incorporated into the side chains of amino acid residues in the peptide moiety and coupled to the cyclic peptide or linker containing acetylene groups using copper catalyzed cycloaddition reactions; and other nucleophiles (e.g. hydrazino, hydroxyl amino, vic-amino thiol groups) in the peptide moiety may be coupled to electrophiles (e.g. aldehydes, ketones. active esters) in the cyclic peptide or linker. It will be obvious that it is possible, in principle, to reverse the positions of the two reactive groups in the peptide moiety and cyclic peptide or linker in order to achieve selective coupling.

All embodiments and preferred and very preferred embodiments of the inventive cyclic peptide described herein are applicable to all aspects of the present invention, especially to the aspect of the conjugate of the invention comprising an inventive cyclic peptide, even though not all embodiments and preferred and very preferred embodiments of the inventive cyclic peptide are again repeated.

In a preferred embodiment, said cyclic peptide has a length of at most 80 amino acids. In a further preferred embodiment, said cyclic peptide has a length of at most 60 amino acids. In a further preferred embodiment, said cyclic peptide has a length of at most 40 amino acids. In a further preferred embodiment, said cyclic peptide has a length of at most 30 amino acids.

In a preferred embodiment, said X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide, wherein preferably X11 is norleucine.

In another preferred embodiment, said X23 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, or cysteine-s-acetamide, wherein preferably X23 is asparagine.

In another preferred embodiment, said X23 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine. In another preferred embodiment, said X23 is selected from serine, homoserine, allo-threonine, 3,3-dihydroxy-alanine, 2-amino-5-hydroxypentanoic acid, 4-hydroxy-l-threonine, threonine, hydroxynorvaline, and 6-hydroxy-l-norleucine. In another preferred embodiment, said X23 is selected from glutamine, glycine, asparagine or serine. In another preferred embodiment, said X23 is selected from glutamine, glycine or serine. In another preferred embodiment, said X23 is asparagine or serine. In a further preferred embodiment, said X23 is serine. In a further preferred embodiment, said X23 is glutamine. In a further preferred embodiment, said X23 is glycine. In a further preferred embodiment, said X23 is asparagine.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; aspartic acid, 2-amino-6-oxopimelic acid, 3-methyl-aspartic acid, l-2-amino-6-methylene-pimelic acid, 4-hydroxy-glutamic-acid, 6-carboxylysine, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, or cysteine-s-acetamide.

In another preferred embodiment, said X24 is selected from lysine, 2,4-diaminobutyric acid, 2,3-diaminopropanoic acid, 2,8-diaminooctanoic acid, ornithine, amino-adipic acid or thialysine.

In another preferred embodiment, said X24 is selected from 2-amino-6-oxopimelic acid, 3-methyl-aspartic acid, l-2-amino-6-methylene-pimelic acid, 4-hydroxy-glutamic-acid, 6-carboxylysine, aspartic acid, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid. More preferably, X24 is selected of 3-methyl-aspartic acid, 6-carboxylysine, aspartic acid, beta-hydroxyaspartic acid, 3,3-dimethyl aspartic acid, or 2-amino-propanedioic acid.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, aspartic acid or thialysine, wherein preferably X24 is selected from lysine, 2,4-diaminobutyric acid, 2,3-diaminopropanoic acid, 2,8-diaminooctanoic acid, ornithine, amino-adipic acid, asparagine, thialysine or aspartic acid.

In another preferred embodiment, X24 is selected from lysine, 2,4-diaminobutyric acid, asparagine, ornithine or aspartic acid. In another preferred embodiment, X24 is selected from lysine, 2,4-diaminobutyric acid, aspartic acid or asparagine. In another more preferred embodiment, X24 is selected from lysine, 2,4-diaminobutyric acid or asparagine. In another preferred embodiment, X24 is lysine. In another preferred embodiment, X24 is 2,4-diaminobutyric acid. In another preferred embodiment, X24 is asparagine. In another preferred embodiment, X24 is aspartic acid. In another preferred embodiment, X24 is ornithine. In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; aspartic acid, 2-amino-6-oxopimelic acid, 3-methyl-aspartic acid, l-2-amino-6-methylene-pimelic acid, 4-hydroxy-glutamic-acid, 6-carboxylysine, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate, 2-aminoadipic acid; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, said X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, X24 is selected from glutamine, glutamine hydroxamate, 3-methyl-glutamine, n5-methyl-glutamine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

In another preferred embodiment, X24 is selected from asparagine, lysine, ornithine, 2,4-diaminobutyric acid (Dab), glutamine, glycine or serine. In another preferred embodiment, X24 is glycine, glutamine or serine. In another preferred embodiment, X24 is glutamine or serine. In another preferred embodiment, X24 is serine. In another preferred embodiment, X24 is glutamine. In another preferred embodiment, X24 is glycine.

In another preferred embodiment, X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide, and X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide, lysine, 2,4-diaminobutyric acid, 2,3-diaminopropanoic acid, 2,8-diaminooctanoic acid, ornithine, amino-adipic acid, aspartic acid or thialysine, wherein preferably X24 is selected from lysine, 2,4-diaminobutyric acid, 2,3-diaminopropanoic acid, 2,8-diaminooctanoic acid, ornithine, amino-adipic acid, asparagine, aspartic acid or thialysine. In another preferred embodiment, X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide; and X24 is selected from lysine, 2,4-diaminobutyric acid or asparagine, preferably X24 is lysine or 2,4-diaminobutyric acid.

In another preferred embodiment, X11 is norleucine, and X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide, lysine, 2,4-diaminobutyric acid, 2,3-diaminopropanoic acid, 2,8-diaminooctanoic acid, ornithine, amino-adipic acid, aspartic acid or thialysine, wherein preferably X24 is selected from lysine, 2,4-diaminobutyric acid, 2,3-diaminopropanoic acid, 2,8-diaminooctanoic acid, ornithine, amino-adipic acid, asparagine, aspartic acid or thialysine.

In a preferred embodiment, X11 is norleucine and X24 is lysine, 2,4-diaminobutyric acid, aspartic acid, ornithine or asparagine, preferably X24 is ornithine, aspartic acid, lysine or 2,4-diaminobutyric. In another preferred embodiment, X11 is norleucine and X24 is ornithine, aspartic acid, 2,4-diaminobutyric acid or asparagine. In another preferred embodiment, X11 is norleucine and X24 is ornithine, lysine, asparagine, or aspartic acid. In a preferred embodiment, X11 is norleucine and X24 is selected from ornithine, lysine, 2,4-diaminobutyric acid or asparagine. In a preferred embodiment, X11 is norleucine and X24 is selected from lysine, 2,4-diaminobutyric acid, aspartic acid or asparagine.

In another preferred embodiment, X11 is norleucine and X24 is selected from lysine, 2,4-diaminobutyric acid, aspartic acid, ornithine, serine, glutamine, glycine or asparagine, preferably X24 is selected from ornithine, aspartic acid, lysine or 2,4-diaminobutyric. In another preferred embodiment, X11 is norleucine and X24 is selected from 2,4-diaminobutyric acid, aspartic acid, ornithine serine, glutamine, glycine or asparagine. In another preferred embodiment, X11 is norleucine and X24 is selected from ornithine, lysine, asparagine, serine, glutamine, glycine or aspartic acid. In another preferred embodiment, X11 is norleucine and X24 is selected from ornithine, lysine, 2,4-diaminobutyric acid, serine, glutamine, glycine or asparagine. In another preferred embodiment, X11 is norleucine and X24 is selected from lysine, 2,4-diaminobutyric acid, aspartic acid, serine, glutamine, glycine or asparagine. In another preferred embodiment, X11 is norleucine and X24 is selected from serine, glutamine, glycine or asparagine. In another preferred embodiment, X11 is norleucine and X24 is selected from serine, glutamine, or glycine. In another preferred embodiment, X11 is norleucine and X24 is selected from serine, or glutamine. In another preferred embodiment, X11 is norleucine and X24 is selected from serine, or glutamine. In another preferred embodiment, X11 is norleucine and X24 is serine. In another preferred embodiment, X11 is norleucine and X24 is glutamine. In another preferred embodiment, X11 is norleucine and X24 is asparagine.

In another preferred embodiment, X11 is norleucine and is aspartic acid, lysine or 2,4-diaminobutyric. In another preferred embodiment, X11 is norleucine and X24 is aspartic acid, 2,4-diaminobutyric acid or asparagine. In another preferred embodiment, X11 is norleucine and X24 is aspartic acid, 2,4-diaminobutyric acid or ornithine. In another preferred embodiment, X11 is norleucine and X24 is lysine, asparagine, or aspartic acid. In another preferred embodiment, X11 is norleucine and X24 is lysine, asparagine, or ornithine. In another preferred embodiment, X11 is norleucine and X24 is lysine, ornithine or aspartic acid. In another preferred embodiment, X11 is norleucine and X24 is ornithine, asparagine, or aspartic acid. In a preferred embodiment, X11 is norleucine and X24 is selected from lysine, 2,4-diaminobutyric acid or asparagine. In a preferred embodiment, X11 is norleucine and X24 is selected from lysine, 2,4-diaminobutyric acid or ornithine. In a preferred embodiment, X11 is norleucine and X24 is selected from asparagine, 2,4-diaminobutyric acid or ornithine.

In another preferred embodiment, X11 is norleucine and X24 is selected from aspartic acid, lysine, 2,4-diaminobutyric acid, serine, glutamine, or glycine. In another preferred embodiment, X11 is norleucine and X24 is selected from aspartic acid, 2,4-diaminobutyric acid, asparagine, serine, glutamine, or glycine. In another preferred embodiment, X11 is norleucine and X24 is selected from aspartic acid, 2,4-diaminobutyric acid, ornithine, serine, glutamine, or glycine. In another preferred embodiment, X11 is norleucine and X24 is selected from lysine, asparagine, aspartic acid, serine, glutamine, or glycine. In another preferred embodiment, X11 is norleucine and X24 is selected from lysine, asparagine, ornithine, serine, glutamine, or glycine. In another preferred embodiment, X11 is norleucine and X24 is selected from lysine, ornithine, aspartic acid, serine, glutamine, or glycine. In another preferred embodiment, X11 is norleucine and X24 is selected from ornithine, asparagine, or aspartic acid. In a preferred embodiment, X11 is norleucine and X24 is selected from lysine, 2,4-diaminobutyric acid, asparagine, serine, glutamine, or glycine. In a preferred embodiment, X11 is norleucine and X24 is selected from lysine, 2,4-diaminobutyric acid, ornithine, serine, glutamine, or glycine. In a preferred embodiment, X11 is norleucine and X24 is selected from asparagine, 2,4-diaminobutyric acid, ornithine, serine, glutamine, or glycine.

In a more preferred embodiment, X11 is norleucine and X24 is lysine or 2,4-diaminobutyric. In another preferred embodiment, X11 is norleucine and X24 is 2,4-diaminobutyric acid or asparagine. In another preferred embodiment, X11 is norleucine and X24 is 2,4-diaminobutyric acid or aspartic acid. In another preferred embodiment, X11 is norleucine and X24 is 2,4-diaminobutyric acid or ornithine. In another preferred embodiment, X11 is norleucine and X24 is lysine or asparagine. In another preferred embodiment, X11 is norleucine and X24 is lysine or ornithine. In another preferred embodiment, X11 is norleucine and X24 is aspartic acid or lysine. In another preferred embodiment, X11 is norleucine and X24 is aspartic acid or asparagine. In another preferred embodiment, X11 is norleucine and X24 is ornithine or asparagine. In another preferred embodiment, X11 is norleucine and X24 is aspartic acid or ornithine.

In a more preferred embodiment, X11 is norleucine and X24 is selected from lysine, 2,4-diaminobutyric, serine, glutamine, or glycine. In another preferred embodiment, X11 is norleucine and X24 is selected from 2,4-diaminobutyric acid, asparagine, serine, glutamine, or glycine. In another preferred embodiment, X11 is norleucine and X24 is selected from 2,4-diaminobutyric acid, aspartic acid, serine, glutamine, or glycine. In another preferred embodiment, X11 is norleucine and X24 is selected from 2,4-diaminobutyric acid, ornithine, serine, glutamine, or glycine. In another preferred embodiment, X11 is norleucine and X24 is selected from lysine, asparagine, serine, glutamine, or glycine. In another preferred embodiment, X11 is norleucine and X24 is selected from lysine, ornithine, serine, glutamine, or glycine. In another preferred embodiment, X11 is norleucine and X24 is selected from aspartic acid, lysine, serine, glutamine, or glycine. In another preferred embodiment, X11 is norleucine and X24 is selected from aspartic acid, asparagine, serine, glutamine, or glycine. In another preferred embodiment, X11 is norleucine and X24 is selected from ornithine, asparagine, serine, glutamine, or glycine. In another preferred embodiment, X11 is norleucine and X24 is selected from aspartic acid, ornithine, serine, glutamine, or glycine.

In another preferred embodiment, X11 is norleucine and X24 is aspartic acid. In another preferred embodiment, X11 is norleucine and X24 is asparagine. In another preferred embodiment, X11 is norleucine and X24 is ornithine. In another preferred embodiment, X11 is norleucine and X24 is 2,4-diaminobutyric acid. In another preferred embodiment, X11 is norleucine and X24 is lysine.

In another preferred embodiment, X11 is norleucine and X24 is selected from aspartic acid, ornithine, serine, glutamine, or glycine. In another preferred embodiment, X11 is norleucine and X24 is selected from asparagine, ornithine, serine, glutamine, or glycine. In another preferred embodiment, X11 is norleucine and X24 is selected from ornithine, serine, glutamine, or glycine. In another preferred embodiment, X11 is norleucine and X24 is selected from 2,4-diaminobutyric acid, ornithine, serine, glutamine, or glycine. In another preferred embodiment, X11 is norleucine and X24 is selected from lysine, ornithine, serine, glutamine, or glycine.

In another preferred embodiment, X11 is norleucine, X24 is ornithine, aspartic acid, 2,4-diaminobutyric acid, lysine or asparagine, and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another more preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid.

In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another more preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid.

In another preferred embodiment, X11 is norleucine, X24 is selected from serine, glutamine, glycine, or asparagine, preferably from serine, glutamine, or glycine; and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid; preferably, said C-terminal amino acid of said amino acid sequence (I) is a D-stereoisomer. In another more preferred embodiment, X11 is norleucine, X24 is selected from serine, glutamine, glycine, or asparagine, preferably from serine, glutamine, or glycine; and said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid; preferably, said C-terminal amino acid of said amino acid sequence (I) is a D-stereoisomer.

In another preferred embodiment, X11 is norleucine, X24 is ornithine, aspartic acid, 2,4-diaminobutyric acid, lysine or asparagine, and said C-terminal amino acid of said amino acid sequence (I) is a D-amino acid. In another preferred embodiment, X11 is norleucine, X24 is ornithine, aspartic acid, 2,4-diaminobutyric acid, lysine or asparagine, and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is a D-amino acid. In another preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is ornithine, aspartic acid, 2,4-diaminobutyric acid, lysine or asparagine, and said C-terminal amino acid of said amino acid sequence (I) is alanine, preferably D-alanine. In another more preferred embodiment, X11 is norleucine, X24 is 2,4-diaminobutyric acid, lysine or asparagine, more preferably X24 is 2,4-diaminobutyric acid or lysine and said C-terminal amino acid of said amino acid sequence (I) is alanine, preferably D-alanine.

In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is a D-amino acid. In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is a D-amino acid. In another preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is selected from a D-stereoisomer of alanine, leucine, valine, norleucine, norvaline, isoleucine, homoleucine, vinylglycine, 2-aminobutyric acid, 2-allylglycine, alloleucine, alloisoleucine, or 2-aminoheptanoic acid. In another preferred embodiment, X11 is norleucine, X24 is selected from serine, glutamine, glycine, ornithine, aspartic acid, 2,4-diaminobutyric acid, lysine or asparagine, and said C-terminal amino acid of said amino acid sequence (I) is alanine, preferably D-alanine. In another more preferred embodiment, X11 is norleucine, X24 is selected from serine, glutamine, glycine, 2,4-diaminobutyric acid, lysine or asparagine, more preferably X24 is selected from serine, glutamine, glycine, 2,4-diaminobutyric acid or lysine and said C-terminal amino acid of said amino acid sequence (I) is alanine, preferably D-alanine.

In another preferred embodiment, said X1 is a polar or hydrophobic amino acid. Preferably, X1 is selected of asparagine, beta-hydroxyasparagine, 2,5-diamino-4-hydroxy-5-oxopentanoic acid, glutamine, glutamine hydroxamate, 3-methyl-l-glutamine, n-methyl-asparagine, n5-methyl-glutamine, cysteine-s-acetamide; leucine, alloleucine, alloisoleucine, homoleucine, isoleucine, 2-aminobutyric acid, norleucine, norvaline or valine. In another more preferred embodiment, X1 is asparagine or leucine. In another again more preferred embodiment, X1 is asparagine. In another again more preferred embodiment, X1 is leucine.

In another preferred embodiment, said X1 is selected from asparagine, beta-hydroxyasparagine, 2,5-diamino-4-hydroxy-5-oxopentanoic acid, glutamine, glutamine hydroxamate, 3-methyl-l-glutamine, n-methyl-asparagine, n5-methyl-glutamine, cysteine-s-acetamide; leucine, alloleucine, alloisoleucine, homoleucine, isoleucine, 2-aminobutyric acid, norleucine, norvaline, valine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine; or glycine.

In another preferred embodiment, said X1 is selected from glutamine; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine; or glycine. In another preferred embodiment, said X1 is selected from serine, homoserine, allo-threonine, 3,3-dihydroxy-alanine, 2-amino-5-hydroxypentanoic acid, 4-hydroxy-l-threonine, threonine, hydroxynorvaline, or 6-hydroxy-l-norleucine.

In another preferred embodiment, said X1 is selected from asparagine, glutamine, leucine, serine, or glycine. In another preferred embodiment, said X1 is selected from asparagine, glutamine, serine, or glycine. In another preferred embodiment, said X1 is selected from asparagine, or serine. In another preferred embodiment, said X1 is selected from asparagine, or glutamine. In another preferred embodiment, said X1 is selected from glutamine, serine, or glycine. In another preferred embodiment, said X1 is glycine. In another preferred embodiment, said X1 is glutamine. In another preferred embodiment, said X1 is serine.

In another preferred embodiment, said X1, X23 and X24 are each independently selected from the group consisting of ornithine, aspartic acid, lysine, asparagine, 2,4-diaminobutyric acid (Dab), glutamine, leucine, serine, and glycine. In another preferred embodiment, said X1, X23 and X24 are each independently selected from the group consisting of asparagine, 2,4-diaminobutyric acid (Dab), glutamine, leucine, serine, and glycine. In another preferred embodiment, said X1, X23 and X24 are each independently selected from the group consisting of asparagine, glutamine, serine, and glycine. In another preferred embodiment, said X1, X23 and X24 are each independently selected from the group consisting of glutamine, serine, and glycine. In another preferred embodiment, said X1 is selected from asparagine, glutamine, leucine, serine, or glycine; said X23 is selected from asparagine or serine; and said X24 is selected from asparagine, 2,4-diaminobutyric acid (Dab), glutamine, or serine. In another preferred embodiment, said X1 is selected from glutamine, serine, or glycine; said X23 is serine; and said X24 is glutamine or serine.

In another preferred embodiment, said X2, X6 and X22 are independently of each other a polar amino acid. Preferably, X2, X6 and X22 are independently of each other selected of 2-amino-5-hydroxypentanoic acid, allo-threonine, 4-chloro-threonine, 3,3-dihydroxy-alanine, 4-hydroxy-L-isoleucine, (2s,3r)-2-amino-3-hydroxy-4-methylpentanoic acid, beta-hydroxy-leucine, homoserine, 3-hydroxy-l-valine, 4,5-dihydroxy-isoleucine, 6-hydroxy-l-norleucine, s-(2-hydroxyethyl)-1-cysteine, phosphoserine, serine, 4-hydroxy-l-threonine, threonine, phosphothreonine or hydroxynorvaline. Again more preferably, X2, X6 and X22 are independently of each other serine. In another preferred embodiment, X2 and X6 are serine. In another preferred embodiment, X6 and X22 are serine. In another preferred embodiment, X2 and X22 are serine. In another preferred embodiment, X2, X6 and X22 are serine.

In another preferred embodiment, said X3 is an amino acid having an acidic or negatively charged side chain at a physiological pH (about pH 7). Preferably, X3 is selected of glutamate, 5-o-methyl-glutamic acid, (3r)-3-methyl-l-glutamic acid, (3s)-3-methyl-l-glutamic acid, 2s,4r-4-methylglutamate, 4-hydroxy-glutamic-acid, 2-aminoadipic acid, 1-2-amino-6-methylene-pimelic acid, 2-amino-6-oxopimelic acid; 3-methyl-aspartic acid, 6-carboxylysine, aspartic acid, beta-hydroxyaspartic acid, 3,3-dimethyl aspartic acid, or 2-amino-propanedioic acid. More preferably, X3 is selected of glutamate, 5-o-methyl-glutamic acid, (3r)-3-methyl-l-glutamic acid, (3s)-3-methyl-l-glutamic acid, 2s,4r-4-methylglutamate, 4-hydroxy-glutamic-acid, 2-aminoadipic acid, 1-2-amino-6-methylene-pimelic acid or 2-amino-6-oxopimelic acid. In another again more preferred embodiment, X3 is glutamate.

In another preferred embodiment, said X5 and X7 are independently of each other a hydrophobic amino acid. Preferably, X5 and X7 are independently of each other selected of leucine, alloleucine, alloisoleucine, homoleucine, isoleucine, 2-aminobutyric acid, norleucine, norvaline or valine. More preferably, X5 or X7 is leucine. In another more again preferred embodiment, X5 and X7 are leucine.

In another preferred embodiment, said X9 and X23 are independently of each other a polar amino acid. Preferably, X9 and X23 are independently of each other selected of asparagine, beta-hydroxyasparagine, 2,5-diamino-4-hydroxy-5-oxopentanoic acid, glutamine, glutamine hydroxamate, 3-methyl-l-glutamine, n-methyl-asparagine, n5-methyl-glutamine or cysteine-s-acetamide. In another more preferred embodiment, X9 or X23 is asparagine. In another again more preferred embodiment, X9 and X23 are asparagine.

Preferably, X9 and X23 are independently of each other selected of asparagine, glutamine, serine or glycine. In another more preferred embodiment, X9 or X23 is selected from asparagine, glutamine, serine or glycine. In another again more preferred embodiment, X9 and X23 are both selected from asparagine, glutamine, serine or glycine.

In another preferred embodiment, said X10 is an amino acid having an acidic or negatively charged side chain at a physiological pH (about pH 7). Preferably, X10 is selected of 2-amino-6-oxopimelic acid, 3-methyl-aspartic acid, 1-2-amino-6-methylene-pimelic acid, 4-hydroxy-glutamic-acid, 6-carboxylysine, aspartic acid, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate or 2-aminoadipic acid. More preferably, X10 is selected of 3-methyl-aspartic acid, 6-carboxylysine, aspartic acid, beta-hydroxyaspartic acid, 3,3-dimethyl aspartic acid, or 2-amino-propanedioic acid. In another again more preferred embodiment, X10 is aspartic acid.

In another preferred embodiment, said X26 is a hydrophobic or polar amino acid. Preferably, X is selected of leucine, alloleucine, alloisoleucine, homoleucine, isoleucine, 2-aminobutyric acid, norleucine, norvaline, valine; 2,5-diamino-4-hydroxy-5-oxopentanoic acid, glutamine hydroxamate, 3-methyl-l-glutamine, n5-methyl-glutamine, asparagine, 2,5-diamino-4-hydroxy-5-oxopentanoic acid, or n-methyl-asparagine. More preferably, X26 is leucine or glutamine.

In another preferred embodiment, said X27 is a polar or hydrophobic amino acid or an amino acid having an acidic or negatively charged side chain at a physiological pH (about pH 7). Preferably, X27 is selected of selected of 2-amino-5-hydroxypentanoic acid, allo-threonine, 4-chloro-threonine, 3,3-dihydroxy-alanine, 4-hydroxy-L-isoleucine, (2s,3r)-2-amino-3-hydroxy-4-methylpentanoic acid, betahydroxy-leucine, homoserine, 3-hydroxy-l-valine, 4,5-dihydroxy-isoleucine, 6-hydroxy-l-norleucine, s-(2-hydroxyethyl)-1-cysteine, phosphoserine, serine, 4-hydroxy-l-threonine, threonine, phosphothreonine, hydroxynorvaline; leucine, alloleucine, alloisoleucine, homoleucine, isoleucine, 2-aminobutyric acid, norleucine, norvaline, valine; diaminobutyric acid, 2,3-diaminopropanoic acid, (2s)-2,8-diaminooctanoic acid, lysine, ornithine, or thialysine. More preferably, X27 is serine, isoleucine, or lysine In another preferred embodiment, said X28 is a polar or hydrophobic amino acid. Preferably, X28 is selected of 2-amino-5-hydroxypentanoic acid, allo-threonine, 4-chloro-threonine, 3,3-dihydroxy-alanine, 4-hydroxy-L-isoleucine, (2s,3r)-2-amino-3-hydroxy-4-methylpentanoic acid, beta-hydroxy-leucine, homoserine, 3-hydroxy-l-valine, 4,5-dihydroxy-isoleucine, 6-hydroxy-l-norleucine, s-(2-hydroxyethyl)-1-cysteine, phosphoserine, serine, 4-hydroxy-l-threonine, threonine, phosphothreonine, hydroxynorvaline; leucine, alloleucine, alloisoleucine, homoleucine, isoleucine, 2-aminobutyric acid, norleucine, norvaline, or valine. More preferably, X28 is valine or serine.

In another preferred embodiment, said X29 is a hydrophobic amino acid or an amino acid having a negatively charged side chain at physiological pH (about pH 7). Preferably, X29 is selected of the D- or L-stereoisomer, preferably the D-stereoisomer of 2-allyl-glycine, 2-aminobutyric acid, 2-aminoheptanoic acid, alanine, tertleucine, diethylalanine, homoleucine, 3-methyl-l-alloisoleucine, allo-isoleucine, isoleucine, leucine, vinylglycine, norleucine, norvaline, valine; 5-methyl-arginine, arginine, c-gamma-hydroxy arginine, citrulline, 2-amino-4-guanidinobutryric acid, 2-amino-3-guanidinopropionic acid, canavanine, homoarginine, or thio-citrulline. In another preferred embodiment, X29 is D- or L-alanine or D- or L-arginine. In another more preferred embodiment, X29 is D-alanine or D-arginine.

In another preferred embodiment, said X30 is a deletion or a hydrophobic or polar D- or L-amino acid, preferably X30 is a hydrophobic or polar amino acid D-amino acid. Preferably, X30 is a deletion or X30 is selected of the D- or L-stereoisomer, preferably the D-stereoisomer of 2-allyl-glycine, 2-aminobutyric acid, 2-aminoheptanoic acid, alanine, tertleucine, diethylalanine, homoleucine, 3-methyl-l-alloisoleucine, allo-isoleucine, isoleucine, leucine, vinylglycine, norleucine, norvaline, valine; 2,5-diamino-4-hydroxy-5-oxopentanoic acid, glutamine hydroxamate, 3-methyl-l-glutamine, n5-methyl-glutamine, asparagine, 2,5-diamino-4-hydroxy-5-oxopentanoic acid, or n-methyl-asparagine. In another preferred embodiment, X30 is D- or L-glutamine or D- or L-alanine. In another more preferred embodiment, X30 is D-glutamine or D-alanine. In another again more preferred embodiment, X30 is D-alanine.

In a preferred embodiment, X30 is a deletion and X29 is alanine, preferably D-alanine. In another preferred embodiment, X30 is alanine, preferably D-alanine and X29 is arginine.

In another preferred embodiment, X1 is asparagine or leucine, X2 is serine, and X3 is glutamate.

In another preferred embodiment, X1 is serine, glycine, glutamine, asparagine or leucine, X2 is serine, and X3 is glutamate. In another preferred embodiment, X1 is serine, asparagine or leucine, X2 is serine, and X3 is glutamate. In another preferred embodiment, X1 is serine, X2 is serine, and X3 is glutamate.

In another preferred embodiment, X5 is leucine, X6 is serine, and X7 is leucine.

In another preferred embodiment, X9 is asparagine, X10 is aspartic acid and X11 is norleucine or methionine, preferably X11 is norleucine.

In another preferred embodiment, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X22 is serine, X23 is selected from asparagine, serine, glycine or glutamine, and X24 is selected from serine, glycine, glutamine, Dab (2,4-diaminobutyric acid), asparagine or lysine. In another preferred embodiment, X22 is serine, and X23 and X24 are selected from glutamine, glycine, serine, or asparagine.

In another preferred embodiment, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, and X7 is leucine. In another preferred embodiment, X1 is asparagine or leucine, X2 is serine, X3 is glutamate, X9 is asparagine, X10 is aspartic acid and X11 is norleucine or methionine, preferably X11 is norleucine. In another preferred embodiment, X1 is asparagine or leucine, X2 is serine, X3 is glutamate, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, and X7 is leucine. In another preferred embodiment, X1 is asparagine or leucine, X2 is serine, X3 is glutamate, X9 is asparagine, X10 is aspartic acid and X11 is norleucine or methionine, preferably X11 is norleucine. In another preferred embodiment, X1 is asparagine or leucine, X2 is serine, X3 is glutamate, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X5 is leucine, X6 is serine, X7 is leucine, X9 is asparagine, X10 is aspartic acid and X11 is norleucine or methionine, preferably X11 is norleucine. In another preferred embodiment, X5 is leucine, X6 is serine, X7 is leucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X5 is leucine, X6 is serine, X7 is leucine, X22 is serine, X23 is selected from asparagine, serine, glycine, glutamine, and X24 is selected from serine, glycine, glutamine, Dab (2,4-diaminobutyric acid), asparagine or lysine, preferably X24 and X23 are asparagine, serine, glycine, or glutamine. In another preferred embodiment, X5 is leucine, X6 is serine, X7 is leucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X9 is asparagine, X10 is aspartic acid, X11 is norleucine or methionine, preferably X11 is norleucine, X22 is serine, X23 is serine, glycine, glutamine, asparagine, and X24 is selected from serine, glycine, glutamine, Dab (2,4-diaminobutyric acid), asparagine or lysine, preferably X23 and X24 are selected from serine, glycine, glutamine, asparagine. In another preferred embodiment, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is a deletion, D- or L-alanine, more preferably X30 is D-alanine.

In another preferred embodiment, X22 is serine, X23 is asparagine, X24 is Dab (2,4-diaminobutyric acid), asparagine or lysine, preferably X24 is Dab (2,4-diaminobutyric acid) or lysine, X26 is glutamine or leucine, X27 is serine, lysine or isoleucine, X28 is valine X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X22 is serine, X23 is asparagine, serine, glycine, glutamine, X24 is serine, glycine, glutamine, Dab (2,4-diaminobutyric acid), asparagine or lysine, X26 is glutamine or leucine, X27 is serine, lysine or isoleucine, X28 is valine X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, X7 is leucine, X9 is asparagine, X10 is aspartic acid, and X11 is norleucine or methionine, preferably X11 is norleucine. In another preferred embodiment, X1 is asparagine or leucine, X2 is serine, X3 is glutamate, X5 is leucine, X6 is serine, X7 is leucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X5 is leucine, X6 is serine, X7 is leucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is serine, glycine, glutamine asparagine or leucine, X2 is serine, X3 is glutamate, X5 is leucine, X6 is serine, X7 is leucine, X9 is asparagine, X10 is aspartic acid, and X11 is norleucine or methionine, preferably X11 is norleucine. In another preferred embodiment, X1 is serine, glycine, glutamine, asparagine or leucine, X2 is serine, X3 is glutamate, X5 is leucine, X6 is serine, X7 is leucine, X22 is serine, X23 is serine, glycine, glutamine, asparagine, and X24 is serine, glycine, glutamine Dab (2,4-diaminobutyric acid), asparagine or lysine. In another preferred embodiment, X1 is serine, glycine, glutamine, asparagine or leucine, X2 is serine, X3 is glutamate, X5 is leucine, X6 is serine, X7 is leucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X1 is asparagine or leucine, X2 is serine, X3 is glutamate, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is a deletion, D- or L-alanine, more preferably X30 is D-alanine.

In another preferred embodiment, X1 is selected from serine, glycine, glutamine, asparagine or leucine, X2 is serine, X3 is glutamate, X9 is asparagine, X10 is aspartic acid, X11 is norleucine or methionine, preferably X11 is norleucine, X22 is serine, X23 is selected from serine, glycine, glutamine, asparagine, and X24 is selected from serine, glycine, glutamine, Dab (2,4-diaminobutyric acid), asparagine or lysine. In another preferred embodiment, X1 is selected from serine, glycine, glutamine, asparagine or leucine, X2 is serine, X3 is glutamate, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is a deletion, D- or L-alanine, more preferably X30 is D-alanine.

In another preferred embodiment, X5 is leucine, X6 is serine, X7 is leucine, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine. In another preferred embodiment, X5 is leucine, X6 is serine, X7 is leucine, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is D- or L-alanine or D- or L-glutamine, preferably X30 is D- or L-alanine, more preferably X30 is D-alanine. In another preferred embodiment, X5 is leucine, X6 is serine, X7 is leucine, X22 is serine, X23 is asparagine, X24 is Dab (2,4-diaminobutyric acid), asparagine or lysine, preferably X24 is Dab (2,4-diaminobutyric acid) or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine. In another preferred embodiment, X9 is asparagine, X10 is aspartic acid, X11 is norleucine or methionine, preferably X11 is norleucine, X22 is serine, X23 is asparagine, X24 is Dab (2,4-diaminobutyric acid), asparagine or lysine, preferably X24 is Dab (2,4-diaminobutyric acid) or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X5 is leucine, X6 is serine, X7 is leucine, X9 is asparagine, X10 is aspartic acid, X11 is norleucine or methionine, preferably X11 is norleucine, X22 is serine, X23 is selected from serine, glycine, glutamine, asparagine, and X24 is selected from serine, glycine, glutamine, Dab (2,4-diaminobutyric acid), ornithine, aspartic acid, asparagine or lysine. In another preferred embodiment, X5 is leucine, X6 is serine, X7 is leucine, X22 is serine, X23 is selected from serine, glycine, glutamine, asparagine, X24 is selected from serine, glycine, glutamine, ornithine, aspartic acid, Dab (2,4-diaminobutyric acid), asparagine or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine. In another preferred embodiment, X9 is asparagine, X10 is aspartic acid, X11 is norleucine or methionine, preferably X11 is norleucine, X22 is serine, X23 is selected from serine, glycine, glutamine, asparagine, X24 is selected from serine, glycine, glutamine, ornithine, aspartic acid, Dab (2,4-diaminobutyric acid), asparagine or lysine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X22 is serine, X23 is asparagine, and X24 is Dab (2,4-diaminobutyric acid), asparagine or lysine, preferably X24 is Dab (2,4-diaminobutyric acid) or lysine.

In another preferred embodiment, X1 is selected from glutamine, serine, glycine, asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X22 is serine, X23 is selected from glutamine, serine, glycine, asparagine, and X24 is selected from glutamine, serine, glycine, ornithine, aspartic acid, Dab (2,4-diaminobutyric acid), asparagine or lysine. In another preferred embodiment, X1 is asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, X1 is selected from glutamine, serine, glycine, asparagine or leucine, X2 is serine, X3 is glutamate, X5 is leucine, X6 is serine, X7 is leucine, X9 is asparagine, X10 is aspartic acid, X11 is norleucine or methionine, preferably X11 is norleucine, X26 is glutamine or leucine, X27 is serine, lysine or isoleucine, X28 is valine, X29 is D- or L-arginine or D- or L-alanine, preferably X29 is D- or L-alanine, more preferably X29 is D-alanine, and X30 is a deletion, D- or L-alanine or D- or L-glutamine, preferably X30 is D- or L-alanine, more preferably X30 is D-alanine.

In another preferred embodiment, said C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, or 2-aminoheptanoic acid.

In a certain embodiment, the C-terminal amino acid of said amino acid sequence (I) is a D-amino acid, preferably said C-terminal amino acid is selected from D-alanine, D-leucine, D-valine, D-norleucine, D-norvaline, D-isoleucine, D-homoleucine, D-vinylglycine, D-2-aminobutyric acid, D-2-allylglycine, D-alloleucine, D-alloisoleucine, or D-2-aminoheptanoic acid.

In a preferred embodiment, said X2, X3, X5, X6, X7, X9, X10, X11, X22, X23, X24, X26, X27, X28 and X29 are independently of each other L-amino acids.

In a preferred embodiment proline P12, isoleucine I13, threonine T14, asparagine N15, aspartic acid D16, glutamine Q17, lysines K18 and K19, and leucine L20 are independently of each other L-amino acids.

In a preferred embodiment, C4, C8, C21 and C25 are independently of each other D-cysteine or L-cysteine, preferably L-cysteine.

In a preferred embodiment, the cyclic peptide of the invention consists of said amino acid sequence (I). In another preferred embodiment, said amino acid sequence (I) consists of said amino acid sequence of SEQ ID NO: 1.

In another very preferred embodiment, said amino acid sequence of SEQ ID NO: 1 is an amino acid selected from:

```
                                            (SEQ ID NO: 2)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Dab-
Cys-Gln-Ser-Val-Arg-ala, (SEQ ID NO: 3)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Lys-
Cys-Gln-Ser-Val-Arg-ala, (SEQ ID NO: 21)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Asn-
Cys-Gln-Ser-Val-Arg-ala, (SEQ ID NO: 22)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Asp-
Cys-Gln-Ser-Val-Arg-ala
or (SEQ ID NO: 23)
Asn-Ser-Glu-Cys-Leu-Ser-Leu-Cys-Asn-Asp-Nle-Pro-
Ile-Thr-Asn-Asp-Gln-Lys-Lys-Leu-Cys-Ser-Asn-Orn-
Cys-Gln-Ser-Val-Arg-ala.
```

In another very preferred embodiment, said amino acid sequence of SEQ ID NO: 1 is an amino acid selected from SEQ ID NO: 2 or SEQ ID NO: 3.

In another very preferred embodiment, said amino acid sequence of SEQ ID NO: 1 is selected from any one of SEQ ID NO: 2-5, 21-36, or

```
SEQ ID NO: 39:
NSECLSLCND-Nle-PITNDQKKLCSS-Dab-CQSVRa,

SEQ ID NO: 40:
NSECLSLCND-Nle-PITNDQKKLCSSNCQSVRa,

SEQ ID NO: 41:
NSECLSLCND-Nle-PITNDQKKLCSSQCQSVRa,

SEQ ID NO: 42:
NSECLSLCND-Nle-PITNDQKKLCSSSCQSVRa,

SEQ ID NO: 43:
QSECLSLCND-Nle-PITNDQKKLCSN-Dab-CQSVRa,

SEQ ID NO: 44:
QSECLSLCND-Nle-PITNDQKKLCSS-Dab-CQSVRa,

SEQ ID NO: 45:
QSECLSLCND-Nle-PITNDQKKLCSSNCQSVRa,

SEQ ID NO: 46:
QSECLSLCND-Nle-PITNDQKKLCSSQCQSVRa,

SEQ ID NO: 47:
QSECLSLCND-Nle-PITNDQKKLCSSSCQSVRa,

SEQ ID NO: 48:
SSECLSLCND-Nle-PITNDQKKLCSN-Dab-CQSVRa,

SEQ ID NO: 49:
SSECLSLCND-Nle-PITNDQKKLCSS-Dab-CQSVRa,

SEQ ID NO: 50:
SSECLSLCND-Nle-PITNDQKKLCSSNCQSVRa,

SEQ ID NO: 51:
SSECLSLCND-Nle-PITNDQKKLCSSQCQSVRa,

SEQ ID NO: 52:
SSECLSLCND-Nle-PITNDQKKLCSSSCQSVRa,

SEQ ID NO: 53:
GSECLSLCND-Nle-PITNDQKKLCSN-Dab-CQSVRa,

SEQ ID NO: 54:
GSECLSLCND-Nle-PITNDQKKLCSS-Dab-CQSVRa,

SEQ ID NO: 55:
GSECLSLCND-Nle-PITNDQKKLCSSNCQSVRa,

SEQ ID NO: 56:
GSECLSLCND-Nle-PITNDQKKLCSSQCQSVRa,
or

SEQ ID NO: 57:
GSECLSLCND-Nle-PITNDQKKLCSSSCQSVRa.
```

In another very preferred embodiment, said amino acid sequence of SEQ ID NO: 1 is the amino acid of SEQ ID NO: 2. In another very preferred embodiment, said amino acid sequence of SEQ ID NO: 1 is the amino acid of SEQ ID NO: 3. In another very preferred embodiment, said amino acid sequence of SEQ ID NO: 1 is the amino acid of SEQ ID NO: 21. In another very preferred embodiment, said amino acid sequence of SEQ ID NO: 1 is the amino acid of SEQ ID NO: 22. In another very preferred embodiment, said amino acid sequence of SEQ ID NO: 1 is the amino acid of SEQ ID NO: 23. In another very preferred embodiment, said amino acid sequence of SEQ ID NO: 1 is the amino acid of SEQ ID NO: 39. In another very preferred embodiment, said amino acid sequence of SEQ ID NO: 1 is the amino acid of SEQ ID NO: 40. In another very preferred embodiment, said amino acid sequence of SEQ ID NO: 1 is the amino acid of SEQ ID NO: 41. In another very preferred embodiment, said amino acid sequence of SEQ ID NO: 1 is the amino acid of SEQ ID NO: 42. In another very preferred embodiment, said amino acid sequence of SEQ ID NO: 1 is the amino acid of SEQ ID NO: 43. In another very preferred embodiment, said amino acid sequence of SEQ ID NO: 1 is the amino acid of SEQ ID NO: 44. In another very preferred embodiment, said amino acid sequence of SEQ ID NO: 1 is the amino acid of SEQ ID NO: 45. In another very preferred embodiment, said amino acid sequence of SEQ ID NO: 1 is the amino acid of SEQ ID NO: 46. In another very preferred embodiment, said amino acid sequence of SEQ ID NO: 1 is the amino acid of SEQ ID NO: 47. In another very preferred embodiment, said amino acid sequence of SEQ ID NO: 1 is the amino acid of SEQ ID NO: 48. In another very preferred embodiment, said amino acid sequence of SEQ ID NO: 1 is the amino acid of SEQ ID NO: 49. In another very preferred embodiment, said amino acid sequence of SEQ ID NO: 1 is the amino acid of SEQ ID NO: 50. In another very preferred embodiment, said amino acid sequence of SEQ ID NO: 1 is the amino acid of SEQ ID NO: 51. In another very preferred embodiment, said amino acid sequence of SEQ ID NO: 1 is the amino acid of SEQ ID NO: 52. In another very preferred embodiment, said amino acid sequence of SEQ ID NO: 1 is the amino acid of SEQ ID NO: 53. In another very preferred embodiment, said amino acid sequence of SEQ ID NO: 1 is the amino acid of SEQ ID NO: 54. In another very preferred embodiment, said amino acid sequence of SEQ ID NO: 1 is the amino acid of SEQ ID NO: 55. In another very preferred embodiment, said amino acid sequence of SEQ ID NO: 1 is the amino acid of SEQ ID NO: 56. In another very preferred embodiment, said amino acid sequence of SEQ ID NO: 1 is the amino acid of SEQ ID NO: 57.

In another very preferred embodiment, said amino acid sequence (I) is selected from:

```
                                         (SEQ ID NO: 2)
Asn-Ser-Glu-Cys-Leu-Ser-Leu-Cys-Asn-Asp-Nle-Pro-

Ile-Thr-Asn-Asp-Gln-Lys-Lys-Leu-Cys-Ser-Asn-Dab-

Cys-Gln-Ser-Val-Arg-ala, (SEQ ID NO: 3)
Asn-Ser-Glu-Cys-Leu-Ser-Leu-Cys-Asn-Asp-Nle-Pro- Ile-Thr-Asn-Asp-Gln-Lys-Lys-Leu-Cys-Ser-Asn-Lys- Cys-Gln-Ser-Val-Arg-ala, (SEQ ID NO: 4)
Arg-Leu-Ser-Glu-Cys-Leu-Ser-Leu-Cys-Asn-Asp-Nle- Pro-Ile-Thr-Asn-Asp-Gln-Lys-Lys-Leu-Cys-Ser-Asn- Asn-Cys-Leu-Lys-Ser-ala, (SEQ ID NO: 5)
Pro-Val-Ser-Thr-Tyr-Met-Leu-Thr-Asn-Ser-Glu-Cys- Leu-Ser-Leu-Cys-Asn-Asp-Met-Pro-Ile-Thr-Asn-Asp- Gln-Lys-Lys-Leu-Cys-Ser-Asn-Asn-Cys-Gln-Ile-Val- Arg-Gln-Gln-ala,
```

(SEQ ID NO: 21)
Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Asn-Cys-Gln-Ser-Val-Arg-ala, (SEQ ID NO: 22)
Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Asp-Cys-Gln-Ser-Val-Arg-ala, (SEQ ID NO: 23)
Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Orn-Cys-Gln-Ser-Val-Arg-ala, (SEQ ID NO: 24)
Arg-Leu-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Lys-Cys-Leu-Lys-Ser-ala, (SEQ ID NO: 25)
Arg-Leu-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Dab-Cys-Leu-Lys-Ser-ala, (SEQ ID NO: 26)
Pro-Val-Ser-Thr-Tyr-Met-Leu-Thr-Asn-Ser-Glu-Cys-Leu-Ser-Leu-Cys-Asn-Asp-Met-Pro-Ile-Thr-Asn-Asp-Gln-Lys-Lys-Leu-Cys-Ser-Asn-Lys-Cys-Gln-Ile-Val-Arg-Gln-Gln-ala, (SEQ ID NO: 27)
Pro-Val-Ser-Thr-Tyr-Met-Leu-Thr-Asn-Ser-Glu-Cys-Leu-Ser-Leu-Cys-Asn-Asp-Met-Pro-Ile-Thr-Asn-Asp-Gln-Lys-Lys-Leu-Cys-Ser-Asn-Dab-Cys-Gln-Ile-Val-Arg-Gln-Gln-ala, (SEQ ID NO: 28)
Arg-Leu-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Asp-Cys-Leu-Lys-Ser-ala, (SEQ ID NO: 29)
Arg-Leu-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Orn-Cys-Leu-Lys-Ser-ala, (SEQ ID NO: 30)
Pro-Val-Ser-Thr-Tyr-Met-Leu-Thr-Asn-Ser-Glu-Cys-Leu-Ser-Leu-Cys-Asn-Asp-Met-Pro-Ile-Thr-Asn-Asp-Gln-Lys-Lys-Leu-Cys-Ser-Asn-Asp-Cys-Gln-Ile-Val-Arg-Gln-Gln-ala, (SEQ ID NO: 31)
Pro-Val-Ser-Thr-Tyr-Met-Leu-Thr-Asn-Ser-Glu-Cys-Leu-Ser-Leu-Cys-Asn-Asp-Met-Pro-Ile-Thr-Asn-Asp-Gln-Lys-Lys-Leu-Cys-Ser-Asn-Orn-Cys-Gln-Ile-Val-Arg-Gln-Gln-ala, (SEQ ID NO: 32)
Pro-Val-Ser-Thr-Tyr-Met-Leu-Thr-Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Asn-Cys-Gln-Ile-Val-Arg-Gln-Gln-ala, (SEQ ID NO: 33)
Pro-Val-Ser-Thr-Tyr-Met-Leu-Thr-Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Lys-Cys-Gln-Ile-Val-Arg-Gln-Gln-ala, or (SEQ ID NO: 34)
Pro-Val-Ser-Thr-Tyr-Met-Leu-Thr-Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Dab-Cys-Gln-Ile-Val-Arg-Gln-Gln-ala.

(SEQ ID NO: 35)
Pro-Val-Ser-Thr-Tyr-Met-Leu-Thr-Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Asp-Cys-Gln-Ile-Val-Arg-Gln-Gln-ala, or (SEQ ID NO: 36)
Pro-Val-Ser-Thr-Tyr-Met-Leu-Thr-Asn-Ser-Glu-Cys-Leu-Ser-Leu-Cys-Asn-Asp-Nle-Pro-Ile-Thr-Asn-Asp-Gln-Lys-Lys-Leu-Cys-Ser-Asn-Orn-Cys-Gln-Ile-Val-Arg-Gln-Gln-ala.

In another very preferred embodiment, said amino acid sequence (I) is selected from any one of (SEQ ID NO: 2), (SEQ ID NO: 3), (SEQ ID NO: 4), (SEQ ID NO: 5) or (SEQ ID NO: 32).

In another very preferred embodiment, said amino acid sequence (I) is selected from any one of (SEQ ID NO: 2), (SEQ ID NO: 3), (SEQ ID NO: 4) or (SEQ ID NO: 32).

In another very preferred embodiment, said amino acid sequence (I) is selected from any one of (SEQ ID NO: 2), (SEQ ID NO: 3), (SEQ ID NO: 4), (SEQ ID NO: 5), (SEQ ID NO: 21), (SEQ ID NO: 24), (SEQ ID NO: 25), (SEQ ID NO: 26), (SEQ ID NO: 27), (SEQ ID NO: 32), (SEQ ID NO: 33), or (SEQ ID NO: 34).

In another very preferred embodiment, said amino acid sequence (I) is selected from any one of (SEQ ID NO: 2), (SEQ ID NO: 3), (SEQ ID NO: 4), (SEQ ID NO: 21), (SEQ ID NO: 24), (SEQ ID NO: 25), (SEQ ID NO: 32), (SEQ ID NO: 33), or (SEQ ID NO: 34).

In another very preferred embodiment, said amino acid sequence (I) is selected from any one of (SEQ ID NO: 2), (SEQ ID NO: 3), (SEQ ID NO: 4), (SEQ ID NO: 5), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), or (SEQ ID NO: 36).

In another very preferred embodiment, said amino acid sequence (I) is selected from any one of (SEQ ID NO: 2), (SEQ ID NO: 3), (SEQ ID NO: 4), (SEQ ID NO: 21), (SEQ ID NO: 22), (SEQ ID NO: 23), (SEQ ID NO: 24), (SEQ ID NO: 25), (SEQ ID NO: 28), (SEQ ID NO: 29 (SEQ ID NO: 32), (SEQ ID NO: 33), (SEQ ID NO: 34), (SEQ ID NO: 35), or (SEQ ID NO: 36). In another very preferred embodiment, said amino acid sequence (I) is selected from any one of SEQ ID NO: 2-5, 21-36, or SEQ ID NO: 39-57.

In another very preferred embodiment, said amino acid sequence (I) is SEQ ID NO: 2.

In another very preferred embodiment, said amino acid sequence (I) is SEQ ID NO: 3.

In another very preferred embodiment, said amino acid sequence (I) is SEQ ID NO: 4.

In another very preferred embodiment, said amino acid sequence (I) is SEQ ID NO: 5.

In another very preferred embodiment, said amino acid sequence (I) is SEQ ID NO: 21.

In another very preferred embodiment, said amino acid sequence (I) is SEQ ID NO: 22.

In another very preferred embodiment, said amino acid sequence (I) is SEQ ID NO: 23.

In another very preferred embodiment, said amino acid sequence (I) is SEQ ID NO: 24.

In another very preferred embodiment, said amino acid sequence (I) is SEQ ID NO: 25.

In another very preferred embodiment, said amino acid sequence (I) is SEQ ID NO: 26.

In another very preferred embodiment, said amino acid sequence (I) is SEQ ID NO: 27.

In another very preferred embodiment, said amino acid sequence (I) is SEQ ID NO: 28.

In another very preferred embodiment, said amino acid sequence (I) is SEQ ID NO: 29.

In another very preferred embodiment, said amino acid sequence (I) is SEQ ID NO: 30).

In another very preferred embodiment, said amino acid sequence (I) is SEQ ID NO: 31.

In another very preferred embodiment, said amino acid sequence (I) is SEQ ID NO: 32.

In another very preferred embodiment, said amino acid sequence (I) is SEQ ID NO: 33.

In another very preferred embodiment, said amino acid sequence (I) is SEQ ID NO: 34.

In another very preferred embodiment, said amino acid sequence (I) is SEQ ID NO: 35.

In another very preferred embodiment, said amino acid sequence (I) is SEQ ID NO: 36.

In another very preferred embodiment, said amino acid sequence (I) is SEQ ID NO: 39.

In another very preferred embodiment, said amino acid sequence (I) is SEQ ID NO: 40.

In another very preferred embodiment, said amino acid sequence (I) is SEQ ID NO: 41.

In another very preferred embodiment, said amino acid sequence (I) is SEQ ID NO: 42.

In another very preferred embodiment, said amino acid sequence (I) is SEQ ID NO: 43.

In another very preferred embodiment, said amino acid sequence (I) is SEQ ID NO: 44.

In another very preferred embodiment, said amino acid sequence (I) is SEQ ID NO: 45.

In another very preferred embodiment, said amino acid sequence (I) is SEQ ID NO: 46.

In another very preferred embodiment, said amino acid sequence (I) is SEQ ID NO: 47.

In another very preferred embodiment, said amino acid sequence (I) is SEQ ID NO: 48.

In another very preferred embodiment, said amino acid sequence (I) is SEQ ID NO: 49.

In another very preferred embodiment, said amino acid sequence (I) is SEQ ID NO: 50.

In another very preferred embodiment, said amino acid sequence (I) is SEQ ID NO: 51.

In another very preferred embodiment, said amino acid sequence (I) is SEQ ID NO: 52.

In another very preferred embodiment, said amino acid sequence (I) is SEQ ID NO: 53.

In another very preferred embodiment, said amino acid sequence (I) is SEQ ID NO: 54.

In another very preferred embodiment, said amino acid sequence (I) is SEQ ID NO: 55.

In another very preferred embodiment, said amino acid sequence (I) is SEQ ID NO: 56.

In another very preferred embodiment, said amino acid sequence (I) is SEQ ID NO: 57.

In another preferred embodiment, said cyclic peptide further comprises a linker, wherein said linker is attached to said amino acid sequence (I), wherein said linker comprises (i) at least one attachment moiety, (ii) at least one spacer moiety, (iii) at least one linking moiety, or (iv) any combination of (i), (ii) and (iii).

In another preferred embodiment, said at least one attachment moiety comprises or preferably consists of —O—$NH_2$, —O—NH— (an aminooxy moiety), —C(O)—$CH_2$—O—$NH_2$, —C(O)—$CH_2$—O—NH— (aminooxy acetyl moiety), —N—$NH_2$, —N—NH— (hydrazine moiety), -E(O)—NH—$NH_2$, or -E(O)—NH—NH— (hydrazide moiety), wherein E is C, S(O) or P. In a further preferred embodiment, said attachment moiety comprises or preferably consists of an —O—$NH_2$, —O—NH— (an aminooxy moiety), —C(O)—$CH_2$—O—$NH_2$, —C(O)—$CH_2$—O—NH— (aminooxy acetyl moiety), —N—$NH_2$, —N—NH— (hydrazine moiety), or (—C(O)—NH—$NH_2$, —C(O)—NH—NH— (carbohydrazide moiety). In another further preferred embodiment, said attachment moiety comprises or preferably consists of —O—$NH_2$ or —O—NH— (an aminooxy moiety).

In another preferred embodiment, said at least one spacer moiety comprises or preferably consists of $NH_2$—$CH_2$—$CH_2$—(O—$CH_2$—$CH_2$)$_n$—C(O)— or —NH—$CH_2$—$CH_2$—(O—$CH_2$—$CH_2$)$_n$—C(O)—, wherein n is an integer of 1 to 45, preferably 2 to 20, more preferably 6 to 8; or $NH_2$—$(CH_2)_m$—C(O)— or —NH—$(CH_2)_m$—C(O)—, wherein m is an integer of 2 to 45, preferably 2 to 20, more preferably 2 to 6.

In a preferred embodiment, said linker is attached to an amino group included in said amino acid sequence (I), wherein preferably said linker is attached to a free amino group of (i) the N-terminus of said amino acid sequence (I), or (ii) a side chain of an amino acid of said amino acid sequence (I). Preferably, the linker is attached to said amino group included in said amino acid sequence (I) by an amide bond. Said side chain is preferably of the amino acid lysine. In a preferred embodiment, X24 is lysine and said linker is attached to the free amino group of the side chain of X24.

In a very preferred embodiment, said linker is selected from the following formulas:

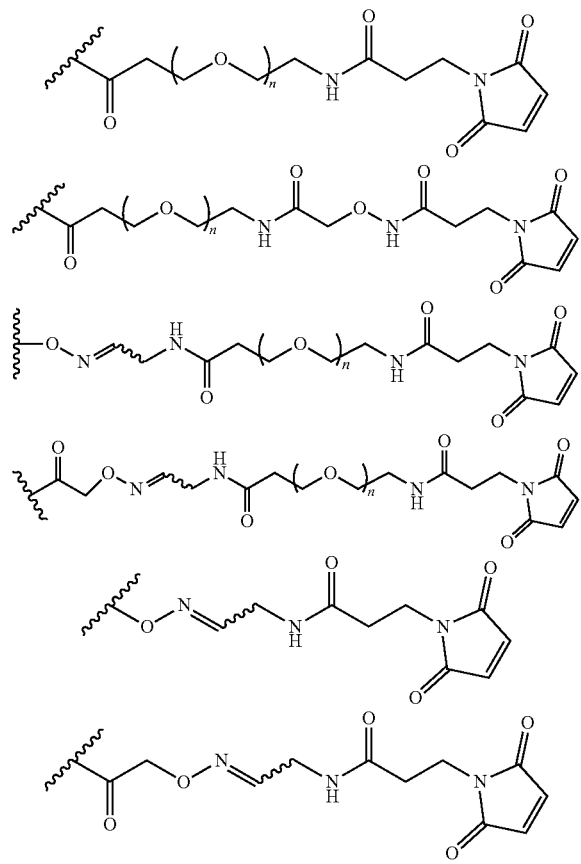

wherein n is an integer of 1 to 45, preferably 6 to 8, and the wavy line indicates the attachment site to said amino acid sequence (I).

In a further very preferred embodiment, said linker is selected from the following formulas:

wherein the wavy line indicates the attachment site to said amino acid sequence (I).

In a further very preferred embodiment, said cyclic peptide comprises, preferably is, a formula selected from any one of following formulas:

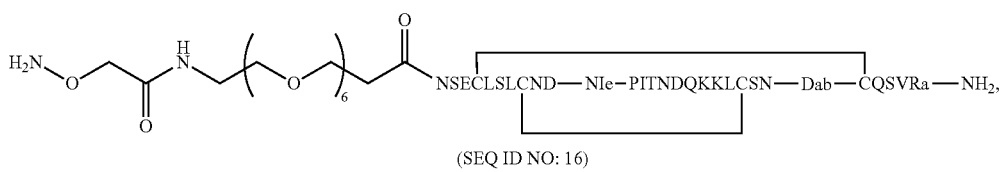

(SEQ ID NO: 16)

(3)

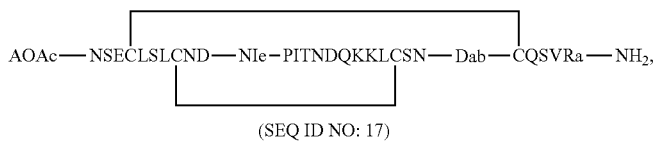

(SEQ ID NO: 17)

(4)

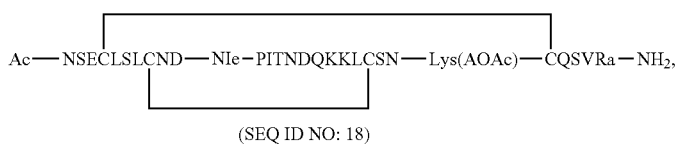

(SEQ ID NO: 18)

(5)

(6)

AOAc—RLSECLSLCND—Nle—PITNDQKKLCSNNCLKSa—NH₂, or (SEQ ID NO: 19)

(7)

AOAc—PVSTYMLTNSECLSLCNDMPITNDQKKLCSNNCQIVRQQa—NH₂.

(SEQ ID NO: 20)

In a further very preferred embodiment, said cyclic peptide comprises, preferably is, formula (3) (SEQ ID NO: 16). In a further very preferred embodiment, said cyclic peptide comprises, preferably is, formula (4) (SEQ ID NO: 17). In a further very preferred embodiment, said cyclic peptide comprises, preferably is, formula (5) (SEQ ID NO: 18). In a further very preferred embodiment, said cyclic peptide comprises, preferably is, formula (6) (SEQ ID NO: 19). In a further very preferred embodiment, said cyclic peptide comprises, preferably is, formula (7) (SEQ ID NO: 20).

In a further very preferred embodiment, said cyclic peptide comprises, preferably is, a formula selected from any one of formulas (3) (SEQ ID NO: 16), formula (4) (SEQ ID NO: 17), formula (5) (SEQ ID NO: 18), formula (6) (SEQ ID NO: 19), formula (7) (SEQ ID NO: 20), formula (19), formula (20), formula (21), formula (22), formula (23), formula (24), formula (25), formula (26), formula (27), formula (28), formula (29), formula (30), formula (31), formula (32), formula (33), formula (34), formula (35), formula (36) or formula (37).

In a further very preferred embodiment, said cyclic peptide comprises, preferably is, formula (19). In a further very preferred embodiment, said cyclic peptide comprises, preferably is, formula (20). In a further very preferred embodiment, said cyclic peptide comprises, preferably is, formula (21). In a further very preferred embodiment, said cyclic peptide comprises, preferably is, formula (22). In a further very preferred embodiment, said cyclic peptide comprises, preferably is, formula (23). In a further very preferred embodiment, said cyclic peptide comprises, preferably is, formula (24). In a further very preferred embodiment, said cyclic peptide comprises, preferably is, formula (25). In a further very preferred embodiment, said cyclic peptide comprises, preferably is, formula (26). In a further very preferred embodiment, said cyclic peptide comprises, preferably is, formula (27). In a further very preferred embodiment, said cyclic peptide comprises, preferably is, formula (28). In a further very preferred embodiment, said cyclic peptide comprises, preferably is, formula (29). In a further very preferred embodiment, said cyclic peptide comprises, preferably is, formula (30). In a further very preferred embodiment, said cyclic peptide comprises, preferably is, formula (31). In a further very preferred embodiment, said cyclic peptide comprises, preferably is, formula (32). In a further very preferred embodiment, said cyclic peptide comprises, preferably is, formula (33). In a further very preferred embodiment, said cyclic peptide comprises, preferably is, formula (34). In a further very preferred embodiment, said cyclic peptide comprises, preferably is, formula (35). In a further very preferred embodiment, said cyclic peptide comprises, preferably is, formula (36). In a further very preferred embodiment, said cyclic peptide comprises, preferably is, formula (37).

In a preferred embodiment, said peptide moiety of said conjugate has a length of 12 to 200 amino acids, more preferably of 21 to 120 amino acids, again more preferably of 21 to 80 amino acids. Preferred peptide moieties are non-human sequences to avoid the risk of autoimmune disorders when applied in the vaccination of humans.

In one embodiment, said peptide moiety of said conjugate comprises an amino acid sequence which includes one or more T-helper cell epitopes, and/or strings of polar residues that promote the solubility of the lipopeptide building block in water. Suitable T-helper cell epitopes can be found, e.g., in Weber et al. (T cell epitope: Friend or Foe? Immunogenicity of biologics in context, Advanced Drug Delivery Reviews, 2009, vol. 61, no. 11, 965-976), Caro-Aguilar (*Plasmodium vivax* Promiscuous T-Helper Epitopes Defined and Evaluated as Linear Peptide Chimera Immunogens, Infect. Immun., 2002, vol. 70, no. 7, 3479-3492), Mishra et al. (Human T-helper cell responses to a synthetic peptide derived from the hepatitis B surface antigen, Immunology, 1993, vol. 79, no. 3, 362-367), Kobayashi et al. (Defining Promiscuous MHC Class II Helper T-Cell Epitopes for the HER2/neu Tumor Antigen, Cancer Research, 2000, vol. 60, no. 18, 5228-523), Fraser et al. (Generation of a universal CD4 memory T cell recall peptide effective in humans, mice and non-human primates, Vaccine, 2014, vol. 32, no. 24, 2896-2903), Grabowska et al. (Identification of promiscuous HPV16-derived T helper cell epitopes for therapeutic HPV vaccine design, Int. J. Cancer, 2015, vol. 136, no. 1, 212-224) and WO1998/023635 A1. More preferred T-helper cell epitopes included in the peptide moiety are those listed in WO 2015/082501 such TT830-843, TT1064-1079, TT1084-1099, TT947-968, TT1174-1189, DTD271-290, DTD321-340, DTD331-350, DTD351-370, DTD411-430, DTD431-450, TT632-651, CTMOMP36-60, TraT1, TraT2, TraT3, HbcAg50-69, HbSAg19-33, HA307-319, MA17-31, MVF258-277, MVF288-302, CS.T3, SM Th, PADRE1 and PADRE2 as well as variants thereof in which one, two, or three amino acids are inserted, replaced by other amino acids or deleted.

In a further very preferred embodiment, the T-helper cell epitope comprises or preferably consists of the following amino acid sequence: IEKKIAKMEKASSVFNVVNS (SEQ ID NO: 6).

In a further embodiment, said peptide moiety comprises (i) an N-terminal amino acid sequence, wherein said N-terminal amino acid sequence comprises or preferably consists of fibroblast-stimulating lipopeptide FSL-1 (S-(2,3-bispalmitoyloxypropyl)- or PAM2-Cys-Gly-Asp-Pro-Lys-His-Pro-Lys-Ser-Phe; SEQ ID NO: 7), FSL-2 (S-(2,3-bispalmitoyloxypropyl)- or PAM2-Cys-Gly-Asp-Pro-Lys-His-Pro-Lys-Ser-Arg; SEQ ID NO: 8), FSL-3 (S-(2,3-bisstearyloxypropyl)-Cys-Gly-Asp-Pro-Lys-His-Pro-Lys- Ser-Phe; SEQ ID NO: 9), *Mycoplasma fermentans*-derived peptide MALP-2 (S-(2,3-bispalmitoyloxypropyl)- or PAM2-Cys-Gly-Asn-Asn-Asp-Glu-Ser-Asn-Ile-Ser-Phe-Lys-Glu-Lys; SEQ ID NO: 10) or GG; and/or (ii) a C-terminal amino acid sequence, wherein said C-terminal amino acid sequence comprises or preferably consists of a sequence recognized by an enzyme as cleavage site; wherein preferably said C-terminal amino acid sequence comprises or preferably consists of sequence KKKCa (SEQ ID NO: 11).

Said peptide moiety comprises at least one coiled coil peptide chain segment. As used herein, the term "coiled coil peptide chain segment" is a sequence of a peptide chain capable of forming a coiled coil (super coil) with at least one other coiled coil peptide chain segment. A coiled coil is a peptide structure in which at least two coiled coil peptide chain segments, each having preferably an alpha helical secondary structure, are associated into a bundle.

In one embodiment, said peptide moiety comprises more than one coiled coil peptide chain segment, wherein preferably said coiled coil peptide chain segments form a bundle. Preferably said bundle is monomeric, i.e. said coiled coil peptide chain segments are included in one peptide chain.

Coiled coil peptide chain segments of the invention contain multiple repeat units, preferably consecutively linked to each other. The repeat units of the coiled coil peptide chain segment may be identical or may be different, e.g. may contain at least one discontinuity, such as an insertion, deletion or exchange of at least one, preferably exactly 1, 2, 3 or 4 amino acids within the repeat unit.

In a preferred embodiment, said coiled coil peptide chain segment of said peptide moiety consists of 2 to 10 repeat units including 2, 3, 4, 5, 6, 7, 8, 9 and 10 repeat units, preferably 3 to 8 repeat units including 3, 4, 5, 6, 7, 8 repeat units, more preferably four repeat units. The upper number of repeat units in the peptide moiety influences the stability of the coiled coil. It is limited mainly by the feasibility of chemical synthesis of long peptides, but sequences containing more than three heptad repeats (e.g. four, five, six, seven, eight or ten repeat units) are preferred.

Coiled coil peptide chain segments according to the invention can be based on canonical repeat units and non-canonical repeat units. Preferred are canonical tandem heptad repeats that may form right-handed amphipathic alpha-helices, which then assemble to form helical bundles with left-handed coiled coils. Also included are peptides built from non-canonical, non-heptad-based repeats that form coiled coils that are not necessarily left-handed or even regular supercoils.

Repeat units of coiled coil peptide chain segments have a sequence with a certain number of amino acids, wherein the positions of the amino acids are traditionally labelled as lowercase letters. Design rules are discussed in more detail, for example, in Woolfson, D. N., Adv. Prot. Chem. 2005, 70, 79-112.

In a certain embodiment of the invention, said repeat unit of the coiled coil peptide chain segments consists of 7 to 15 amino acids, preferably 7 to 11 amino acids. More preferably said repeat unit is a heptad motif consisting of 7 amino acids, wherein the seven amino acid positions are designated with letters a, b, c, d, e, f and g. In a preferred embodiment, said heptad motif consist of a sequence selected from IEKKIEA (SEQ ID NO: 12) or IEKKIES (SEQ ID NO: 13).

In a preferred embodiment, said heptad motif includes amino acids having hydrophobic residues at positions a and d, and preferably polar, helix-favoring residues at the other residues.

In a further preferred embodiment, said heptad motifs has seven amino acid positions designated with letters a b c d e f g, and wherein positions a and d in each heptad motif comprise independently of each other:
an alpha-amino acid with a hydrophobic side chain and/or an aromatic or hetero-aromatic side chain,
in zero, one or two of all the a and d positions an amino acid with a polar non-charged residue, and
in zero or one of all the a and d positions (i) an amino acid with a polar cationic residue or an acetylated derivative thereof, or (ii) an amino acid with a polar anionic residue, or (iii) glycine.

Preferred are coiled coil peptide chain segments containing between 3-8 tandemly linked heptad motifs, wherein positions a and d in each heptad motif (abcdefg) contain alpha-amino acids belonging to the Group 1 and/or to the Group 2 as defined herein below. In addition, not more than two of all the a and d positions may be occupied by any amino acid residue belonging to the Group 3, and not more than one of all the a and d positions may be occupied by any amino acid residue belonging to the Group 4 or Group 5 or by glycine. In addition, in positions b, c, e, f and g, alpha-amino acids belonging to the Groups 3, 4 and 5 are preferred, but amino acids belonging to the Groups 1 and 2 are allowed, with the addition that not more than one of these positions within any one heptad motif may be glycine, but none may be proline.

Group 1 comprises alpha-amino acid residues with small to medium sized hydrophobic side chains. A hydrophobic residue refers to an amino acid side chain that is uncharged at physiological pH and that is repelled by aqueous solution. These side chains generally do not contain hydrogen bond donor groups, such as primary and secondary amides, primary and secondary amines and the corresponding protonated salts thereof, thiols, alcohols, ureas or thioureas. However, they may contain hydrogen bond acceptor groups such as ethers, thioethers, esters, tertiary amides, or tertiary amines. Genetically encoded amino acids in this group include alanine, isoleucine, leucine, methionine and valine. Preferred hydrophobic residues are mentioned in WO 2008/068017, claim 6.

Group 2 comprises amino acid residues with aromatic or heteroaromatic side chains. An aromatic amino acid residue refers to a hydrophobic amino acid having a side chain containing at least one ring having a conjugated aromatic pi-electron system. In addition, it may contain additional hydrophobic groups such as lower alkyl, aryl or halogen, hydrogen bond donor groups such as primary and secondary amines, and the corresponding protonated salts thereof, primary and secondary amides, alcohols, and hydrogen bond acceptor groups such as ethers, thioethers, esters, tertiary amides or tertiary amines. Genetically encoded aromatic amino acids include phenylalanine and tyrosine. A heteroaromatic amino acid residue refers to a hydrophobic amino acid having a side chain containing at least one ring having a conjugated aromatic pi-system incorporating at least one heteroatom such as O, S and N. In addition such residues may contain hydrogen bond donor groups such as primary and secondary amides, primary and secondary amines and the corresponding protonated salts thereof, alcohols, and hydrogen bond acceptor groups such as ethers, thioethers, esters, tertiary amides or tertiary amines. Genetically encoded heteroaromatic amino acids include tryptophan and histidine. Preferred aromatic or heteroaromatic side chains are mentioned in WO 2008/068017, claim 6.

Group 3 comprises amino acids containing side chains with polar non-charged residues. A polar non-charged residue refers to a hydrophilic side chain that is uncharged at physiological pH, but that is not repelled by aqueous solutions. Such side chains typically contain hydrogen bond donor groups such as primary and secondary amides, primary and secondary amines, thiols, and alcohols. These groups can form hydrogen bond networks with water molecules. In addition, they may also contain hydrogen bond acceptor groups such as ethers, thioethers, esters, tertiary amides, or tertiary amines. Genetically encoded polar non-charged amino acids include asparagine, cysteine, glutamine, serine and threonine. Preferred polar non-charged residues are mentioned in WO 2008/068017, claim 6.

Group 4 comprises amino acids containing side chains with polar cationic residues and acylated derivatives thereof, such as acylamino-derived residues and urea-derived residues. Polar cationic side chains refer to a basic side chain, which is protonated at physiological pH. Genetically encoded polar cationic amino acids include arginine, lysine and histidine. Citrulline is an example for a urea-derived amino acid residue. Preferred polar cationic residue or acylated derivatives thereof are mentioned in WO 2008/068017, claim 6.

Group 5 comprises amino acids containing side chains with polar anionic residues. Polar anionic refers to an acidic side chain, which is deprotonated at physiological pH. Genetically encoded polar anionic amino acids include aspartic acid and glutamic acid. A particular polar cationic residue is —(CH2)aCOOH, wherein "a" is 1 to 4. Preferred polar anionic residues are mentioned in WO 2008/068017, claim 6.

More preferred are coiled coil peptide chain segments containing between 3 to 8 tandemly linked heptad motifs, wherein each heptad motif (abcdefg) may have any one of the following sequences:

1xx1xxx (referring respectively to the positions abcdefg);
1xx2xxx (referring respectively to the positions abcdefg);
2xx1xxx (referring respectively to the positions abcdefg); or
2xx2xxx (referring respectively to the positions abcdefg);

wherein 1 is a genetically encoded amino acid from Group 1; 2 is a genetically encoded amino acid from Group 2; and wherein x is a genetically encoded amino acid from Groups 1, 2, 3, 4 or 5 or glycine.

Preferably, said alpha-amino acid with a hydrophobic side chain is alanine, isoleucine, leucine, methionine and valine; alpha-amino acids with aromatic or hetero-aromatic residue are phenylalanine, tyrosine, tryptophan and histidine; alpha-amino acids with polar non-charged residue are asparagine, cysteine, glutamine, serine and threonine; alpha-amino acids with polar cationic residue are arginine, lysine and histidine; and alpha-amino acids with polar anionic residue are aspartic acid and glutamic acid.

Equally preferred are coiled coil peptide sequences identified in naturally occurring peptides and proteins, but excluding those of human origin. These are, for example, coiled coils identified in viral and bacterial proteins, such as mentioned in WO 2008/068017.

In a very preferred embodiment, said coiled coil peptide chain segment of said peptide moiety comprises or preferably consists of 2 to 10 repeat units.

In a further very preferred embodiment, said coiled coil peptide chain segment of said peptide moiety comprises or preferably consists of 3 to 8 repeat units.

In a very preferred embodiment, said coiled coil peptide chain segment of said peptide moiety comprises or preferably consists of 4 repeat units.

In a very preferred embodiment, said coiled coil peptide chain segment of said peptide moiety comprises or preferably consists of 2 to 10 repeat units, wherein said repeat units consist of 15, 11 or 7 amino acids, preferably 7 amino acids (heptad motif), In a further very preferred embodiment, said coiled coil peptide chain segment of said peptide moiety comprises or preferably consists of 3 to 8 repeat units, wherein said repeat units consist of 15, 11 or 7 amino acids, preferably 7 amino acids (heptad motif), In a very preferred embodiment, said coiled coil peptide chain segment of said peptide moiety comprises or preferably consists of 4 repeat units, wherein said repeat units consist of 15, 11 or 7 amino acids, preferably 7 amino acids (heptad motif), In a very preferred embodiment, said coiled coil peptide chain segment of said peptide moiety comprises or preferably consists of 2 to 10 repeat units, wherein said repeat units consist of 15, 11 or 7 amino acids, preferably 7 amino acids (heptad motif), wherein said repeat units comprise or consist independently of each other of a sequence selected from IEKKIEA (SEQ ID NO: 12) or IEKKIES (SEQ ID NO: 13).

In a further very preferred embodiment, said coiled coil peptide chain segment of said peptide moiety comprises or preferably consists of 3 to 8 repeat units, wherein said repeat units consist of 15, 11 or 7 amino acids, preferably 7 amino acids (heptad motif), wherein said repeat units comprise or consist independently of each other of a sequence selected from IEKKIEA (SEQ ID NO: 12) or IEKKIES (SEQ ID NO: 13).

In a very preferred embodiment, said coiled coil peptide chain segment of said peptide moiety comprises or preferably consists of 4 repeat units, wherein said repeat units consist of 15, 11 or 7 amino acids, preferably 7 amino acids (heptad motif), wherein said repeat units comprise or consist independently of each other of a sequence selected from IEKKIEA (SEQ ID NO: 12) or IEKKIES (SEQ ID NO: 13).

In a very preferred embodiment, said coiled coil peptide chain segment of said peptide moiety comprises or preferably consists of 2 to 10 repeat units, wherein said repeat units consist of 15, 11 or 7 amino acids, preferably 7 amino acids (heptad motif), wherein said repeat units comprise or consist of a sequence IEKKIEA (SEQ ID NO: 12)

In a further very preferred embodiment, said coiled coil peptide chain segment of said peptide moiety comprises or preferably consists of 3 to 8 repeat units, wherein said repeat units consist of 15, 11 or 7 amino acids, preferably 7 amino acids (heptad motif), wherein said repeat units comprise or consist of a sequence IEKKIEA (SEQ ID NO: 12)

In a very preferred embodiment, said coiled coil peptide chain segment of said peptide moiety comprises or preferably consists of 4 repeat units, wherein said repeat units consist of 15, 11 or 7 amino acids, preferably 7 amino acids (heptad motif), wherein said repeat units comprise or consist of a sequence IEKKIEA (SEQ ID NO: 12)

In a very preferred embodiment, said coiled coil peptide chain segment of said peptide moiety comprises or preferably consists of 2 to 10 repeat units, wherein said repeat units consist of 15, 11 or 7 amino acids, preferably 7 amino acids (heptad motif), wherein said repeat units comprise or consist of a sequence IEKKIES (SEQ ID NO: 13).

In a further very preferred embodiment, said coiled coil peptide chain segment of said peptide moiety comprises or preferably consists of 3 to 8 repeat units, wherein said repeat units consist of 15, 11 or 7 amino acids, preferably 7 amino acids (heptad motif), wherein said repeat units comprise or consist of a sequence IEKKIES (SEQ ID NO: 13).

In a very preferred embodiment, said coiled coil peptide chain segment of said peptide moiety comprises or preferably consists of 4 repeat units, wherein said repeat units consist of 15, 11 or 7 amino acids, preferably 7 amino acids (heptad motif), wherein said repeat units comprise or consist of a sequence IEKKIES (SEQ ID NO: 13).

The lipid moiety comprises two or three, preferably two, hydrocarbyl chains. Preferred lipid moieties are lipids containing two or three, preferably two extended hydrocarbyl chains.

In a one embodiment, said lipid moiety is a phospholipid. Preferably, said phospholipid possess either ester- or ether-linked extended alkyl or alkenyl chains, such as either enantiomers of 1,2-dipalmitoyl-sn-glycero-3-phosphoethanolamine, or achiral analogues such as 1,3-dipalmitoyl-glycero-2-phosphoethanolamine.

Preferably, said lipid moiety is one of formulas LM 1 to LM 8:

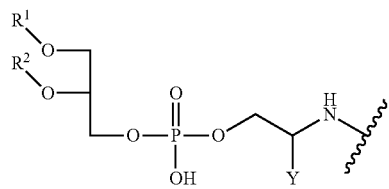

LM1

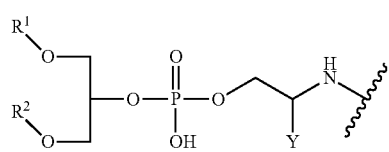

LM2 wherein $R^1$ and $R^2$ in formulas LM 1 and LM 2 are independently of each other hydrocarbyl or hydrocarbyl-C=O, and Y is H or COOH;

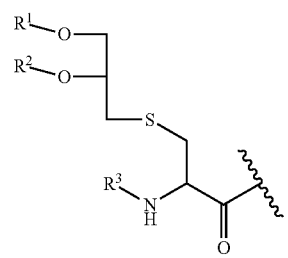

LM 3 wherein $R^1$, $R^2$ and $R^3$ in formula LM 3 are independently of each other hydrocarbyl or hydrocarbyl-C=O; or $R^1$ and $R^2$ are independently of each other hydrocarbyl or hydrocarbyl-C=O, and $R^3$ is H or acetyl or lower alkyl-C=O;

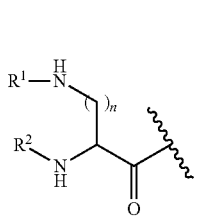

LM 4

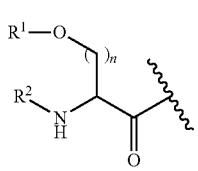

LM 5 wherein $R^1$ and $R^2$ in formulas LM 4 and LM 5 are independently of each other hydrocarbyl or hydrocarbyl-C=O, and n is 1, 2, 3 or 4;

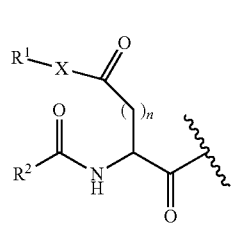

LM 6 wherein $R^1$ and $R^2$ in formula LM 6 are independently of each other a hydrocarbyl, X is O or NH, and n is 1, 2, 3 or 4, or

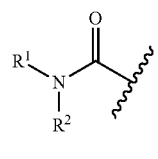

LM 7

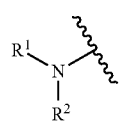

LM 8 wherein $R^1$ and $R^2$ in formulas LM 7 and LM 8 are independently of each other hydrocarbyl. A preferred lipid moiety is di-palmitoyl-S-glycerylcysteinyl of formula LM3, wherein $R^1$ and $R^2$ are palmitoyl, and $R^3$ is H or acetyl.

In a preferred embodiment, said hydrocarbyl or hydrocarbyl chain is a straight or branched alkyl or alkenyl chain consisting of at least 7 carbon atoms, preferably between 8 and 50 carbon atoms, more preferably between 8 and 25 carbon atoms, and optionally one, two or three double bonds. Alkenyl has preferably one, two or three double bonds in the chain, each with E or Z geometry, as is customarily found in natural fatty acids and fatty alcohols. Also included in the definition of "hydrocarbyl" or "hydrocarbyl chain" is branched alkyl or alkenyl, for example alkyl bearing a methyl or ethyl substituent at the second or third carbon atom counted from the end of the chain, as e.g. as in 2-ethyl-hexyl.

Preferably, the term, "lower alkyl" means alkyl with 1 to 7 carbon atoms, more preferably 1 to 4 carbon atoms, such as methyl, ethyl, n-propyl, iso-propyl, n-butyl, sec-butyl, iso-butyl or tert-butyl.

In one embodiment, the lipid moiety is linked to the peptide moiety, and the cyclic peptide is linked to the peptide moiety of the lipopeptide building block. In an alternative embodiment, the lipid moiety is linked to the cyclic peptide, wherein the cyclic peptide in turn is linked to the peptide moiety. However, the first option is preferred.

In one embodiment, the lipid moiety is linked to the cyclic peptide or preferably the peptide moiety, either directly or via a coupling moiety. Preferably, the lipid moiety is linked to the cyclic peptide or preferably the peptide moiety at or near one terminus, i.e. the N-terminus or the C-terminus, preferably the N-terminus. In a preferred embodiment, the lipid moiety is linked to the first, second, third, fourth or fifth amino acid of the cyclic peptide or preferably the peptide moiety, calculated from the N-terminus or C-terminus of the peptide moiety. The lipid moiety may be linked, directly or through a coupling moiety, to the backbone or to the side chain of one of the amino acids of the cyclic peptide or preferably the peptide moiety, preferably said amino acid is near to the terminus, more preferably it is the first, second, third, fourth or fifth amino acid of the cyclic peptide or preferably the peptide moiety.

The lipid moiety may be attached to the peptide moiety or cyclic peptide (1) directly, or (2) via a coupling moiety. If the peptide moiety and the lipid moiety are directly linked, this is preferably accomplished through an amide bond between a lipid moiety carbonyl function and an amino function, e.g. the N-terminal amino function, of the peptide moiety. However, particular lipid moieties LM 1, LM 2 and LM 8 are preferably connected through an amide bond between their amine function and a carboxyl function, e.g. the C terminal carboxyl function, of the peptide moiety. It will be apparent to those knowledgeable in this area, that a large variety of suitable coupling moieties and coupling strategies exist, which include but are not limited to linkers based on dicarboxylic acid derivatives, linkers containing one or multiple ethylene glycol units, amino acid residues (including alpha-, beta-, gamma-, omega-amino acids), or sugar (carbohydrate) units, or containing heterocyclic rings. Particular coupling moieties considered are coupling moieties CM 1 to CM 19, wherein n is between 1 and 45 and m is between 1 and 45, for example wherein n is between 1 and 20 and m is between 1 and 20, shown with the connecting functional group C=O and/or X, wherein X is O or NH.

In a preferred embodiment, said coupling moiety comprises or preferably consists of one of formulas CM 1 to CM 19:

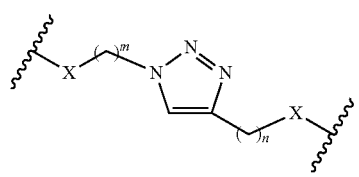
CM1

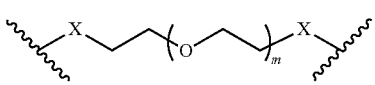
CM2

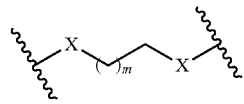
CM3

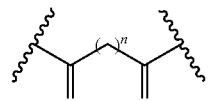
CM4

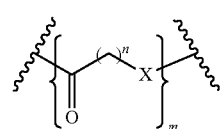
CM5

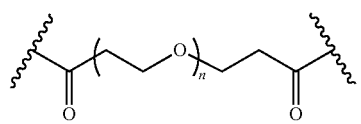
CM6

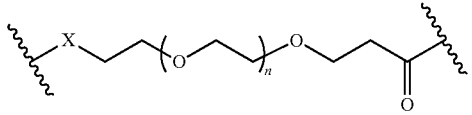
CM7

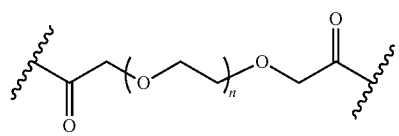
CM8

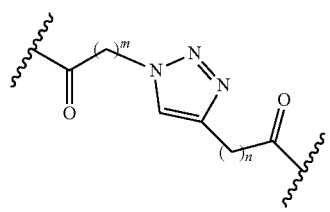
CM9

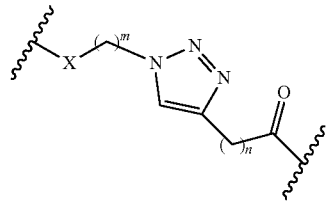
CM10

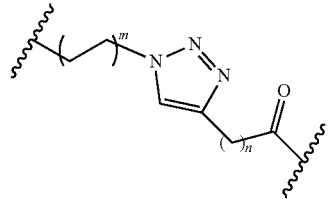
CM11

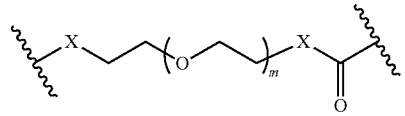
CM12

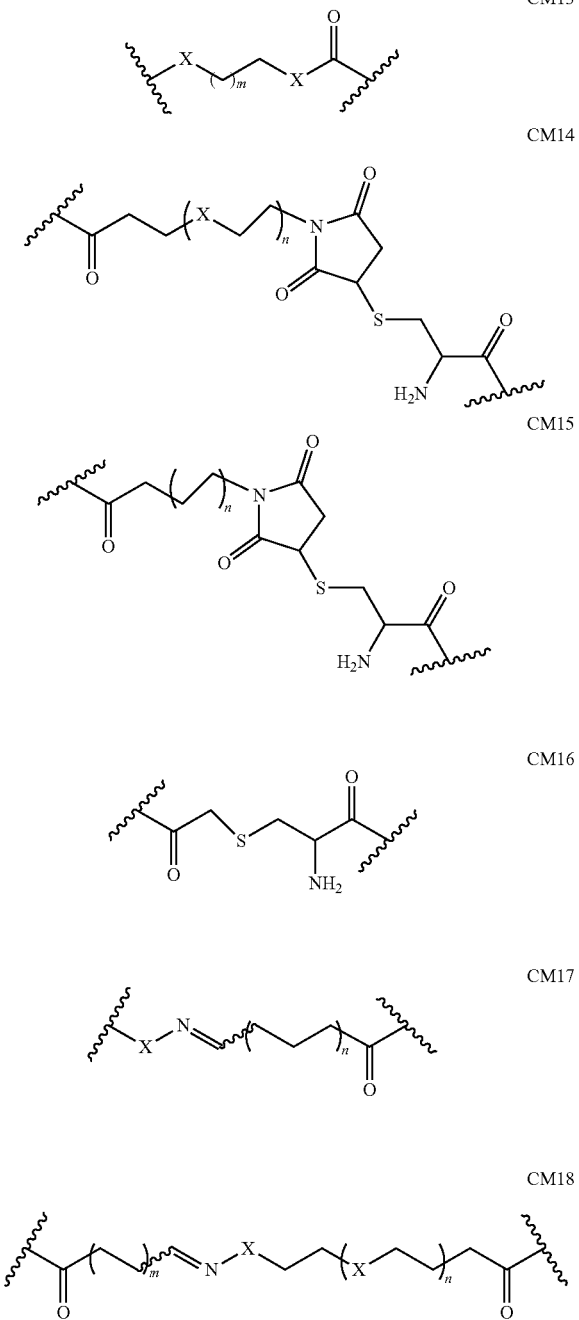

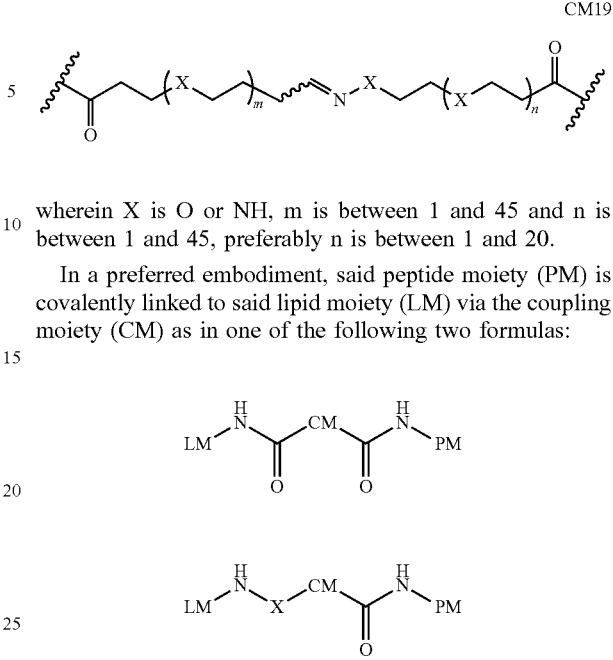

wherein X is O or NH, m is between 1 and 45 and n is between 1 and 45, preferably n is between 1 and 20.

In a preferred embodiment, said peptide moiety (PM) is covalently linked to said lipid moiety (LM) via the coupling moiety (CM) as in one of the following two formulas:

wherein X is O or NH, and wherein preferably the coupling moiety (CM) is one of formulas CM 1 to CM 19.

A carbonyl function shown for CM 1 to CM 19 may be connected to an amino function of a suitable lipid moiety and/or an amino function, e.g. the N-terminal amino function, of the peptide chain through an amide bond. Alternatively, a carbonyl function shown for CM 1 to CM 19 may be connected to a lipid moiety by replacement of the corresponding carbonyl function in particular lipid moieties LM 3 to LM 7.

A functional group X shown for CM 1 to CM 19 (with the meaning NH or O) may be connected to a carbonyl function of a suitable lipid moiety (LM) and/or a carboxyl function, e.g. the C terminal carboxyl function, of the peptide chain (PC) through an amide bond (for X =NH) or through an ester bond (for X=O).

In one preferred embodiment, the terminal CH$_2$ group of CM 11 is connected to an amino function of a suitable lipid moiety, an amino function, e.g. the N terminal amino function, of the peptide chain, or a carbonyl function of a suitable lipid moiety.

In a very preferred embodiment, said lipopeptide building block is selected from any one of the formula GG(IEKKIEA)$_4$IEKKIAKMEKASSVFNVVNSKKKCa—NH$_2$ (SEQ ID NO: 63)

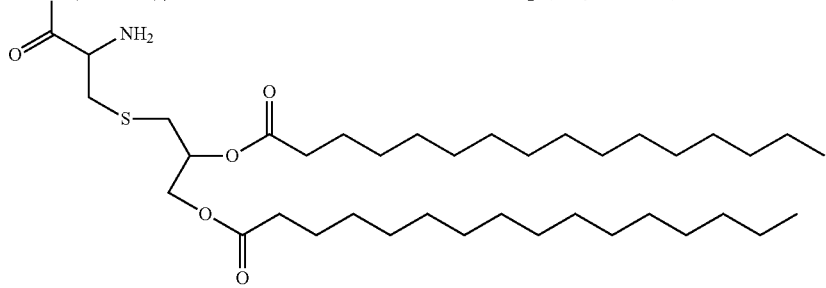

or

-continued
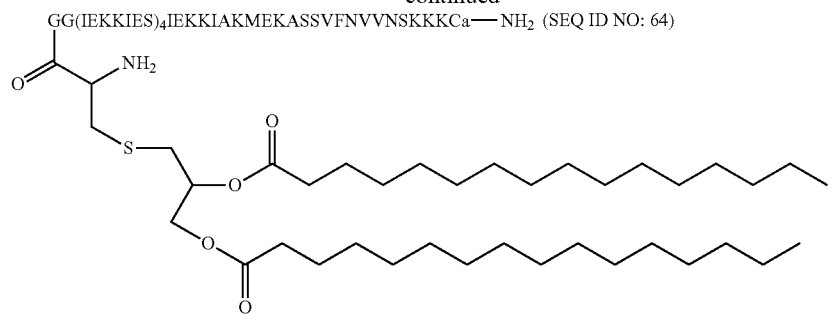
In a further very preferred embodiment, said lipopeptide building block is
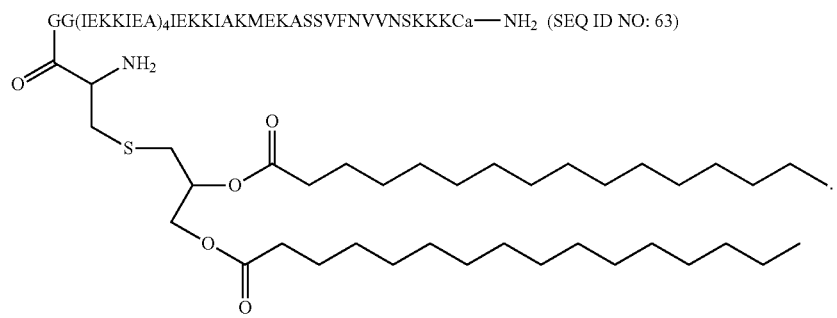
In another very preferred embodiment, said lipopeptide building block is
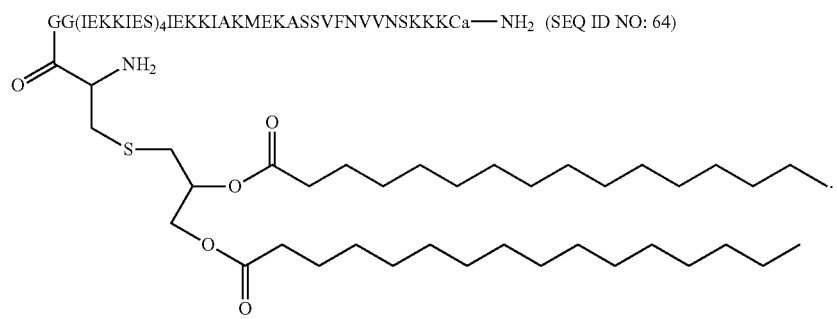

In a further very preferred embodiment, said conjugate is selected from any one of the formula
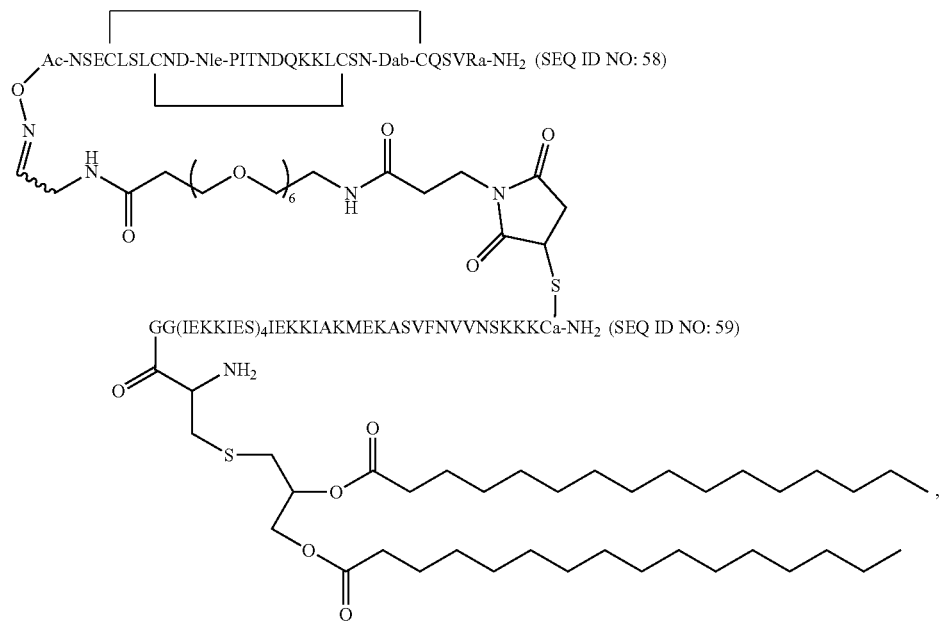
(12)
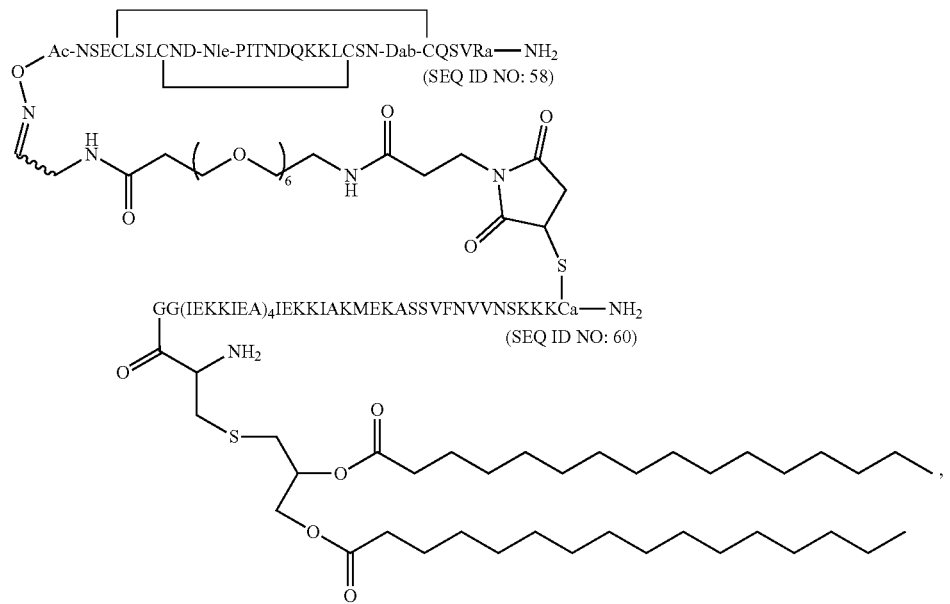
(13)

(14)
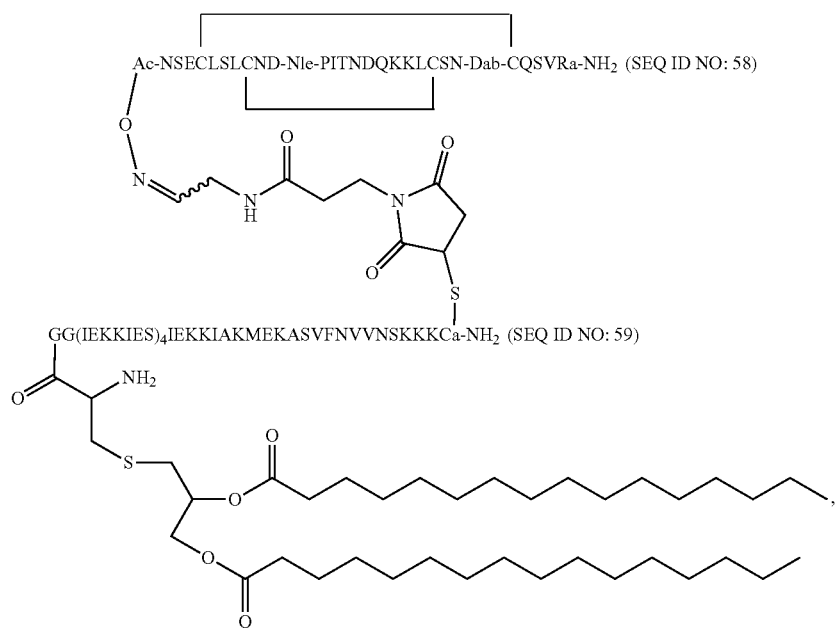
(15)
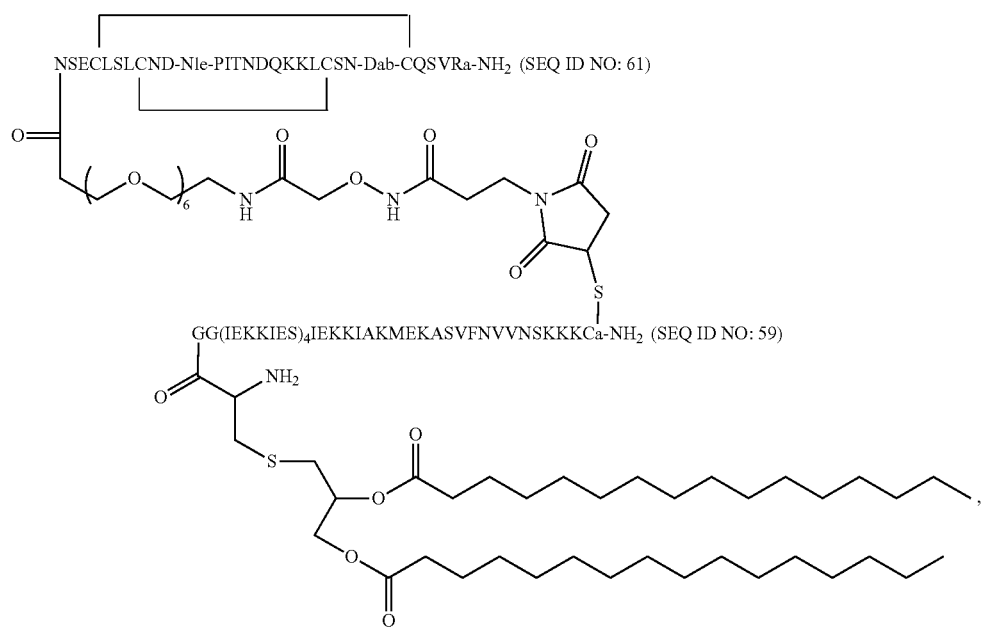

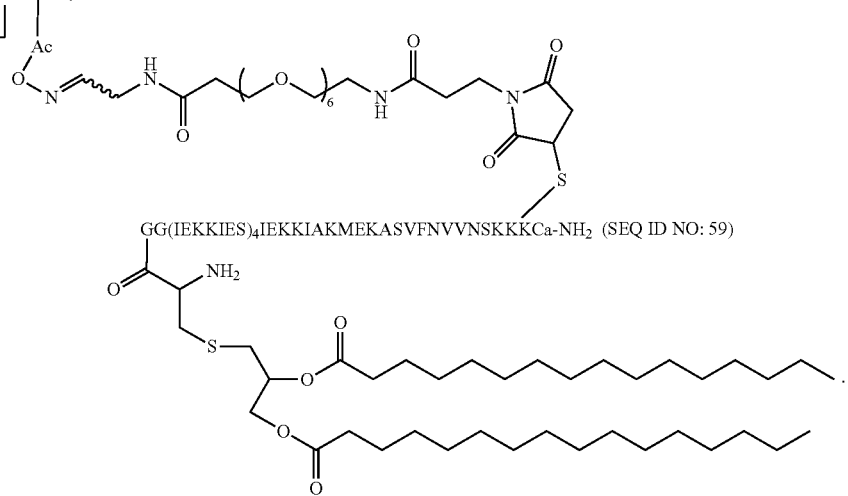
(16)
In a further very preferred embodiment, said conjugate is
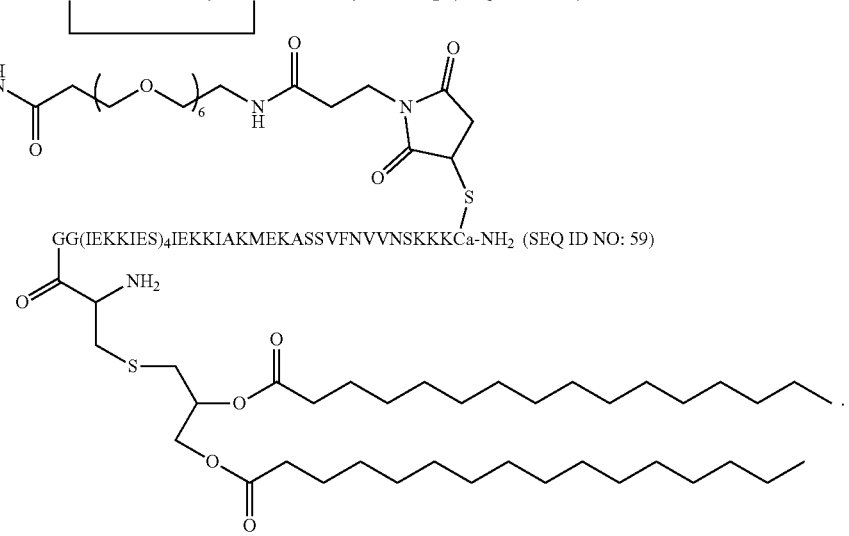
(12)

In a further very preferred embodiment, said conjugate is
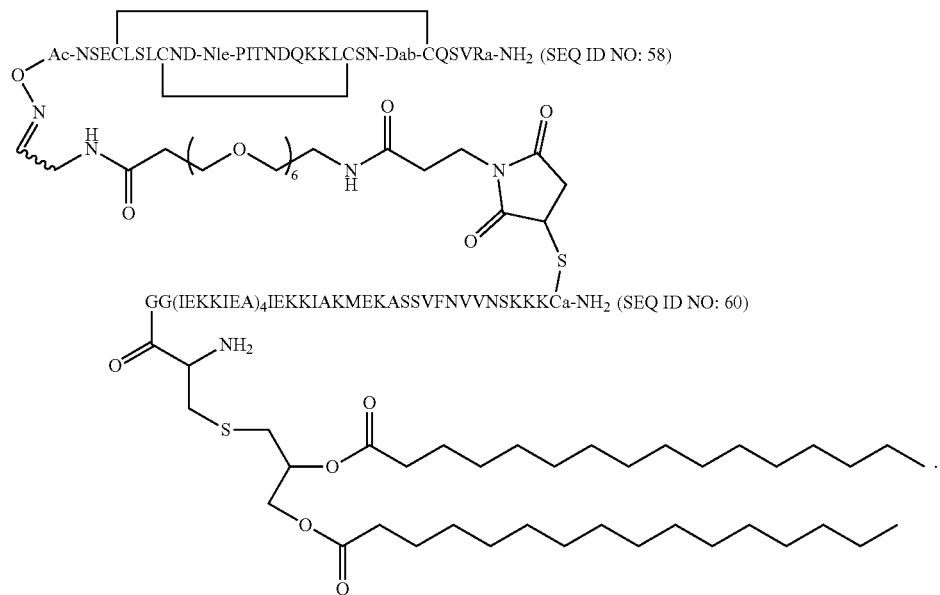
(13)
In a further very preferred embodiment, said conjugate is
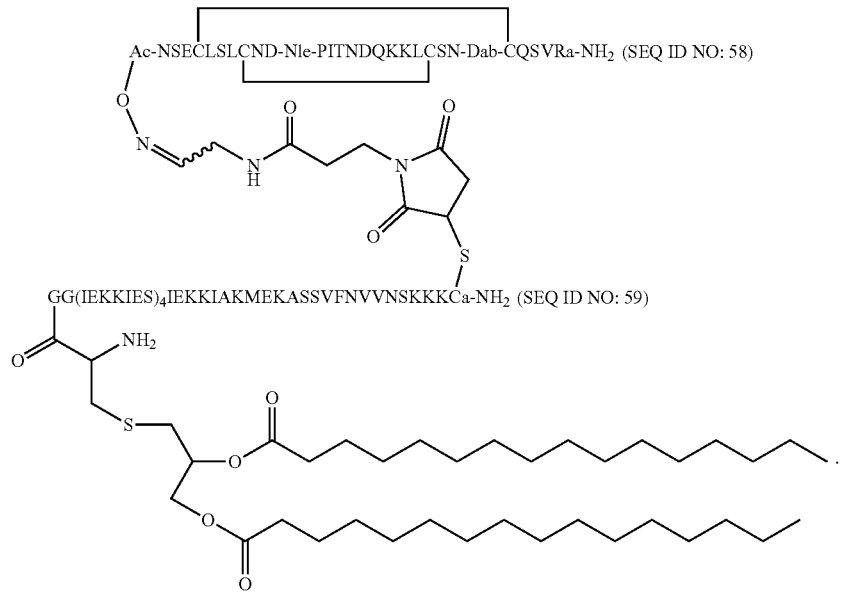
(14)

In a further very preferred embodiment, said conjugate is (15)

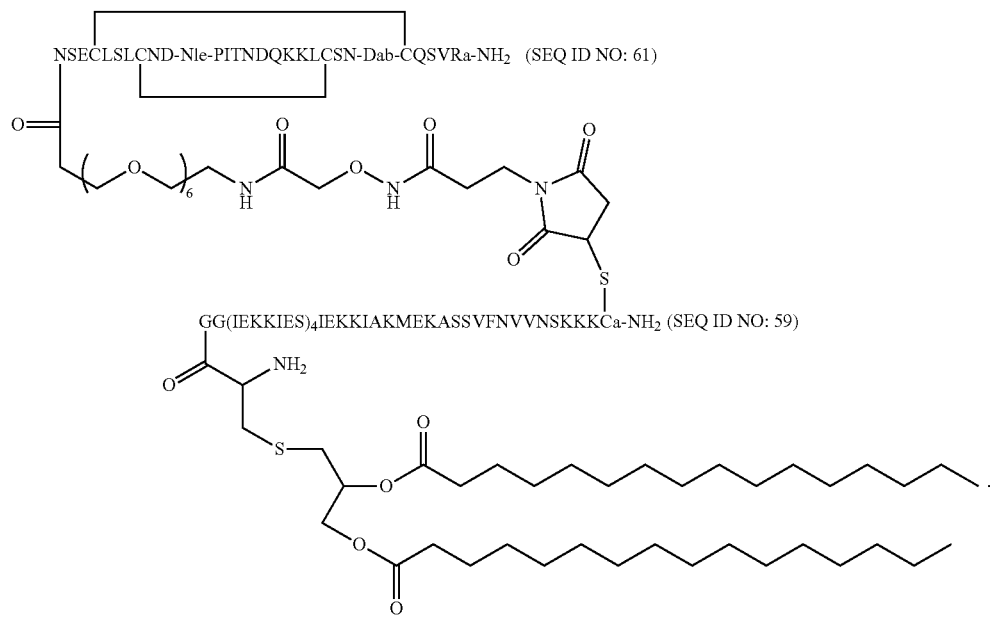

In a further very preferred embodiment, said conjugate is (16)

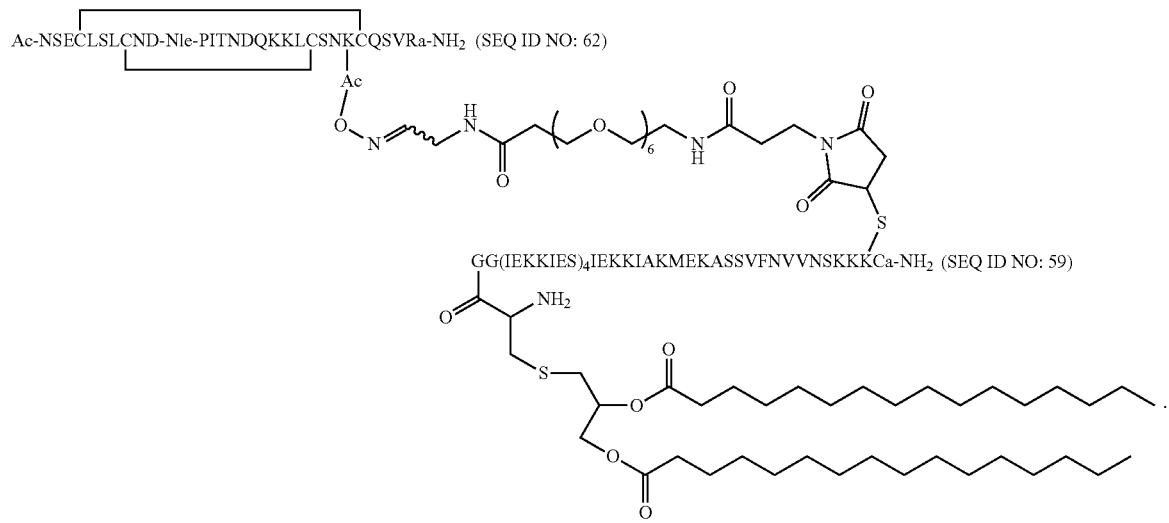

In another aspect, the present invention provides for a bundle of conjugates comprising 2, 3, 4, 5, 6 or 7 of the inventive conjugate.

In another aspect, the present invention provides for a bundle of conjugates comprising 2, 3, 4 or 5 of the inventive conjugate.

In another very preferred aspect, the present invention provides for a bundle of conjugates comprising 3 of the inventive conjugate.

In another aspect, the present invention provides for a bundle of conjugates comprising 2, 3, 4, 5, 6 or 7 of the inventive conjugate, wherein said conjugate is selected from any one of the formula (12), (13), (14), (15), or (16), wherein preferably said conjugate is selected from any one of the formula (12), (13) or (15), and wherein further preferably said conjugate is formula (12).

In another aspect, the present invention provides for a bundle of conjugates comprising 2, 3, 4 or 5 of the inventive conjugate, wherein said conjugate is selected from any one of the formula (12), (13), (14), (15), or (16), wherein preferably said conjugate is selected from any one of the formula (12), (13) or (15), and wherein further preferably said conjugate is formula (12).

In another very preferred aspect, the present invention provides for a bundle of conjugates comprising 3 of the inventive conjugate, wherein said conjugate is selected from any one of the formula (12), (13), (14), (15), or (16), wherein preferably said conjugate is selected from any one of the formula (12), (13) or (15), and wherein further preferably said conjugate is formula (12).

According to one embodiment, in said bundle, the coiled coil peptide chain segments of said peptide moieties comprised by said conjugates are coiled together, preferably said coiled coil peptide chain segments are helically coiled together, more preferably said coiled coil peptide chain segments are alpha-helically coiled together.

In a further preferred embodiment, in said bundle, the coiled coil peptide chain segments of said peptide moieties comprised by said conjugates are coiled together, In a further preferred embodiment, in said bundle, the coiled coil peptide chain segments of said peptide moieties comprised by said conjugates are coiled together, wherein said coiled coil peptide chain segments are helically coiled together.

In a further preferred embodiment, in said bundle, the coiled coil peptide chain segments of said peptide moieties comprised by said conjugates are coiled together, wherein said coiled coil peptide chain segments are alpha-helically coiled together.

In a preferred embodiment, said coiled coil peptide chain segments of said peptide moieties are coiled together left-handed or right-handed.

In a further preferred embodiment, said coiled coil peptide chain segments of said peptide moieties are coiled together left-handed.

In a further preferred embodiment, said coiled coil peptide chain segments of said peptide moieties are coiled together right-handed.

According a preferred embodiment, in said bundle, said coiled coil peptide chain segments of said peptide moieties form an alpha-helical left-handed coil.

In one embodiment, said coiled coil peptide chain segments have a parallel orientation, i.e. they run in the same direction; or they have an anti-parallel orientation, i.e. they run in directions opposite to each other; wherein the first option is preferred. The term "direction" is based on the direction of a peptide chain having on one side an N-terminus and on the other side a C-terminus.

In a preferred embodiment of said inventive bundle, said coiled coil peptide chain segments of said peptide moieties form a left-handed alpha-helical coiled coil, wherein the coiled coil peptide chain segments have a parallel orientation in said coiled coil.

Preferably, said bundle comprises 2 to 7 (e.g. dimer, trimer, tetramer, pentamer, hexamer or heptamer), more preferably 2, 3, 4 or 5, again more preferably 3 helically twisted coiled coil peptide chain segments, having a parallel orientation in said coiled coil.

In a preferred embodiment, said coiled coil peptide chain segments have the same sequence (homo-) or different sequences (hetero-).

In a further aspect, the present invention provides for a synthetic virus-like particle comprising the cyclic peptide of the present invention.

In another aspect, the present invention provides for a synthetic virus-like particle comprising at least one bundle of conjugates of the present invention.

In another aspect, the present invention provides for a synthetic virus-like particle comprising at least one bundle of conjugates of the present invention, wherein said conjugate is selected from any one of the formula (12), (13), (14), (15), or (16), wherein preferably said conjugate is selected from any one of the formula (12), (13) or (15), and wherein further preferably said conjugate is formula (12).

The invention also relates to a method of preparing the synthetic virus-like particles of the invention. Synthetic virus-like particles (SVLP) may be produced by a self-assembly process, e.g. in aqueous solution. This method may involve dissolving the lipopeptide building block in a suitable carrier, preferably an aqueous buffer system (e.g. buffered saline or unbuffered saline). The solvent may be removed after preparation of the synthetic virus-like particles, for example by lyophilization or spray drying.

Conjugates including the specific combination of the cyclic peptide of the invention and the lipopeptide building block of the invention self-assemble to bundles and further to synthetic virus-like particles (SVLPs). The self-assembly process includes (1) the oligomerization of the coiled-coil domains of peptide moiety of the lipopeptide building block, to form a bundle, preferably a helical bundle, more preferably a parallel helical bundle of a defined oligomerization state, preferably a trimeric bundle; and (2) the oligomerization of the bundles to an SVLP. When the lipid moiety is attached to the peptide moiety within the lipopeptide building block, the lipid moieties aggregate at one end of the bundle or SVLP. Furthermore, multiple copies of the cyclic peptide are then presented on the surface of the bundle or SVLP, i.e. the other, non-lipophilic end of the bundle or SVLP. The process is driven by the self-association of the lipid moiety attached to each lipopeptide building block, which then occupy the central lipid core of the SVLP. In this way, the peptide chains in each helical bundle are oriented outwards, towards the bulk solvent. The size and composition of the lipopeptide building block thus determines the final size and shape of the SVLP, the diameters of which is typically in the nanometer range (10-30 nm).

Therefore, SVLPs of the invention may be viewed as specific macromolecular carriers, or delivery vehicles for the cyclic peptide, for the purpose of raising efficient immune responses against the RSV in a subject, also without the use of potentially harmful adjuvants. The unique combination of properties of the cyclic peptide and the lipopeptide building block makes the SVLP of the invention ideal to elicit efficient immune responses against RSV in a subject, and hence for applications in RSV vaccination.

B cell responses are initiated by the interaction of specific B-cell receptors on target B-cells with antigen, and in particular, by clustering of multiple B-cell receptors on the surface of B-cells through the binding of multivalent antigens. Having multiple copies of the cyclic peptide on the surface of the SVLP of the invention thus is believed to enhance receptor affinity through an avidity effect and to create clusters of antigen-bound B-cell receptors on the cell surface. In the present invention, the ability of the coiled coil peptide chain segment to form helical bundles of defined oligomerization state is exploited to allow multivalent display of the attached cyclic peptide. To increase the immune response, T-cell epitopes may be incorporated into, or appended to, designed or natural coiled-coil sequences.

Another effect of the lipid moiety is to facilitate presentation of the epitope to B cells, since it is known that antigens associated with membranes are particularly effective at activating B-cells and promoting B cell-driven T cell activation. The high local concentration of lipid moieties within the assembled bundle of conjugates and SVLP is believed to facilitate interaction of the assembly with membranes and to promote presentation of antigens to B cells, and thus is able to elicit strong antibody-based immune responses. This leads to the further advantage that the use of toxic adjuvants during immunizations can be avoided.

It is a general feature of surfactant, detergent-like molecules possessing a polar head group and a non-polar, hydrophobic lipid tail, that they form thermodynamically stable aggregates such as micelles and vesicles in aqueous solution, with the extended hydrophobic regions clustered in the micelle core, sequestered away from contact with water, while the polar head groups interact with solvent. However, the bundle of conjugates and SVLPs of the present invention are not simply micelles. Their macromolecular architecture is maintained by a unique combination of non-covalent forces, namely, the forces driving assembly of the coiled-coil peptide domain into a helical bundle, coupled with the hydrophobic forces driving sequestration of the lipid tails in the interior of the particle. The concentrations at which micelles begin to form, corresponding to the maximum concentration at which free monomer exists in solution, is the critical micelle concentration, or more generally, the critical aggregation concentration. The critical micelle concentration provides a measure of the thermodynamic stability of micelles. The critical micelle concentration value depends on the structure of the hydrophobic and hydrophilic parts of the amphiphilic molecule and external factors such as temperature and solvent composition. A low critical micelle concentration indicates a micelle stable at low surfactant concentration, which is of importance in biological applications, where the desired activity (e.g. cell targeting and delivery) is dependent upon retention of the micelle-like structure even after high overall dilution. SVLPs according to the invention remain thermodynamically stable in the low nanomolar region, indicating that they are ideal for the purpose of vaccine delivery. The high stability arises from the unique molecular architecture of SVLPs. Moreover, SVLPs can be made with relatively homogeneous size and shape distributions. SVLPs according to the invention are not like liposomes, which possess a bilayer membrane structure enclosing an aqueous solution in the core. SVLPs will be more stable in vivo than liposomes as they do not expose large areas of lipid membrane to the aqueous exterior.

In another aspect, the present invention provides for a pharmaceutical composition comprising an immunologically effective amount of the cyclic peptide of the present invention, the conjugate of the present invention or the synthetic virus like particle of the present invention, together with a pharmaceutically acceptable diluent, carrier or excipient, wherein preferably said pharmaceutical composition is a vaccine.

As used herein, the term "effective amount" refers to an amount necessary or sufficient to realize a desired biologic effect. Preferably, the term "effective amount" refers to an amount of the cyclic peptide of the present invention, the conjugate of the present invention or the synthetic virus like particle of the present invention that (i) treats or prevents the particular disease, medical condition, or disorder, (ii) attenuates, ameliorates, or eliminates one or more symptoms of the particular disease, medical condition, or disorder, or (iii) prevents or delays the onset of one or more symptoms of the particular disease, medical condition, or disorder described herein.

An immunogenically effective amount, as herein understood, is an amount that is capable of modulating, preferably enhancing the response of the immune system of a subject to an antigen or pathogen.

The invention further relates to the cyclic peptide, the conjugate or the synthetic virus like particle of the invention for use as a vaccine. A vaccine, as used herein, is a pharmaceutical composition that is used to modulate, preferably to stimulate the response of the body's immune system to a particular antigen or pathogen.

In a preferred embodiment, the vaccine of the invention comprises an adjuvant. An adjuvant, as used herein, is a component that modulates, preferably enhances, the desired immune response to a vaccine or antigen.

In a preferred embodiment, the pharmaceutical composition or preferably the vaccine is used for preventing or reducing the risk of an RSV infection in a subject, preferably a human, more preferably a child or elderly people.

The vaccine may also comprise one or more adjuvants such as a mineral salt (e.g. aluminum hydroxide, aluminum phosphate, aluminum sulfate, calcium phosphate), monophosphoryl lipid A (MPL), plant extracts containing saponins (e.g. QS-21), imidazo-quinolines (e.g. imiquimod), muramyl dipeptides and tripeptides, lipopeptides, oil-in-water emulsions (e.g. Montanide ISA 720), cytokines (e.g. IL-2 or GM-CSF), mycobacterial and bacterial derivatives (e.g. Freund's complete adjuvant), BCG, nucleic acid derivatives (e.g. polyLC) and other adjuvants known to those skilled in the art.

Some components of the pharmaceutical composition or vaccine may also be encapsulated in or attached to polymers, which may for example be useful for controlled release, for example polylactic acid, poly-epsilon-caprolactone, polyhydroxybutyric acid, polyorthoesters, polyacetals, polydihydropyrans, polycyanoacrylates, and cross-linked or amphipathic block copolymers of hydrogels, or may be formulated in liposomes. The pharmaceutical composition or vaccine is prepared in a manner known per se, for example by means of conventional dissolving and lyophilizing processes and/or may comprise excipients, for example preservatives, stabilizers, wetting agents, tonicity adjusting agents and/or emulsifiers, solubilizers, salts for regulating osmotic pressure and/or buffering substances to stabilize the pH. The pharmaceutical composition or vaccine may be in liquid form or solid (e.g. lyophilized) form and can be sterilized by conventional, well-known sterilization techniques or sterile filtered. The resulting aqueous solution can be packaged for use as it is, or lyophilized, spray dried, or the solvent can be removed in another way. The solid form may be combined with a sterile diluent (e.g., water) prior to administration or may be administered as it is. Likewise, the pharmaceutical composition or vaccine may comprise an emulsion, dispersion or suspension or any other form suitable for the intended route of administration.

The pharmaceutical composition or vaccine may be administered by any suitable enteral or parenteral route, such as the intranasal, oral, sublingual, intramuscular, intradermal, and subcutaneous. Other routes are known in the art that could also be employed. A device may be used for administration, such as conventional needles and syringes, micro needles, spray devices and the like, depending on the dose form and administration route. The device may be pre-filled with the pharmaceutical composition or vaccine.

The effective dosage of cyclic peptide, the conjugate or the synthetic virus like particle depends upon the intended recipient (e.g. species), its age, weight and individual condition, and the administration route. An optimal dosage of the cyclic peptide, the conjugate or the synthetic virus like particle for a particular target population can be determined by standard studies involving observation of appropriate immune responses in subjects. The amount of said pharmaceutical composition or said vaccine sufficient to evoke or modulate an immune response or to confer immunity against a pathogenic organism, preferably an RSV is determined by methods well known to those skilled in the art. This amount can be determined based upon the characteristics of the recipient and the desired level of immunity, e.g., to an RSV infection.

Said pharmaceutical composition or said vaccine may be administered as a single dose or in a dosage regimen, e.g., as two or more doses at adequately spaced time points. Said pharmaceutical composition or said vaccine may also be administered together with other active agents, pharmaceutical compositions or vaccines. Preferably, the vaccine of the invention may be used in prime-boost regimens in combination with other vaccines.

In again another aspect, the present invention provides for the cyclic peptide of the present invention, the conjugate of the present invention or the synthetic virus like particle of the present invention for use as a medicament, preferably for preventing an infectious disease or reducing the risk of an infectious disease, more preferably for preventing or reducing the risk of an infectious disease associated with or caused by a respiratory syncytial virus. The present invention provides for the cyclic peptide of the invention, the conjugate of the invention, the synthetic virus like particle of the invention, or the pharmaceutical composition of the invention for use as a medicament, preferably for use in a method for preventing an infectious disease or for reducing the risk of an infectious disease, more preferably for use in a method for preventing or reducing the risk of an infectious disease associated with or caused by a respiratory syncytial virus (RSV).

The present invention provides for the cyclic peptide of the invention, the conjugate of the invention, the synthetic virus like particle of the invention, or the pharmaceutical composition of the invention for use as a medicament, preferably for use in a method for preventing an infection or for reducing the risk of an infection, more preferably for use in a method for preventing or reducing the risk of an infection caused by a respiratory syncytial virus.

The present invention provides for the cyclic peptide of the invention, the conjugate of the invention, the synthetic virus like particle of the invention, or the pharmaceutical composition of the invention for use as a medicament, preferably for use in a method for preventing an infection or for reducing the risk of an infection, more preferably for use in a method for preventing or reducing the risk of an RSV infection.

The invention further relates to a method of eliciting or modulating an immune response or to a method of limiting the risk of developing a disease, preferably an infection, more preferably an infection associated with or caused by an RSV, wherein an immunogenically effective amount of the cyclic peptide, the conjugate or the synthetic virus like particle of the invention is administered to a subject, preferably a human, more preferably a child or elderly people. The invention further relates to a method for treating a disease, preferably an infection, more preferably an infection associated with or caused by an RSV, comprising administering an immunogenically effective amount of the cyclic peptide, the conjugate or the synthetic virus like particle of the invention to a subject, preferably a human, more preferably a child or elderly people. Moreover, the invention relates to the cyclic peptide, the conjugate or the synthetic virus like particle of the invention for use in treating a disease, preferably an infection associated with or caused by an RSV.

The invention further relates to a method of eliciting or modulating an immune response or to a method of limiting the risk of developing a disease, preferably an infection, more preferably an infection caused by an RSV, wherein an immunogenically effective amount of the cyclic peptide, the conjugate or the synthetic virus like particle of the invention is administered to a subject, preferably a human, more preferably a child or elderly people. The invention further relates to a method for treating a disease, preferably an infection, more preferably an infection caused by an RSV, comprising administering an immunogenically effective amount of the cyclic peptide, the conjugate or the synthetic virus like particle of the invention to a subject, preferably a human, more preferably a child or elderly people. Moreover, the invention relates to the cyclic peptide, the conjugate or the synthetic virus like particle of the invention for use in treating a disease, preferably an infection caused by an RSV.

The invention further relates to a method of eliciting or modulating an immune response or to a method of limiting the risk of developing a disease, preferably an infection, more preferably an RSV infection, wherein an immunogenically effective amount of the cyclic peptide, the conjugate or the synthetic virus like particle of the invention is administered to a subject, preferably a human, more preferably a child or elderly people. The invention further relates to a method for treating a disease, preferably an infection, more preferably an RSV infection, comprising administering an immunogenically effective amount of the cyclic peptide, the conjugate or the synthetic virus like particle of the invention to a subject, preferably a human, more preferably a child or elderly people. Moreover, the invention relates to the cyclic peptide, the conjugate or the synthetic virus like particle of the invention for use in treating a disease, preferably an RSV infection.

EXAMPLES

Example 1

Design and Synthesis of RSV Peptides

Maleimido-Peptide 1

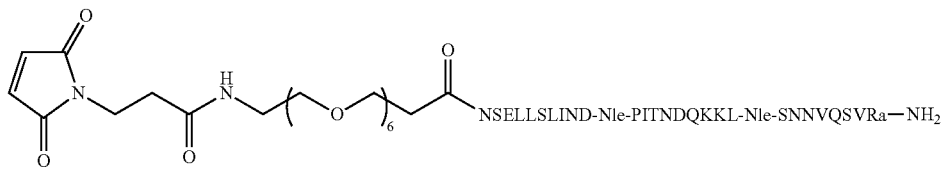

(1)

In the synthesis of maleimido-peptide 1 (SEQ ID NO: 14), 3-(maleimido)propionic acid is coupled to the N-terminus via a 21-amino-3,6,9,12,15,18-hexaoxaheneicosan-21-oic amide linker in order to enable conjugation to a lipopeptide.

A D-Ala (denoted as "a") is coupled to the C-terminus as the amide in order to confer stability to exoproteases.

The synthesis of maleimido-peptide 1 was carried out using Fmoc solid phase peptide synthesis (SPPS) methods as follows: The peptide NSELLSLIND-Nle-PITNDQKKL-Nle-SNNVQSVRa was assembled on Tentagel R Ram resin on 0.5 mmol scale using standard Fmoc solid phase peptide synthesis methods. The following amino acids were used (in the correct order): Fmoc-D-Ala-OH, Fmoc-21-amino-3,6,9,12,15,18-hexaoxaheneicosan-21-oic acid (Fmoc-PEO6-OH), Fmoc-Arg(Pbf)-OH, Fmoc-Asn(Trt)-OH, Fmoc-Asp (OtBu)-OH, Fmoc-Glu(OtBu)-OH, Fmoc-Gln(Trt)-OH, Fmoc-Dab(Boc)-OH, Fmoc-Ile-OH, Fmoc-Leu-OH, Fmoc-Lys(Boc)-OH, Fmoc-Nle-OH, Fmoc-Pro-OH, Fmoc-Ser(tBu)-OH, Fmoc-Thr(tBu)-OH and Fmoc-Val-OH. 3-Maleimido-propionic acid was coupled to the N-terminus using PyBOP for activation. After completion of assembly, the peptide was cleaved from the resin and the side-chain protecting groups were removed by treatment with TFA/TIS/TA/phenol 85:5:5:5. The peptide was precipitated and washed with iPr$_2$O, dried in vacuo, purified by RP-HPLC on a preparative C18 column and lyophilized to afford 1 as a white powder. Maleimido-peptide 1 was analyzed by RP-HPLC using an Agilent Zorbax Eclipse analytical column (C8, 5 μm, 4.6 mm×250 mm) and a linear gradient of 12.5-60.0% MeCN in H$_2$O (+0.1% TFA) in 25 min: Purity: 80.9%; t$_R$=17.73 min. ESI-MS: MW calculated for C$_{165}$H$_{281}$N$_{45}$O$_{58}$: 3823.26 Da; MW found: 3822.35 Da (±0.01%).

(Aminooxy)acetyl Peptide 2 stirred overnight. The cyclic peptide was then purified by RP-HPLC on a preparative C18 column and lyophilized to afford 2 as a white powder. Analytical RP-HPLC (Agilent Eclipse XDB C18, 5 μm, 4.6 mm×250 mm column, 12.5-60.0% MeCN in H$_2$O (+0.1% TFA) over 25 min): Purity: 80.4%; t$_R$=14.53 min. ESI-MS: MW calculated for C$_{154}$H$_{267}$N$_{45}$O$_{56}$S$_2$: 3709.21 Da; MW found: 3707.57 Da (±0.01%).

(Aminooxy)acetyl Peptide 3

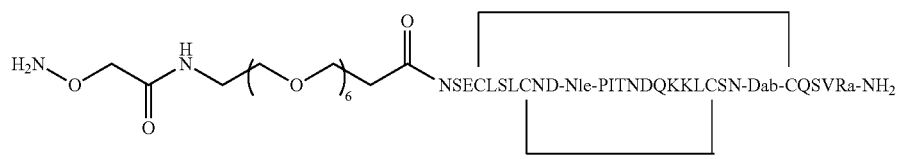

(3)

In (aminooxy)acetyl peptide 3 (SEQ ID NO: 16), an (aminooxy)acetyl moiety (denoted as "AOAc") is coupled to the N-terminus of the peptide via a 21-amino-3,6,9,12,15,18-hexaoxaheneicosan-21-oic amide linker, and a D-Ala (denoted as "a") is coupled to the C-terminus as the amide in order to confer stability to exoproteases. The (aminooxy)acetyl peptide contains two disulfide bonds as depicted in formula (3).

(Aminooxy)acetyl peptide 3 was synthesized and purified essentially as described above for peptide 2. Analytical RP-HPLC (Agilent Eclipse XDB C18, 5 μm, 4.6 mm×250 mm column, 12.5-60% MeCN in H$_2$O (+0.1% TFA) over 25 min): Purity: 98.7%; t$_R$=12.13 min. ESI-MS: MW calculated for C$_{149}$H$_{255}$N$_{45}$O$_{56}$S$_4$: 3701.18 Da; MW found: 3701.3 Da (0.01%).

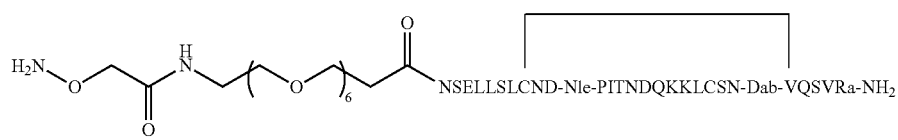

(2)

In (aminooxy)acetyl peptide 2 (SEQ ID NO: 15), an (aminooxy)acetyl moiety (denoted as "AOAc") is coupled to the N-terminus of the peptide via a 21-amino-3,6,9,12,15,18-hexaoxaheneicosan-21-oic amide linker, and a D-Ala (denoted as "a") is coupled to the C-terminus as the amide in order to confer stability to exoproteases. The (aminooxy)acetyl peptide contains one disulfide bond between the two Cys residues.

Peptide 2 was synthesized using standard Fmoc solid phase peptide synthesis as described above for peptide 1. AOAc was coupled as Bis-Boc-aminooxy-acetic acid N-hydroxysuccinimide ester (Boc$_2$-Aoa-OSu). After completion of assembly the peptide was cleaved from the resin and the side-chain protecting groups were removed by treatment with 87.5% TFA, 5% TA, 5% H$_2$O, 2.5% EDT for 2.5 h. For cyclization by air oxidation, the reduced peptide was dissolved in 0.33 M ammonium bicarbonate buffer, pH 7.8 and (Aminooxy)acetyl Peptide 4

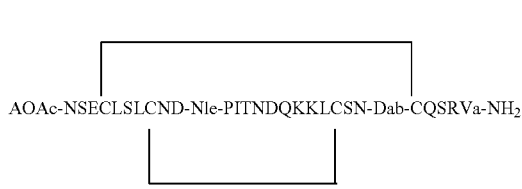

(4)

In (aminooxy)acetyl peptide 4 (SEQ ID NO: 17), an (aminooxy)acetyl moiety (denoted as "AOAc") is coupled to the N-terminus of the peptide and a D-Ala (denoted as "a") is coupled to the C-terminus as the amide in order to confer stability to exoproteases. The (aminooxy)acetyl peptide contains two disulfide bonds as depicted in formula (4).

(Aminooxy)acetyl peptide 4 was synthesized and purified essentially as described above for (Aminooxy)acetyl peptide 2. Analytical RP-HPLC (Vydac 218TP54, 5 µm, 4.6 mm×250 mm column, 0-60% MeCN in H$_2$O (+0.1% TFA) over 40 min): Purity: 90.4%; t$_R$=25.07 min. MALDI-MS: MW calculated for C$_{134}$H$_{226}$N$_{44}$O$_{49}$S$_4$: 3365.78 Da; MW found: 3365.80 Da (±0.01%).

(Aminooxy)acetyl Peptide 5

(5)

In (aminooxy)acetyl peptide 5 (SEQ ID NO: 18), an (aminooxy)acetyl moiety (denoted as "AOAc") coupled to a lysine side chain in the peptide, the N-terminus is acetylated and a D-Ala (denoted as "a") is coupled to the C-terminus as the amide in order to confer stability to exoproteases. The (aminooxy)acetyl peptide contains two disulfide bonds as depicted in formula (5).

(Aminooxy)acetyl peptide 5 was synthesized and purified essentially as described above for (Aminooxy)acetyl peptide 2. For coupling of Lys(AOAc), Fmoc-Lys(Mtt)-OH was used instead of Fmoc-Lys(Trt)-OH and the Mtt protecting group was selectively cleaved with 3% TFA in DCM and Boc$_2$-Aoa-OSu was coupled to the liberated Lys side-chain amino group. After assembly of the peptide chain and removal of the terminal Fmoc protecting group the N-Terminus was acetylated with 0.5 M Ac2O, 0.05 M HOBt and 0.136 M DIEA in NMP. Analytical RP-HPLC (Agilent Eclipse XDB-C18, 5 µm, 4.6 mm×250 mm column, 0-60% MeCN in H$_2$O (+0.1% TFA) over 40 min): Purity: 95.4%; t$_R$=25.12 min. ESI-MS: MW calculated for C$_{138}$H$_{232}$N$_{44}$O$_{50}$S$_4$: 3435.87 Da; MW found: 3435.40 Da (±0.01%).

(Aminooxy)acetyl Peptide 6

(6)

AOAc-RLSECLSLCND-Nle-PITNDQKKLCSNNCLKSa-NH$_2$

In (aminooxy)acetyl peptide 6 (SEQ ID NO: 19), an (aminooxy)acetyl moiety (denoted as "AOAc") is coupled to the N-terminus of the peptide and a D-Ala (denoted as "a") is coupled to the C-terminus as the amide in order to confer stability to exoproteases. The (aminooxy)acetyl peptide contains two disulfide bonds as depicted in formula (6).

(Aminooxy)acetyl peptide 6 was synthesized and purified essentially as described above for (Aminooxy)acetyl peptide 2. Analytical RP-HPLC (Agilent Eclipse XDB-C18, 5 µm, 4.6 mm×250 mm column, 0-60% MeCN in H$_2$O (+0.1% TFA) over 25 min): Purity: 93.1%; t$_R$=13.5 min. ESI-MS: MW calculated for C$_{138}$H$_{235}$N$_{43}$O$_{48}$S$_4$: 3390.62 Da; MW found: 3390.86 Da (0.01%).

(Aminooxy)acetyl Peptide 7

(7)

AOAc-PVSTYMLTNSECLSLCNDMPITNDQKKLCSNNCQIVRQQa-NH$_2$

In (aminooxy)acetyl peptide 7 (SEQ ID NO: 20), an (aminooxy)acetyl moiety (denoted as "AOAc") coupled to the N-terminus of the peptide and a D-Ala (denoted as "a") is coupled to the C-terminus as the amide in order to confer stability to exoproteases. The (aminooxy)acetyl peptide contains two disulfide bonds as depicted in formula (7).

(Aminooxy)acetyl peptide 7 was synthesized on 0.5 mmol scale, oxidized and purified essentially as described above for (Aminooxy)acetyl peptide 2. Analytical RP-HPLC (Vydac 218TP54, 5 µm, 4.6 mm×250 mm column, 0-60% MeCN in H$_2$O (+0.1% TFA) over 40 min): Purity: 90.1%; t$_R$=28.16 min. MALDI-MS: MW calculated for C$_{187}$H$_{308}$N$_{56}$O$_{65}$S$_6$: 4573.24 Da; MW found: 4573.05 Da (±0.01%).

Example 2

Preparation of Inventive Conjugates for Immunizations

For immunizations the conjugates, according to the general Scheme A-B-C where "A" denotes the antigen. In particular, antigen A1 comprises SEQ ID NO: 37, antigen A2 comprises SEQ ID NO: 38, antigen A3 comprises the inventive SEQ ID NO: 2, and antigen A4 comprises the inventive SEQ ID NO: 3. "B" denotes the linker and "C" the lipopeptide building block, respectively. "X" denotes the attachment to the lipopeptide building block C. Moreover, specific used linker and lipopeptide intermediates are further shown below.

Antigens A:

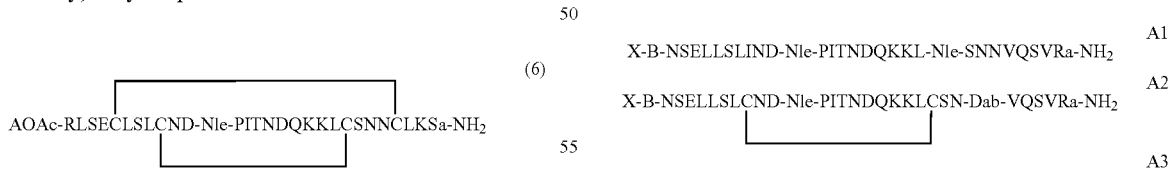

Linkers B:
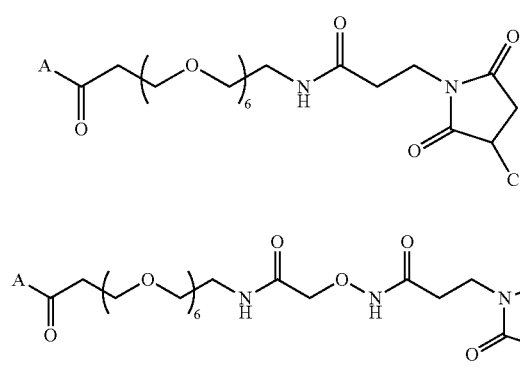
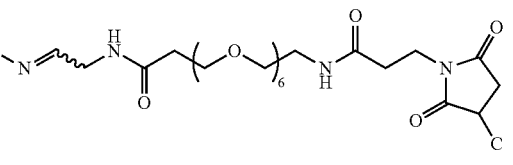
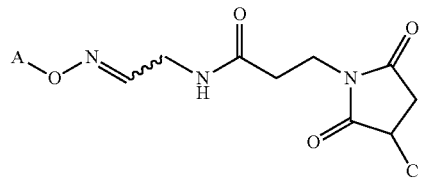
Lipopeptides Building Blocks C:
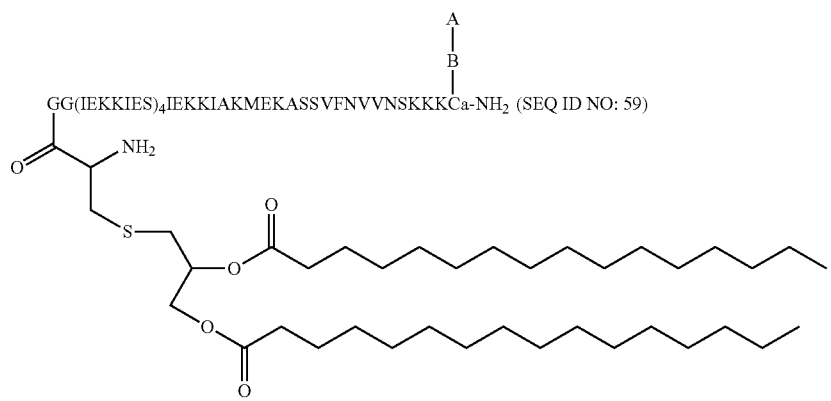
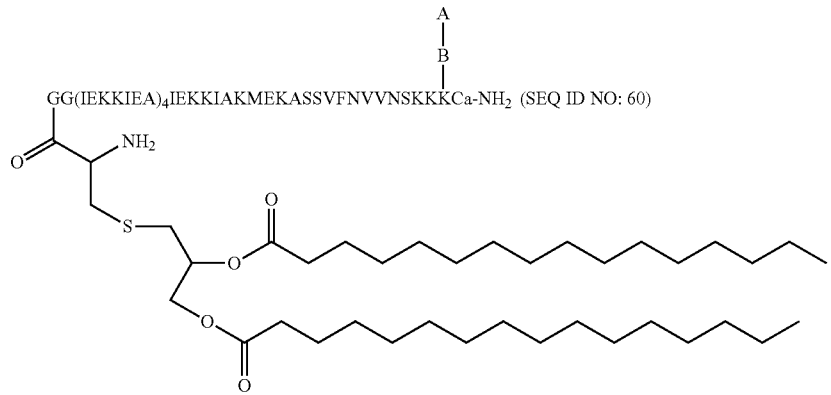

Synthesis of Maleimide PEG6 Aldehyde Linker Compound 8

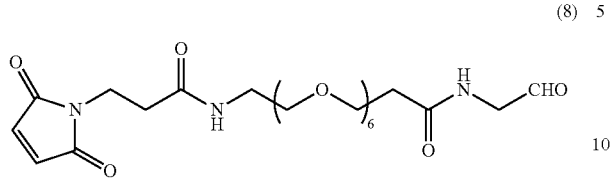
(8)

Linker compound 8 was synthesized by reacting SM-PEG$_6$ (Thermo Fisher Scientific) with aminoacetaldehyde dimethyl acetal in H$_2$O. SM-PEG$_6$ (7.6 mg, 12.6 µmol) was suspended in 0.3 ml H$_2$O and 17 µl of a 1:10 (v/v) solution of aminoacetaldehyde dimethyl acetal in H$_2$O was added. The mixture was stirred for 90 min. at r.t. The cross-linker was purified by RP-HPLC on a C8 column and lyophilized. ESI-MS: MW calculated for C$_{26}$H$_{45}$N$_3$O$_{12}$: 591.66; MW found: 591.32 (±0.05%). For hydrolysis of the dimethyl acetal the linker 8 (20 mg) was treated with 95% TFA, 5% H$_2$O for 5 min. The TFA was removed in vacuo. ESI-MS C$_{24}$H$_{39}$N$_3$O$_{11}$: 545.59 Da; MW found: 545.28 Da (±0.05%).

Synthesis of Maleimide C3 Aldehyde Linker Compound 9

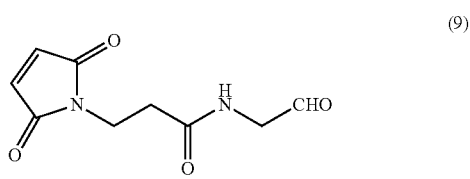 [SMILES: O=CCNC(=O)CCN1C(=O)C=CC1=O]
(9)

Linker compound 9 was synthesized by reacting 3-(maleimido)-propionic acid N-hydroxysuccinimide ester with aminoacetaldehyde dimethyl acetal in H$_2$O and the linker was purified as described above for 8. ESI-MS: MW calculated for C$_{11}$H$_{16}$N$_2$O$_5$: 256.26; MW found: 256.39 (±0.05%). The acetal was cleaved essentially as described above for 8. ESI-MS C$_9$H$_{10}$N$_2$O$_4$: 210.19; MW found: 210.23 (±0.02%).

Lipopeptide 10

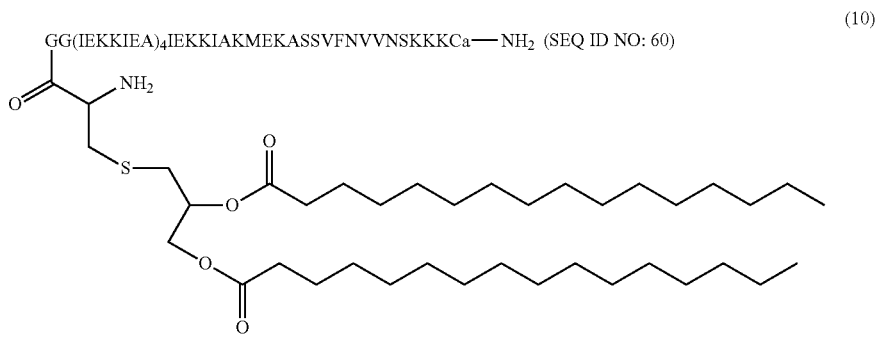
(10)

GG(IEKKIEA)$_4$IEKKIAKMEKASSVFNVVNSKKKCa—NH$_2$ (SEQ ID NO: 60)

The synthesis of lipopeptide 10 was carried out, and the product was purified by RP-HPLC essentially as described in WO 2008/068017. The lipopeptide 10 was analyzed by analytical RP-HPLC and MALDI-TOF. Analytical RP-HPLC (Agilent VariTide RPC, 0 to 95% MeCN in H$_2$O (+0.1% TFA) over 63 min.): Purity=96.9%, t$_R$=22.71 min. MALDI-TOF: MW calculated for C$_{312}$H$_{552}$N$_{74}$O$_{85}$S$_3$: 6796.46 Da; MW found: 6796.42 Da (±0.05%).

Lipopeptide 11

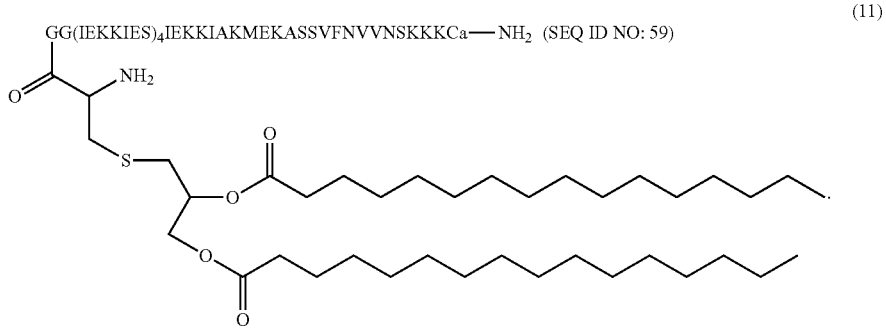
(11)

GG(IEKKIES)$_4$IEKKIAKMEKASSVFNVVNSKKKCa—NH$_2$ (SEQ ID NO: 59)

This lipopeptide 11 contains a coiled-coil domain, which has serine in the "c" positions of the heptad repeat "defgabc" IEKKIES (SEQ ID NO: 13).

The lipopeptide 11 was synthesized and purified by RP-HPLC as described above for lipopeptide 10 and analyzed by analytical RP-HPLC and MALDI-MS. Analytical RP-HPLC (Agilent VariTide RPC, 0 to 95% MeCN in $H_2O$ (+0.1% TFA) over 63 min.): Purity 97.0%, $t_R$=45.58 min. MALDI-MS: MW calc. for $C_{312}H_{552}N_{74}O_{89}S_3$: 6860.46 Da; found 6860.61 Da (0.05%).

Conjugate 12 (Antigen A3+Linker B3+Lipopeptide Building Block C1)

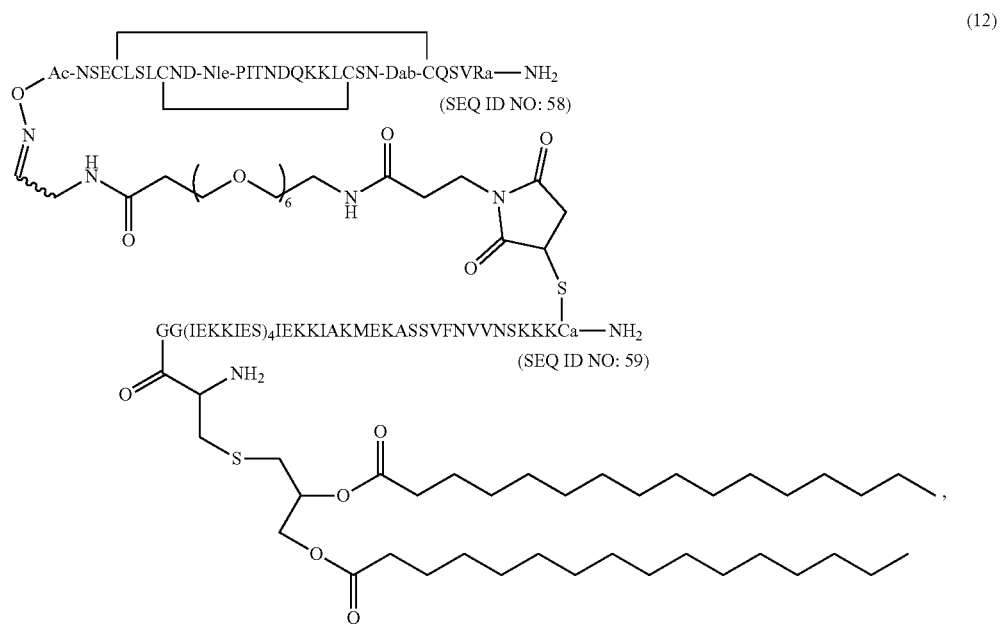

(12)

To prepare conjugate 12, a solution of (aminooxy)acetyl peptide 4 (12 mg, 3.6 μmol) in 0.25 ml 0.1 M sodium acetate buffer, pH 3.5 was added to linker compound 8 (3.8 mg, 7.2 μmol) in 0.25 ml 0.1 M sodium acetate buffer, pH 3.5. The mixture was stirred for 2.5 h and the oxime was purified by RP-HPLC on a preparative C8 column. The intermediate was analyzed by analytical UPLC (ACQUITY UPLC BEH C8, 1.7 μm, 2.1×150 mm, 10 to 70% MeCN in $H_2O$ (+0.1% TFA) over 60 min., 70° C.): Purity 95%, $t_R$=16.59 min. ESI-MS: MW calculated for $C_{158}H_{263}N_{47}O_{59}S_4$: 3893.35 Da; MW found: 3892.35 (±0.01%). The oxime (4.0 mg, 1.0 μmol) was dissolved in 0.5 ml $H_2O$ and added to a solution of lipopeptide 11 (6.2 mg, 0.9 μmol) in 2 ml 50% MeCN. The pH was adjusted to pH=6.5 with 0.1 N NaOH/0.1 N HCl and the mixture was stirred at r.t. for 2.5 h. The conjugate 12 was purified by HPLC on a C8 column. The TFA was removed using AG-X2 anion exchange resin (acetate form). The conjugate was analyzed by analytical UPLC and MS. UPLC (ACQUITY UPLC BEH C8, 1.7 μm, 2.1×150 mm 40 to 80% MeCN in $H_2O$ (+0.1% TFA) over 50 min., 40° C.): Purity 94%, $t_R$=20.75 min. ESI-MS: MW calc. for $C_{470}H_{815}N_{121}O_{148}S_7$: 10753.81 Da; found 10751.1 Da (±0.05%).

Conjugate 12 was suspended in PBS, equilibrated for 30 minutes, diluted to 1.0 mg/ml and analyzed by Dynamic Light Scattering (DLS) on a Wyatt DynaPro Nanostar instrument at 25° C. The size distribution by regularization analysis was monomodal and the size dispersity was small. The mean hydrodynamic radius ($R_h$) was 13.1 nm, and the Pd Index was 0.038, respectively. Similar values were obtained at other concentrations and temperatures.

Conjugate 13 (Antigen A3+Linker B3+Lipopeptide C2)

(13)

Ac-NSECLSLCND-Nle-PITNDQKKLCSN-Dab-CQSVRa-NH₂ (SEQ ID NO: 58)

GG(IEKKIEA)₄IEKKIAKMEKASVFNVVNSKKKCa-NH₂ (SEQ ID NO: 60)

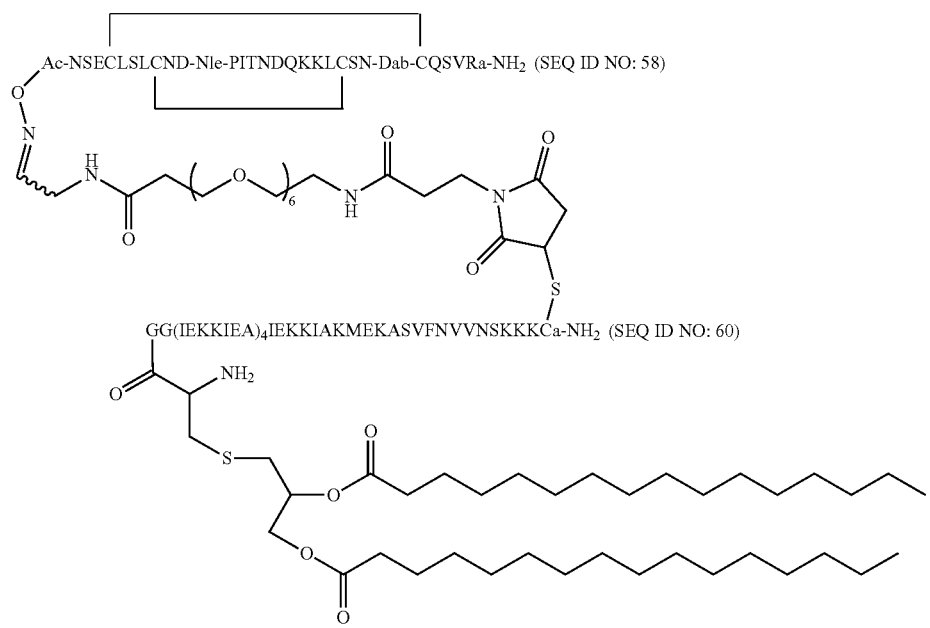

Conjugate 13 was prepared and purified essentially as described above for conjugate 12 except that lipopeptide 10 was used instead of 11. Analytical UPLC (ACQUITY UPLC BEH C8, 1.7 µm, 2.1×150 mm 10 to 90% MeCN in H₂O (+0.1% TFA) over 45 min., 40° C.): Purity 79%, $t_R$=32.43 min. MALDI-MS: MW calc. for $C_{470}H_{815}N_{121}O_{144}S_7$: 10689.8 Da; found 10687.7 Da (±0.05%). DLS (PBS, 25° C.): $R_h$=20.4 nm, and Pd Index=0.034.

Conjugate 14 (Antigen A3+Linker B4+Lipopeptide C1)

Conjugate 14 was prepared and purified essentially as described above for conjugate 12 except that linker compound 9 was used instead of 8. Analytical UPLC (ACQUITY UPLC BEH C8, 1.7 µm, 2.1×150 mm 40 to 80% MeCN in H₂O (+0.1% TFA) over 50 min., 40° C.): Purity 75%, $t_R$=19.37 min. ESI-MS: MW calc. for $C_{456}H_{788}N_{120}O_{141}S_7$: 10432.44 Da; found 10433.66 Da (±0.01%). DLS (PBS, 25° C.): $R_h$=13.7 nm, and Pd Index=0.033.

(14)

Ac-NSECLSLCND-Nle-PITNDQKKLCSN-Dab-CQSVRa—NH₂
(SEQ ID NO: 58)

GG(IEKKIES)₄IEKKIAKMEKASSVFNVVNSKKKCa—NH₂
(SEQ ID NO: 59)

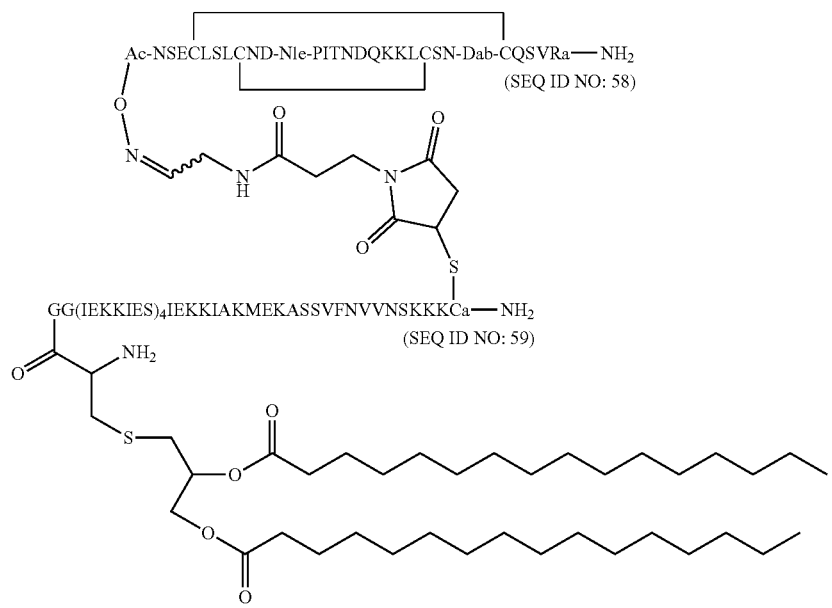

Conjugate 15 (Antigen A3+Linker B2+Lipopeptide C1)

(15)

NSECLSLCND-Nle-PITNDQKKLCSN-Dab-CQSVRa—NH₂
(SEQ ID NO: 61)

GG(IEKKIES)₄IEKKIAKMEKASSVFNVVNSKKKCa—NH₂
(SEQ ID NO: 59)

Conjugate 15 was prepared and purified essentially as described above for conjugate 12 except that (aminooxy)acetyl peptide 3 and linker compound 3-maleoyl-beta-alanine NHS ester were used instead of (aminooxy)acetyl peptide 4 and linker compound 8, respectively. Analytical UPLC (ACQUITY UPLC BEH C8, 1.7 μm, 2.1×150 mm 10 to 90% MeCN in H₂O (+0.1% TFA) over 45 min., 40° C.): Purity: 80%, $t_R$=37.97 min. ESI-MS: MW calc. for $C_{468}H_{812}N_{120}O_{148}S_7$: 10712.8 Da; found 10713.8 Da (±0.05%). DLS (PBS, 25° C.): $R_h$=14.53 nm, and Pd Index=0.022.

Conjugate 16 (Antigen A4+Linker B3+Lipopeptide C1)

Conjugate 16 was prepared and purified essentially as described above for conjugate 12 except that (aminooxy)acetyl peptide 5 was used instead of (aminooxy)acetyl peptide 4. Analytical UPLC (ACQUITY UPLC BEH C8, 1.7 μm, 2.1×150 mm 10 to 90% MeCN in H₂O (+0.1% TFA) over 45 min., 40° C.): Purity 79%, $t_R$=32.43 min. ESI-MS: MW calc. for $C_{474}H_{821}N_{121}O_{149}S_7$: 10823.9 Da; found 10822.7 Da (±0.05%). DLS (PBS, 25° C.): $R_h$=13.7 nm, and Pd Index=0.033.

(16)

Ac-NSECLSLCND-Nle-PITNDQKKLCSNKCQSVRa—NH₂
(SEQ ID NO: 62)

GG(IEKKIES)₄IEKKIAKMEKASSVFNVVNSKKKCa—NH₂
(SEQ ID NO: 59)

Conjugate 17 (Antigen A1+Linker B1+Lipopeptide C1)

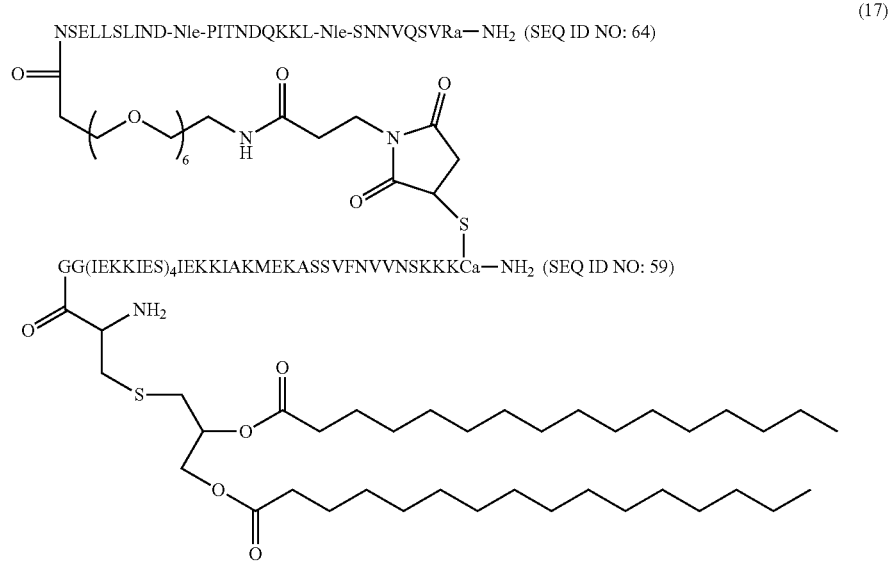

(17)

NSELLSLIND-Nle-PITNDQKKL-Nle-SNNVQSVRa—NH$_2$ (SEQ ID NO: 64)

GG(IEKKIES)$_4$IEKKIAKMEKASSVFNVVNSKKKCa—NH$_2$ (SEQ ID NO: 59)

To prepare conjugate 17, maleimido-peptide 1 (2.5 mg, 0.65 μmol) was dissolved in 1 ml H$_2$O and added to a solution of lipopeptide 11 (3.0 mg, 0.44 μmol) in 3 ml 50% MeCN. The pH was adjusted to pH=6.5 with 0.1 N NaOH/ 0.1 N HCl and the mixture was stirred at r.t. for 2.5 h. The conjugate 17 was purified by HPLC on a C8 column and analyzed by UPLC and MS. Analytical UPLC (ACQUITY UPLC BEH C8, 1.7 μm, 2.1×150 mm 10 to 90% MeCN in H$_2$O (+0.1% TFA) over 45 min., 40° C.): Purity 80%, $t_R$=32.43 min. MALDI-MS: MW calc. for C$_{477}$H$_{833}$N$_{119}$O$_{147}$S$_3$: 10683.78 Da; found 10684.2 Da (±0.05%). DLS (PBS, 25° C.): $R_h$=10.4 nm, Pd Index=0.034.

Conjugate 18 (Antigen A2+Linker B2+Lipopeptide C1)

Conjugate 18 was prepared and purified essentially as described above for conjugate 12 except that (aminooxy) acetyl peptide 2 and 3-maleoyl-beta-alanine NHS ester were used instead of 4 and 8, respectively. Analytical UPLC (ACQUITY UPLC BEH C8, 1.7 μm, 2.1×150 mm, 10 to 90% MeCN in H$_2$O (+0.1% TFA) over 45 min., 40° C.): Purity>79%, $t_R$=35.76 min. ESI-MS: MW calc. for C$_{472}$H$_{822}$N$_{120}$O$_{148}$S$_6$: 10738.82 Da; found 10757.51 Da (0.05%) (M+H$_2$O). %). DLS (PBS, 25° C.): $R_h$=8.4 nm, Pd Index=0.032.

(18)

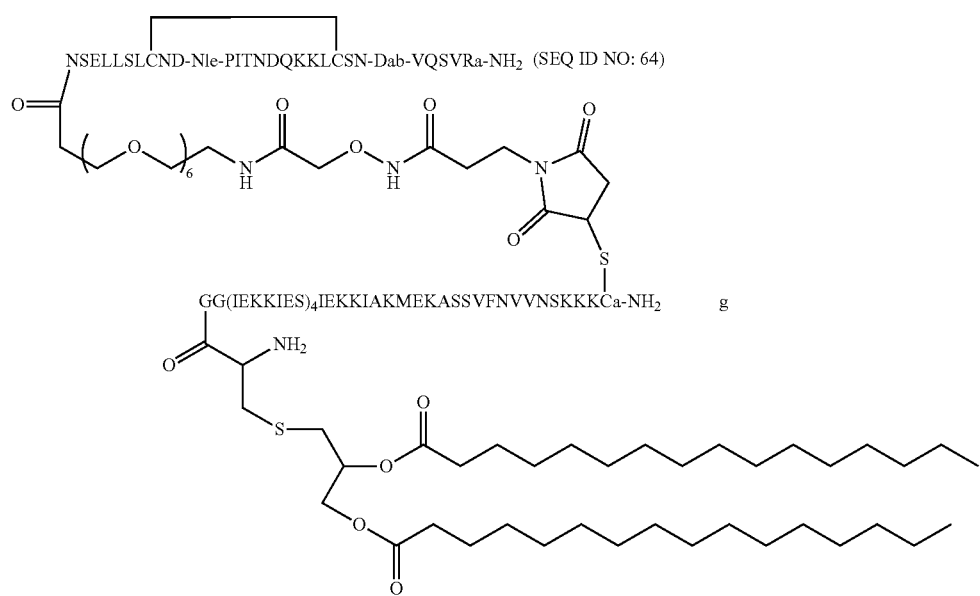

NSELLSLCND-Nle-PITNDQKKLCSN-Dab-VQSVRa-NH$_2$ (SEQ ID NO: 64)

GG(IEKKIES)$_4$IEKKIAKMEKASSVFNVVNSKKKCa-NH$_2$

Example 3

Immunogenicity Studies

Conjugates were tested for immunogenicity against RSV in mice. All experiments were performed in accordance with the general rules and regulations for the protection of animal rights and have been approved by the responsible authorities.

For the analysis of antibody responses, 6-8 week-old female BALB/c mice (5-6 animals per group) were subcutaneously immunized three times in three-week intervals subcutaneously with 0.1 ml of the formulations shown in Table 2. Control animals were immunized with PBS (vehicle) or formalin-inactivated RSV (FI-RSV) as shown in Table 2.

TABLE 2

Formulations used for immunizations

| No. | Description | Antigen A | Linker B | Lipopeptide C | Adjuvant |
|---|---|---|---|---|---|
| 1 | 12 in PBS | A3 | B3 | C1 | none |
| 2 | 13 in PBS | A3 | B3 | C2 | none |
| 3 | 14 in PBS | A3 | B4 | C1 | none |
| 4 | 15 in PBS | A3 | B2 | C1 | None |
| 5 | 16 in PBS | A4 | B4 | C1 | none |
| 6 | 17 in PBS | A1 | B1 | C1 | none |
| 7 | 18 in PBS | A2 | B2 | C1 | none |
| 8 | FI-RSV | — | — | — | none |
| 9 | PBS | — | — | — | none |

Blood was collected before the first and 10 days after the third immunization, and the sera were analyzed by enzyme linked immunosorbent assay (ELISA) for antibodies binding to SEQ ID NO: 2 and by RSV neutralizing antibody assay (60% plaque reduction neutralization test) for neutralizing antibodies against RSV A2 and A/Long strains.

The ELISA was performed essentially as described in WO 2008/068017. Briefly, MaxiSorp 96-well microtitre plates (Nunc, Fischer Scientific) were coated at 4° C. overnight with 5 µl/ml solutions of peptide 4 in PBS, pH 7.2 in 50 mM sodium carbonate buffer. The wells were washed with PBS containing 0.05% Tween 20 (PBST) and blocked with PBS containing 5% skimmed milk powder for 1 h at r.t. After blocking, the wells were washed three times with PBST and incubated with serial four fold-dilutions of mouse sera in PBS containing 0.05% Tween 20 and 0.5% skimmed milk powder (MPBST) for 2 h at r.t., followed by three washes with PBST. The plates were then incubated with anti-Mouse IgG (Fc specific)-peroxidase antibody produced in goat (Sigma, St. Louis, Mo.), diluted 1:15'000 in MPBST for 1 h at r.t., washed again three times with PBST and incubated in the dark with 3,3',5,5'-Tetramethylbenzidine (TMB) solution (T0440, Sigma) for 15 min. The color reaction was stopped by addition of 0.16 M $H_2SO_4$ and the absorbance in the wells was read at 450 nm on a plate reader. IgG titers were calculated as reciprocal serum dilutions corresponding to half-maximal binding concentrations ($EC_{50}$) were. Mean titers±one standard errors are summarized for each group in Table 3.

For the RSV neutralization antibody assay (60% plaque reduction neutralization test), sera were heat inactivated 30 min. at 56° C., diluted 1:10 with EMEM and serially diluted further 1:4. Diluted serum samples were incubated with equal volumes of RSV/A2 (25-50 PFU) for 1 hour at room temperature and inoculated in duplicates onto confluent HEp-2 monolayers in 24 well plates. After one hour of incubation at 37° C. in a 5% CO2 incubator, the wells were overlaid with 0.75% Methylcellulose medium. After 4 days of incubation, the overlays were removed and the cells were fixed and stained with 0.1% crystal violet for one hour and then rinsed and air-dried. Neutralization titers were calculated as reciprocal serum dilutions required to reach 60% plaque reduction versus virus control wells. Mean titers±one standard errors are summarized in Table 3.

TABLE 3

Antibody responses after immunization with different formulations

| | | Anti-RSV IgG titer ($log_{10}$) | | RSV neutralization titer ($log_2$) | |
|---|---|---|---|---|---|
| No. | Description | Pre-immune sera | Post-immunization Sera | Pre-immune sera | post-immunization sera |
| 1 | 12 in PBS | <2.30 | 4.46 ± 0.06 | <4.32 | 6.75 ± 0.66 |
| 2 | 13 in PBS | <2.30 | 4.39 ± 0.08 | <4.32 | 5.71 ± 0.71 |
| 3 | 14 in PBS | <2.30 | 4.48 ± 0.07 | <4.32 | 4.78 ± 0.39 |
| 4 | 15 in PBS | <2.30 | 5.19 ± 0.10 | <4.32 | 5.02 ± 0.51 |
| 5 | 16 in PBS | <2.30 | 3.4 ± 0.21 | <4.32 | 4.84 ± 0.42 |
| 6 | 17 in PBS | <2.30 | 3.40 ± 0.22 | <4.32 | <4.32 |
| 7 | 18 in PBS | <2.30 | 3.31 ± 0.21 | <4.32 | <4.32 |
| 8 | FI-RSV | <2.30 | <2.30 | <4.32 | <4.32 |
| 9 | PBS | <2.30 | <2.30 | <4.32 | <4.32 |

For determination of protection against challenge, groups of 6 mice were immunized with 150 µg conjugate in 0.1 ml PBS subcutaneously as described above. Control groups were immunized intramuscularly with FI-RSV or PBS. 10 days following the last immunization animals were challenged intranasally with 50 µl of RSV A2 at 105 PFU per animal. Five days after challenge, animals were euthanized, terminally bleed for determination of neutralizing antibodies by 60% plaque reduction neutralization test as described above and the lungs were harvested and bi-sected for viral titrations and histopathology analysis.

For viral titrations, lung homogenates were clarified by centrifugation and diluted in EMEM. Confluent HEp-2 monolayers were infected in duplicates with diluted homogenates in 24-well plates. After one hour of incubation at 37° C. in a 5% CO2 incubator, the wells were overlaid with 0.75% methylcellulose medium. After 4 days of incubation, the overlays were removed and the cells are fixed and stained with 0.10% crystal violet for one hour and then rinsed and air-dried. The plaques were counted and virus titers were expressed as plaque forming units per gram of tissue. Geometric mean viral titers±one standard error for all animals in a group are shown in Table 4. Non-detectable virus was expressed as <2.30 Log 10 PFU/gram For pulmonary histopathology, lungs were dissected and inflated with 10% neutral buffered formalin to their normal volume, and then immersed in the same fixative solution. Following fixation, the lungs are embedded in paraffin, sectioned and stained with hematoxylin and eosin (H&E). Four parameters of pulmonary inflammation are evaluated: peribronchiolitis (inflammatory cell infiltration around the bronchioles), perivasculitis (inflammatory cell infiltration around the small blood vessels), interstitial pneumonia (inflammatory cell infiltration and thickening of alveolar walls), and alveolitis (cells within the alveolar spaces). Slides were scored blind on a 0-4 severity scale. The scores were subsequently converted to a 0-100% histopathology scale. Average pathology scores±one standard error for each group are shown in Table 4.

TABLE 4

Protection from RSV challenge after immunization with different formulations

| No. | Description | Antibody neutralization titer ($\log_2$) | Lung virus titer (Log10 PFU/g) | Avg. pathology score (0-100%) |
|---|---|---|---|---|
| 1 | 12 in PBS | 6.58 ± 0.81 | <2.30 | 9.2 ± 4.3 |
| 2 | 13 in PBS | 4.63 ± 0.25 | 2.9 ± 0.37 | 12.9 ± 4.3 |
| 3 | FI-RSV | <2.32 | 3.34 ± 0.33 | 53.0 ± 14.5 |
| 4 | PBS | <2.32 | 4.52 ± 0.03 | 13.3 ± 4.5 |

The results demonstrate that immunization with conjugate 12, 13, and 15 elicits high neutralizing titers in serum without co-administration of an adjuvant. Lower but detectable titers were found in sera from animals immunized with conjugate 14 and 16 but not in sera from animals immunized with the corresponding linear or monocyclic peptide antigens (conjugates 17 and 18).

Immunization with conjugate 12 leads to full protection of the lungs (P-value of 0.002 versus PBS-immunized control animals, Logrank test) and reduced pulmonary histopathology after challenge, whereas only a partial reduction of virus in the lungs and strong histopathology is observed upon challenge after immunization with FI-RSV. Immunization with 13 also significantly reduces the virus-replication in the lungs and the pulmonary histopathology.

Example 4

Intramuscular Immunization and Co-Administration of Adjuvant

For this experiment 6-8 weeks old female BALB/c mice (twelve animals per group) were immunized two or three times by the intramuscular route with different doses of conjugate 12 in 0.1 ml PBS (Table 5, No. 1, 3 and 4). One additional group received 15 µg conjugate 12 adsorbed to aluminium phosphate adjuvant, Adju-Phos® (Brenntag) (Table 5, No. 2). Two control groups (6 animals per group) were immunized two times with FI-RSV and PBS, respectively (Table 5, No. 5 and 6).

TABLE 5

Formulations

| No. | Description | Dose | Adjuvant | Route |
|---|---|---|---|---|
| 1 | 12 in 0.1 ml PBS | 15 µg | none | IM |
| 2 | 12 in 0.1 ml PBS | 15 µg | Adju-Phos ® | IM |
| 3 | 12 in 0.1 ml PBS | 150 µg | none | IM |
| 4 | 12 in 0.1 ml PBS | 300 µg | none | IM |
| 5 | FI-RSV | 1:100 | none | IM |
| 6 | PBS | 0 | none | IM |

Animals were immunized on days 0 and 21. Blood was collected before the first immunization (D0) and on day 42 (D42). Six animals from groups 1 to 4 received an additional booster dose on D42 and the remaining animals where challenged intranasally with $10^6$ pfu RSV A2 live virus. Five days later, on day 47 (D47), animals were sacrificed and the lungs were harvested and bi-sected for viral titrations and histopathology analysis. Boosted animals were bled and challenged on day 63 (D63), and sacrificed on day 68 (D68).

Sera from D0, D42 and D63 were analyzed by 60% plaque reduction neutralization test (PRNT) for neutralizing antibodies against RSV A2 strain. Sera were heat-inactivated, diluted 1:10 with EMEM and serially diluted further 1:4. Diluted serum samples were incubated with RSV/A2 (25-50 PFU) for 1 h at room temperature and inoculated in duplicates onto confluent HEp-2 monolayers in 24-well plates. After 1 h incubation at 37° C. in a 5% CO2 incubator, the wells were overlaid with 0.75% methylcellulose. After 4 days of incubation, the overlays were removed, and the cells were fixed, stained with 0.1% crystal violet for 1 h and then rinsed and air dried. PRNT titers were determined at the 60% reduction end-point of the virus control. Geometric mean titers±one standard error are summarized in Table 6.

TABLE 6

Induction of Neutralizing antibodies.

| No. | Description | PRNT titer ($\log_2$) D0 | PRNT titer ($\log_2$) D42 | PRNT titer ($\log_2$) D68 |
|---|---|---|---|---|
| 1 | 15 µg 12 in PBS | <4.32 | 5.13 ± 0.42 | 6.07 ± 1.08 |
| 2 | 15 µg 12 in PBS + Adju-Phos ® | <4.32 | 6.40 ± 0.78 | 5.87 ± 0.69 |
| 3 | 150 µg 12 in PBS | <4.32 | 6.27 ± 0.82 | 7.16 ± 1.04 |
| 4 | 300 µg 12 in PBS | <4.32 | 6.45 ± 0.85 | 8.14 ± 0.94 |
| 5 | FI-RSV (1:100) | <4.32 | <4.32 | not determined |
| 6 | PBS | <4.32 | <4.32 | not determined |

Two immunizations with conjugate 12 induced high titers of neutralizing antibodies at doses ≥150 µg. The lower dose of 15 µg leads to lower titers of neutralizing antibodies, which could be increased by co-administration of adjuvant. An increase in PRNT titers was observed in D68 sera, which was dose dependent. Adju-Phos® did not have a benefit on the booster immunization.

For viral titrations, lung homogenates from D47 and D68 were clarified by centrifugation and diluted in EMEM. Confluent HEp-2 monolayers were infected in duplicates with diluted homogenates in 24 well plates. After one hour incubation at 37° C. in a 5% CO2 incubator, the wells were overlaid with 0.75% methylcellulose medium. After 4 days of incubation, the overlays were removed, and the cells were fixed and stained with 0.1% crystal violet for one hour and then rinsed and air dried. Plaques were counted and plaque forming units per gram of tissue were calculated. The geometric mean virus titers are summarized below in Table 7 for D47 samples and in Table 8 for D63 samples.

For pulmonary histopathology analysis, lungs were dissected, formalin fixed and embedded in paraffin as described above. Lung sections were stained with hematoxylin and eosin (H&E) for analysis of the four parameters of pulmonary inflammation: peribronchiolitis, perivasculitis, interstitial pneumonia, and alveolitis. Slides were scored blind on a 0-4 severity scale. The scores were subsequently converted to a 0-100% histopathology scale. Average pathology scores are summarized below in Table 7 for D47 samples and in Table 8 for D63 samples.

TABLE 7

Lung virus titers and pathology scores on Day 47.

| No. | Description | Lung virus titer D47 (Log10 PFU/g) | Avg. pathology score D47 (0-100%) |
|---|---|---|---|
| 1 | 300 µg 12 in PBS | 2.7 ± 0.2 | 6.50 ± 2.18 |
| 2 | 150 µg 12 in PBS | 2.8 ± 0.2 | 13.0 ± 2.52 |
| 3 | 15 µg 12 in PBS | 3.9 ± 0.6 | 25.0 ± 3.90 |
| 4 | 15 µg 12 + Adju-Phos ® | 3.3 ± 0.6 | 11.58 ± 3.88 |

TABLE 7-continued

Lung virus titers and pathology scores on Day 47.

| No. | Description | Lung virus titer D47 (Log10 PFU/g) | Avg. pathology score D47 (0-100%) |
|---|---|---|---|
| 5 | FI-RSV | 3.9 ± 0.3 | 85.42 ± 2.82 |
| 6 | PBS | 5.8 ± 0.1 | 23.75 ± 4.9 |

All animals immunized with PBS showed maximal viral titers in the lung five days post challenge (mean titer ~5.8 Log 10 PFU/g). Animals immunized with 150 µg or 300 µg of conjugate 12 showed a strong reduction (~3×Log 10) of virus titers compared to the PBS control group. The majority of animals did not have detectable virus in the lungs (Log 10 titer ≤2.6 PFU/g). Animals vaccinated with FI-RSV, 15 µg or 15 µg+Adju-Phos® showed lesser protection (reduction by ~2×Log 10). The adjuvant did not seem to improve the protection. Animals immunized with PBS depicted the pathology typically associated with a primary RSV infection. Animals vaccinated with FI-RSV showed strong pathology, indicative of vaccine associated disease enhancement. All animals immunized with conjugate 12 showed no signs of vaccine associated disease enhancement and equal or lower pathology scores versus PBS control animals.

TABLE 8

Lung virus titers and pathology scores on Day 68.

| No. | Description | Lung virus titer D68 (Log10 PFU/g) | Avg. pathology score D68 (0-100%) |
|---|---|---|---|
| 1 | 300 µg 12 in PBS | 2.6 ± 0.2 | 21.67 ± 4.38 |
| 2 | 150 µg 12 in PBS | 2.9 ± 0.3 | 16.67 ± 3.64 |
| 3 | 15 µg 12 in PBS | 3.6 ± 0.3 | 18.75 ± 4.62 |
| 4 | 15 µg 12 + Adju-Phos ® | 3.3 ± 0.2 | 20.0 ± 3.47 |

Similar virus titers and average pathology scores were obtained for D68. Most animals immunized with 300 µg or 150 µg of conjugate 12 did not show detectable virus (Log 10 titer≤2.6 PFU/g). Adju-Phos© did not impart any benefit.

The results show that two intramuscular immunizations with conjugate 12 without co-administration of an adjuvant are sufficient to high levels of protective neutralizing antibodies and that immunization with conjugate 12 does not cause enhanced respiratory disease over a wide dose range.

Example 5

Generation of Monoclonal Antibody

One mouse was immunized two times with conjugate 12. Twenty-one days after the second immunization, the spleen was surgically removed, the lymphocytes were isolated and further fused with the myeloma Sp2/0Ag 14 (ATCC CRL 8287). The desired hybrid cells were selected in hypoxanthine-aminopterin-thymidine (HAT) medium. B-cell hybridomas secreting (aminooxy)acetylpeptide 4-specific IgG were identified by peptide ELISA and a further screening was performed by Plaque Reduction Neutralization Test (PRNT) against RSV A2 virus. One hybridoma was selected for mAb production. The cloned hybridoma cell line was cultured in suspension using roller bottles (Greiner) containing 650 ml medium and were purified by Protein G High Performance (GE Healthcare). The purified mAb 10D10 was sterile-filtered.

Surface plasmon resonance (SPR) was performed to determine kinetic rate constants for binding to (aminooxy)acetylpeptide 4 on a Biacore T-100 instrument (GE Healthcare) on a CM5 chip using single cycle kinetics and capturing assay protocol using mouse antibody capture kit (GE Healthcare) according to the manufacturer's instructions. The mAb 10D10 bound (aminooxy)acetylpeptide 4 with a fast $k_{on}$ rate and a slow $k_{off}$ rate leading to a KD in the sub nano-molar range (Table 9).

TABLE 9

Kinetic rate constants for binding to (aminooxy)acetylpeptide 4

| Probe | Probe density (RU) | $k_{on}$ ($M^{-1}s^{-1}$) | $k_{off}$ ($s^{-1}$) | KD (M) | RU (max) | Chi2 |
|---|---|---|---|---|---|---|
| 10D10 | 780 | 4.69E+05 | 4.28E−04 | 9.14E−10 | 21.3 | 0.240 |

In order to assess the neutralization capacity of the mAb at 40 µg/ml against RSV A/Tracy a Micro-Neutralization Test (MNT) was performed. A 40 µg/ml Palivizumab stock was taken as positive control and 40 µg/ml stock of an isotype-matched mAb as negative control (Table 10).

TABLE 10

Micro-Neutralization Test (MNT)

| mAb | Concentration of mAb in test solution (µg/ml) | RSV A, Tracy MN titer ($log_2$) |
|---|---|---|
| 10D10 | 40 | 7.0 |
| Palivizumab | 40 | 5.0 |
| Negative control | 40 | 2.0 |

The results show that antibodies with KD's in the sub nano-molar range and neutralizing potency similar or better to that of Palivizumab can be generated in mice after immunization with conjugate 12.

Example 6

Generation of Sequence Variants (Aminooxy)Acetyl Peptide 19

(Formula 19)

AOAc—NSECLSLCND-Nle-PITNDQKKLCSS-Dab-CQSVRa—NH$_2$ (Aminooxy)acetyl peptide 19 (with SEQ ID NO: 39) corresponds to (aminooxy)acetyl peptide 4, except that the amino acid in position 23 is Ser instead of Asn. Peptide 19 is synthesized, cyclized and purified essentially as described above for (aminooxy)acetyl peptide 2.

(Aminooxy)Acetyl Peptide 20

(Formula 20)

AOAc—NSECLSLCND-Nle-PITNDQKKLCSSNCQSVRa—NH$_2$ (Aminooxy)acetyl peptide 20 (with SEQ ID NO: 40) corresponds to (aminooxy)acetyl peptide 19, except that the amino acid in position 24 is Asn instead of Dab. Peptide 20 is synthesized, cyclized and purified essentially as described above for (aminooxy)acetyl peptide 2.

(Aminooxy)acetyl Peptide 21

(Formula 21)

AOAc—NSECLSLCND-Nle-PITNDQKKLCSSQCQSVRa—NH$_2$ (Aminooxy)acetyl peptide 21 (with SEQ ID NO: 41) corresponds to (aminooxy)acetyl peptide 20, except that the amino acid in position 24 is Gln instead of Asn. Peptide 21 is synthesized, cyclized and purified essentially as described above for (aminooxy)acetyl peptide 2.

(Aminooxy)acetyl Peptide 22

(Formula 22)

AOAc—NSECLSLCND-Nle-PITNDQKKLCSSSCQSVRa—NH$_2$ (Aminooxy)acetyl peptide 22 (with SEQ ID NO: 42) corresponds to (aminooxy)acetyl peptide 21, except that that the amino acid in position 24 is Ser instead of Gln. Peptide 22 is synthesized, cyclized and purified essentially as described above for (aminooxy)acetyl peptide 2.

(Aminooxy)acetyl Peptide 23

(Formula 23)

AOAc—QSECLSLCND-Nle-PITNDQKKLCSN-Dab-CQSVRa—NH$_2$ (Aminooxy)acetyl peptide 23 (with SEQ ID NO: 43) corresponds to (aminooxy)acetyl peptide 4, except that the amino acid in position 1 is Gln instead of Asn. Peptide 23 is synthesized, cyclized and purified essentially as described above for (aminooxy)acetyl peptide 2.

(Aminooxy)acetyl Peptide 24

(Formula 24)

AOAc—QSECLSLCND-Nle-PITNDQKKLCSS-Dab-CQSVRa—NH$_2$ (Aminooxy)acetyl peptide 24 (with SEQ ID NO: 44) corresponds to (aminooxy)acetyl peptide 19, except that the amino acid in position 1 is Gln instead of Asn. Peptide 24 is synthesized, cyclized and purified essentially as described above for (aminooxy)acetyl peptide 2.

(Aminooxy)acetyl Peptide 25

(Formula 25)

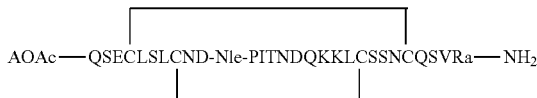

AOAc—QSECLSLCND-Nle-PITNDQKKLCSSNCQSVRa—NH$_2$ (Aminooxy)acetyl peptide 25 (with SEQ ID NO: 45) corresponds to (aminooxy)acetyl peptide 20, except that the amino acid in position 1 is Gln instead of Asn. Peptide 25 is synthesized, cyclized and purified essentially as described above for (aminooxy)acetyl peptide 2.

(Aminooxy)acetyl Peptide 26

(Formula 26)

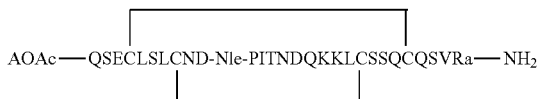

AOAc—QSECLSLCND-Nle-PITNDQKKLCSSQCQSVRa—NH$_2$ (Aminooxy)acetyl peptide 26 (with SEQ ID NO: 46) corresponds to (aminooxy)acetyl peptide 21, except that the amino acid in position 1 is Gln instead of Asn. Peptide 26 is synthesized, cyclized and purified essentially as described above for (aminooxy)acetyl peptide 2.

(Aminooxy)acetyl Peptide 27

(Formula 27)

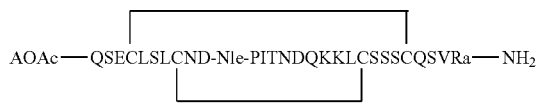

AOAc—QSECLSLCND-Nle-PITNDQKKLCSSSCQSVRa—NH$_2$ (Aminooxy)acetyl peptide 27 (with SEQ ID NO: 47) corresponds to (aminooxy)acetyl peptide 22, except that the amino acid in position 1 is Gln instead of Asn. Peptide 27 is synthesized, cyclized and purified essentially as described above for (aminooxy)acetyl peptide 2.

(Aminooxy)acetyl Peptide 28

(Formula 28)

AOAc—SSECLSLCND-Nle-PITNDQKKLCSN-Dab-CQSVRa—NH$_2$ (Aminooxy)acetyl peptide 28 (with SEQ ID NO: 48) corresponds to (aminooxy)acetyl peptide 23, except that the amino acid in position 1 is Ser instead of Gln. Peptide 28 is synthesized, cyclized and purified essentially as described above for (aminooxy)acetyl peptide 2.

(Aminooxy)acetyl Peptide 29

(Formula 29)

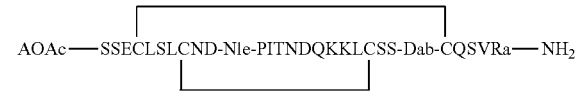

AOAc—SSECLSLCND-Nle-PITNDQKKLCSS-Dab-CQSVRa—NH$_2$ (Aminooxy)acetyl peptide 29 (with SEQ ID NO: 49) corresponds to (aminooxy)acetyl peptide 24, except that the amino acid in position 1 is Ser instead of Gln. Peptide 29 is synthesized, cyclized and purified essentially as described above for (aminooxy)acetyl peptide 2.

(Aminooxy)acetyl Peptide 30

(Formula 30)

AOAc—SSECLSLCND-Nle-PITNDQKKLCSSNCQSVRa—NH₂

(Aminooxy)acetyl peptide 30 (with SEQ ID NO: 50) corresponds to (aminooxy)acetyl peptide 25 except that the amino acid in position 1 is Ser instead of Gln. Peptide 30 is synthesized, cyclized and purified essentially as described above for (aminooxy)acetyl peptide 2.

(Aminooxy)acetyl Peptide 31

(Formula 31)

AOAc—SSECLSLCND-Nle-PITNDQKKLCSSQCQSVRa—NH₂

(Aminooxy)acetyl peptide 31 (with SEQ ID NO: 51) corresponds to (aminooxy)acetyl peptide 26, except that the amino acid in position 1 is Ser instead of Gln. Peptide 27 is synthesized, cyclized and purified essentially as described above for (aminooxy)acetyl peptide 2.

(Aminooxy)acetyl Peptide 32

(Formula 32)

AOAc—SSECLSLCND-Nle-PITNDQKKLCSSSCQSVRa—NH₂

(Aminooxy)acetyl peptide 32 (with SEQ ID NO: 52) corresponds to (aminooxy)acetyl peptide 27, except that the amino acid in position 1 is Ser instead of Gln. Peptide 27 is synthesized, cyclized and purified essentially as described above for (aminooxy)acetyl peptide 2.

(Aminooxy)acetyl Peptide 33

(Formula 33)

AOAc—GSECLSLCND-Nle-PITNDQKKLCSN-Dab-CQSVRa—NH₂

(Aminooxy)acetyl peptide 33 (with SEQ ID NO: 53) corresponds to (aminooxy)acetyl peptide 28, except that the amino acid in position 1 is Gly instead of Ser. Peptide 33 is synthesized, cyclized and purified essentially as described above for (aminooxy)acetyl peptide 2.

(Aminooxy)acetyl Peptide 34

(Formula 34)

AOAc—GSECLSLCND-Nle-PITNDQKKLCSS-Dab-CQSVRa—NH₂

(Aminooxy)acetyl peptide 34 (with SEQ ID NO: 54) corresponds to (aminooxy)acetyl peptide 29, except that the amino acid in position 1 is Gly instead of Ser. Peptide 34 is synthesized, cyclized and purified essentially as described above for (aminooxy)acetyl peptide 2.

(Aminooxy)acetyl Peptide 35

(Formula 35)

AOAc—GSECLSLCND-Nle-PITNDQKKLCSSNCQSVRa—NH₂

(Aminooxy)acetyl peptide 35 (with SEQ ID NO: 55) corresponds to (aminooxy)acetyl peptide 30, except that the amino acid in position 1 is Gly instead of Ser. Peptide 35 is synthesized, cyclized and purified essentially as described above for (aminooxy)acetyl peptide 2.

(Aminooxy)acetyl Peptide 36

(Formula 36)

AOAc—GSECLSLCND-Nle-PITNDQKKLCSSQCQSVRa—NH₂

(Aminooxy)acetyl peptide 36 (with SEQ ID NO: 56) corresponds to (aminooxy)acetyl peptide 31, except that the amino acid in position 1 is Gly instead of Ser. Peptide 36 is synthesized, cyclized and purified essentially as described above for (aminooxy)acetyl peptide 2.

(Aminooxy)acetyl Peptide 37

(Formula 37)

AOAc—GSECLSLCND-Nle-PITNDQKKLCSSSCQSVRa—NH₂

(Aminooxy)acetyl peptide 37 (with SEQ ID NO: 57) corresponds to (aminooxy)acetyl peptide 32, except that the amino acid in position 1 is Gly instead of Ser. Peptide 37 is synthesized, cyclized and purified essentially as described above for (aminooxy)acetyl peptide 2.

The invention claimed is:

1. A cyclic peptide comprising an amino acid sequence (I), wherein said amino acid sequence (I) comprises the amino acid sequence:

X1-X2-X3-C4-X5-X6-X7-C8-X9-X10-X11-P12-I13-
T14-N15-D16-Q17-K18-K19-L20-C21-X22-
X23-X24-C25-X26-X27-X28-X29-X30 (SEQ ID NO: 1), wherein X1, X2, X3, X5, X6, X7, X9, X10, X11, X22, X23, X24, X26, X27, X28 and X29 are independently of each other an amino acid;
C4, C8, C21 and C25 are independently of each other cysteine;
P12 is proline;
I13 is isoleucine;
T14 is threonine;
N15 is asparagine;
D16 is aspartic acid;
Q17 is glutamine;
K18 and K19 are independently of each other lysine;
L20 is leucine; and
X30 is an amino acid or a deletion,
wherein said cysteines C4 and C25 form a first disulfide bond and said cysteines C8 and C21 form a second disulfide bond.

2. The cyclic peptide of claim 1, wherein said cyclic peptide has a length of at most 80 amino acids.

3. The cyclic peptide of claim 1, wherein X11 is selected from norleucine, 6-hydroxy-norleucine, norvaline, 5-oxo-norleucine, 2-aminoheptanoic acid, methionine, ethionine, hydroxy-methionine, s-oxymethionine, methionine sulfone, or methionine sulfoxide.

4. The cyclic peptide of claim 1, wherein X23 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

5. The cyclic peptide of claim 1, wherein X24 is selected from asparagine, beta-hydroxyasparagine, 2,5-diamino-4-hydroxy-5-oxopentanoic acid, glutamine, glutamine hydroxamate, 3-methyl-glutamine, n-methyl-asparagine, n5-methyl-glutamine, cysteine-s-acetamide; lysine, 2,4-diaminobutyric acid, 2,3-diaminopropanoic acid, 2,8-diaminooctanoic acid, ornithine, amino-adipic acid, thialysine; aspartic acid, 2-amino-6-oxopimelic acid, 3-methyl-aspartic acid, 1-2-amino-6-methylene-pimelic acid, 4-hydroxy-glutamic-acid, 6-carboxylysine, beta-hydroxyaspartic acid, 3,3-dimethyl aspartic acid, 2-amino-propanedioic acid, glutamate, 5-o-methyl-glutamic acid, (3r)-3-methyl-l-glutamic acid, (3s)-3-methyl-l-glutamic acid, 2s,4r-4-methylglutamate 2-aminoadipic acid, serine, homoserine, allo-threonine, 3,3-dihydroxy-alanine, 2-amino-5-hydroxypentanoic acid, 4-hydroxy-l-threonine, threonine, hydroxynorvaline, 6-hydroxy-l-norleucine or glycine.

6. The cyclic peptide of claim 1, wherein the C-terminal amino acid of said amino acid sequence (I) is selected from alanine, leucine, valine, norleucine, norvaline, isoleucine, homoleucine, vinylglycine, 2-aminobutyric acid, 2-allylglycine, alloleucine, alloisoleucine, 2-aminoheptanoic acid, serine, glutamine or glycine.

7. The cyclic peptide of claim 1, wherein the amino acid sequence (I) is an amino acid sequence selected from any one of SEQ ID NO: 2, SEQ ID NO: 3, SEQ ID NO: 4, SEQ ID NO:5, SEQ ID NO: 16 to SEQ ID NO: 36 or SEQ ID NO: 39 to 57.

8. The cyclic peptide of claim 1 further comprising a linker, wherein said linker is attached to said amino acid sequence (I), and wherein said linker comprises (i) at least one attachment moiety, (ii) at least one spacer moiety, (iii) at least one linking moiety, or (iv) any combination of (i), (ii) and (iii).

9. The cyclic peptide of claim 8, wherein said linker is selected from the following formulas:

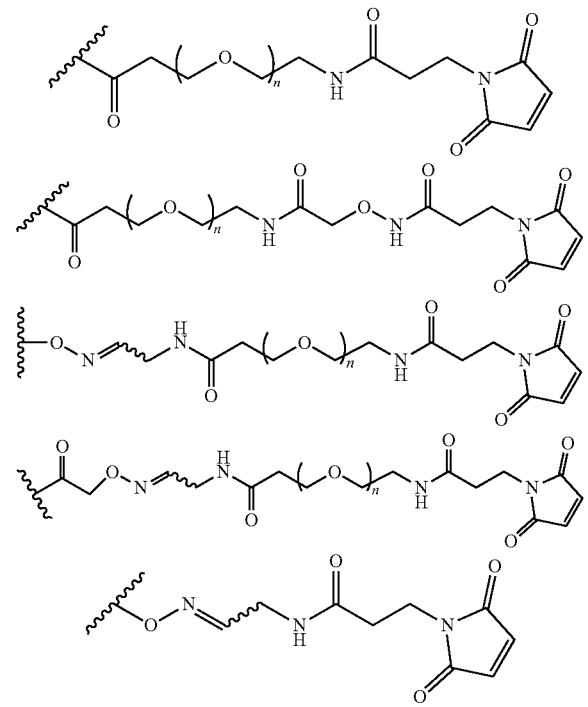

-continued

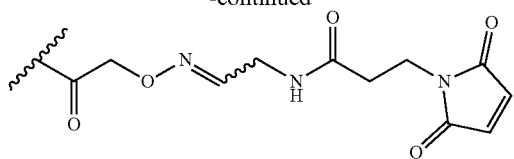

wherein n is an integer of 1 to 45, and the wavy line indicates the attachment site to said amino acid sequence (I).

10. A conjugate comprising
(a) a lipopeptide building block, and
(b) the cyclic peptide of claim 1,
wherein said lipopeptide building block consists of
(i) a peptide moiety comprising at least one coiled coil peptide chain segment, and
(ii) a lipid moiety comprising two or three hydrocarbyl chains;
and wherein said cyclic peptide is connected, directly or via a linker, to said lipopeptide building block.

11. The conjugate of claim 10, wherein said conjugate is selected from any one of the formulas

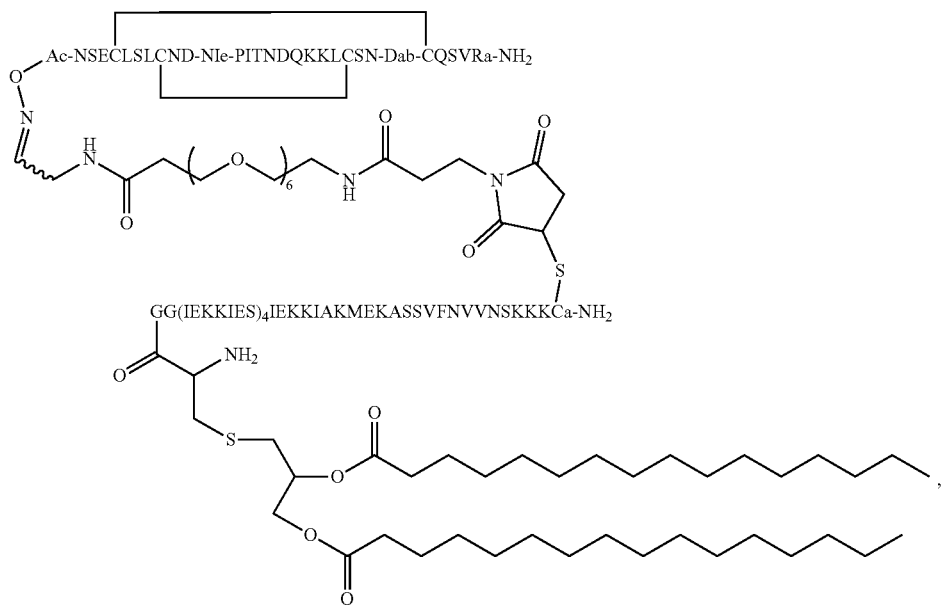

(12)

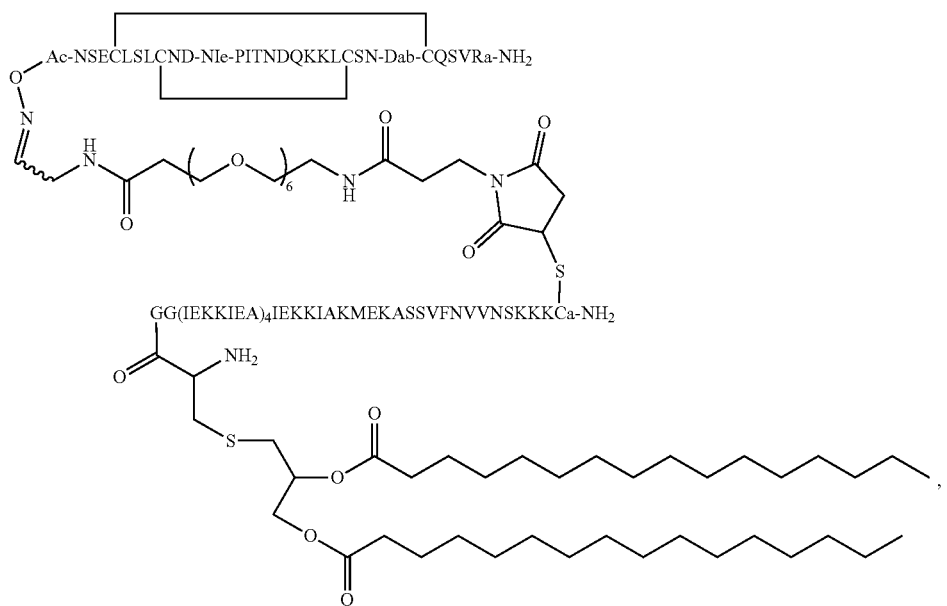

(13)

(14)
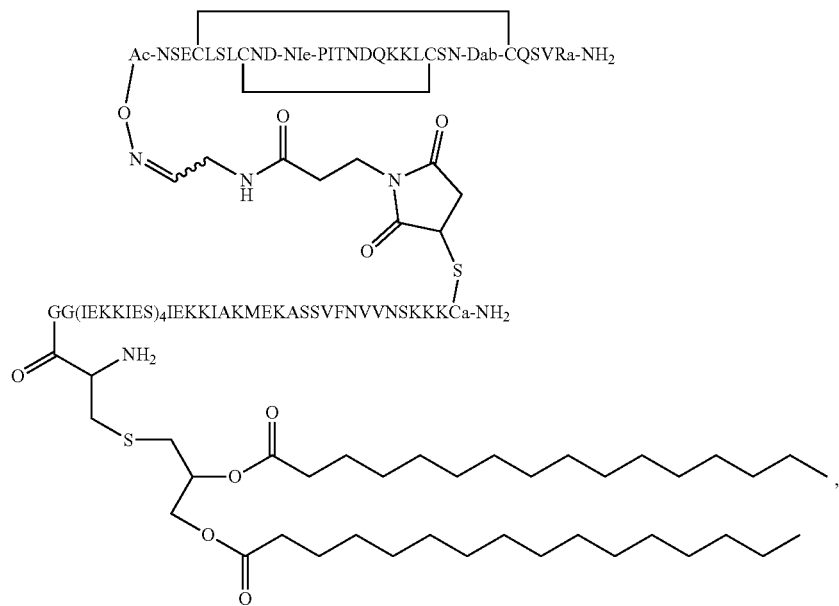
(15)
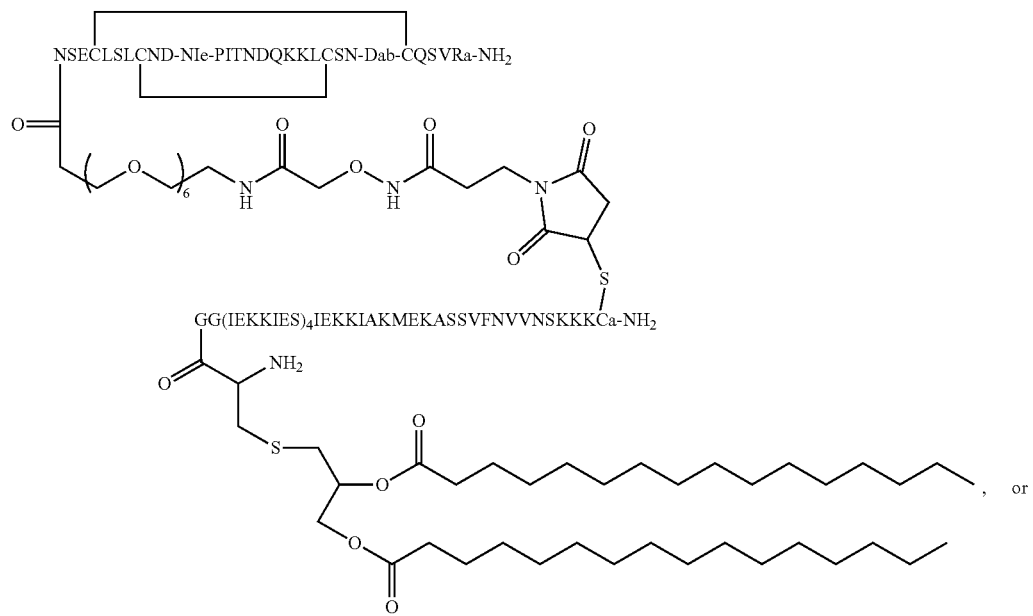
, or (16)

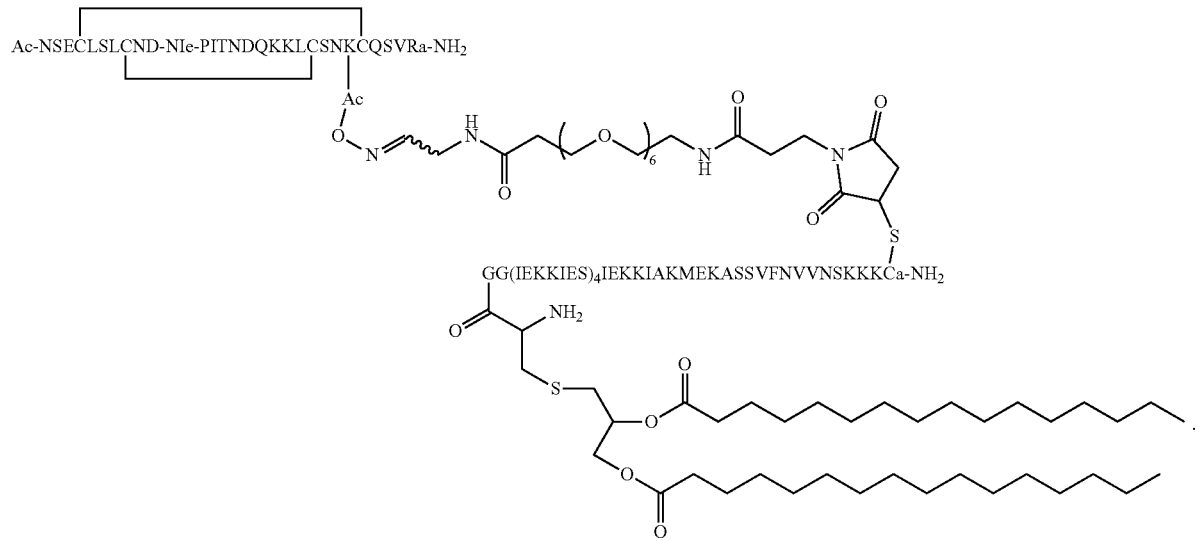

12. A bundle of conjugates comprising 2, 3, 4, 5, 6 or 7 conjugates of claim 10.

13. A synthetic virus-like particle comprising at least one bundle of conjugates of claim 11.

14. A pharmaceutical composition comprising an immunologically effective amount of the synthetic virus like particle of claim 13, together with a pharmaceutically acceptable diluent, carrier or excipient.

15. The cyclic peptide of claim 1, wherein said cyclic peptide has a length of at most 40 amino acids.

16. The cyclic peptide of claim 8 wherein said at least one attachment moiety comprises —O—NH$_2$, —O—NH—, —C(O)—CH$_2$—O—NH$_2$, —C(O)—CH$_2$—O—NH—, —N—NH$_2$, —N—NH—, -E(O)—NH—NH$_2$, or -E(O)—NH—NH—, wherein E is C, S(O) or P.

17. The conjugate of claim 10, wherein said lipid moiety comprises two hydrocarbyl chains.

18. The conjugate of claim 10, wherein said conjugate is of formula 12.

19. The cyclic peptide of claim 16, wherein said at least one spacer moiety comprises NH$_2$—CH$_2$—CH$_2$—(O—CH$_2$—CH$_2$)$_n$—C(O)— or —NH—CH$_2$—CH$_2$—(O—CH$_2$—CH$_2$)$_n$—C(O)—, wherein n is an integer of 2 to 20; or NH$_2$—(CH$_2$)$_m$—C(O)— or —NH—(CH$_2$)$_m$—C(O)—, wherein m is an integer of 2 to 20; and wherein said at least one linking moiety is capable of cross-linking the cyclic peptide with a second peptide.

20. The cyclic peptide of claim 16, wherein said at least one spacer moiety comprises NH$_2$—CH$_2$—CH$_2$—(O—CH$_2$—CH$_2$)$_n$—C(O)— or —NH—CH$_2$—CH$_2$—(O—CH$_2$—CH$_2$)$_n$—C(O)—, wherein n is an integer of 6 to 8; or NH$_2$—(CH$_2$)$_m$—C(O)— or —NH—(CH$_2$)$_m$—C(O)—, wherein m is an integer of 2 to 6; and wherein said at least one linking moiety is capable of cross-linking the cyclic peptide with a second peptide.

* * * * *